United States Patent
Olsen et al.

(10) Patent No.: US 11,518,815 B2
(45) Date of Patent: *Dec. 6, 2022

(54) ANTI-ROR1 ANTIBODIES AND METHODS OF MAKING AND USING THEREOF

(71) Applicants: SYSTIMMUNE, INC., Redmond, WA (US); SICHUAN BAILI PHARMACEUTICAL CO. LTD., Chengdu (CN)

(72) Inventors: Ole Olsen, Everett, WA (US); Phil Tan, Edmonds, WA (US); Dong Xia, Redmond, WA (US); David Jellyman, Duvall, WA (US); Brian Kovacevich, Snohomish, WA (US); Bill Brady, Bothell, MA (US); Blair Renshaw, Renton, WA (US); Zeren Gao, Redmond, WA (US); Yi Zhu, Chengdu (CN)

(73) Assignees: SYSTIMMUNE, INC., Rdmond, WA (US); BAILI-BIO (CHENGDU) PHARMACEUTICAL CO., LTD., Sichuan (CN)

( * ) Notice: Subject to any disclaimer, the term of this patent is extended or adjusted under 35 U.S.C. 154(b) by 115 days.

This patent is subject to a terminal disclaimer.

(21) Appl. No.: 16/615,116

(22) PCT Filed: Jun. 22, 2018

(86) PCT No.: PCT/US2018/039152
§ 371 (c)(1),
(2) Date: Nov. 19, 2019

(87) PCT Pub. No.: WO2019/005636
PCT Pub. Date: Jan. 3, 2019

(65) Prior Publication Data
US 2021/0277109 A1    Sep. 9, 2021

Related U.S. Application Data

(60) Provisional application No. 62/551,035, filed on Aug. 28, 2017, provisional application No. 62/551,032, filed on Aug. 28, 2017, provisional application No. 62/551,065, filed on Aug. 28, 2017, provisional application No. 62/545,603, filed on Aug. 15, 2017, provisional application No. 62/524,557, filed on Jun. 25, 2017, provisional application No. 62/524,554, filed on Jun. 25, 2017, provisional application No. 62/524,558, filed on Jun. 25, 2017.

(51) Int. Cl.
*A61K 45/06* (2006.01)
*C07K 16/28* (2006.01)
*A61K 39/395* (2006.01)
*A61K 39/00* (2006.01)

(52) U.S. Cl.
CPC ...... *C07K 16/2878* (2013.01); *A61K 39/3955* (2013.01); *A61K 45/06* (2013.01); *C07K 16/2803* (2013.01); *A61K 2039/505* (2013.01); *C07K 2317/24* (2013.01); *C07K 2317/31* (2013.01); *C07K 2317/92* (2013.01)

(58) Field of Classification Search
CPC ............. A61K 39/3955; A61K 45/06; C07K 16/2803; C07K 2317/24; C07K 2317/31; C07K 2317/92
USPC ...................................................... 424/143.1
See application file for complete search history.

(56) References Cited

PUBLICATIONS

Harmsen and Haard (Appl Microbiol Biotechnol 2007, 77:13-22).*
Rudikoff et al (Proc. Natl. Acad. Sci. USA, 79(6): 1979-1983, Mar. 1982).*
Colman P. M. (Research in Immunology, 145:33-36, 1994).*

* cited by examiner

*Primary Examiner* — Yan Xiao
(74) *Attorney, Agent, or Firm* — Zhihua Han

(57) ABSTRACT

The application provides anti-ROR1 monoclonal antibodies, antigen binding portions thereof, therapeutic compositions thereof and/or nucleic acid encoding the same, and their use to upregulate the function of T-cells to enhance cell-mediated immune responses in the treatment of cancer and other T-cell dysfunctional disorders.

11 Claims, 8 Drawing Sheets

Specification includes a Sequence Listing.

FIGURE 1 shows the Immunization strategy

| Immunization No. | Day | Antigen | Adjuvant Cohort 1 | Cohort 2 | Dose per rabbit |
|---|---|---|---|---|---|
| 1 | 0 | Human ROR1 ECD | Complete Freunds | Titermax | 30 ug |
| 2 | 7 | Human ROR1 cells | Alum/CpG 2007 | Alum/CpG 2007 | 10 x 10e6 |
| 3 | 14 | Mouse ROR1 ECD | Incomplete Freunds | Titermax | 10 ug |
| 4 | 21 | Mouse ROR1 cells | Alum/CpG 2007 | Alum/CpG 2007 | 10 x 10e6 |
| 5 | 28 | Human ROR1 ECD | Incomplete Freunds | Titermax | 10 ug |
| 6 | 37 | Human ROR1 cells | No adjuvant - IP only | No adjuvant - IP only | 10 x 10e6 |

FIGURE 2 shows the Immunization Schedule

|  | Sept | | | | Oct | | | | Nov |
|---|---|---|---|---|---|---|---|---|---|
| Immunogen | 9 | 16 | 23 | 30 | 7 | 16 | 20 | 30 | 6 |
| Human ROR1-HIS | 0 | | | | | | | | |
| Human ROR1-Cells | | 7 | | | | | | | |
| Mouse ROR1-HIS | | | 14 | | | | | | |
| Mouse ROR1-Cells | | | | 21 | | | | | |
| Human ROR1-HIS | | | | | 28 | | | | |
| Serology days 29-35 | | | | | | | | | |
| Human ROR1-Cells | | | | | | 37 | | | |
| Harvest day 4 post-immunization | | | | | | | 41 | | |
| Harvest day 14 post-immunization | | | | | | | | 51 | |
| Harvest day 21 post-immunization | | | | | | | | | 58 |

FIGURE 3 shows day of tissue harvest post-final immunization

|  | Freunds/(Alum/CpG) | | | Titermax/(Alum/CpG) | | |
|---|---|---|---|---|---|---|
| Cohort | 1 | | | 2 | | |
| Rabbit ID# | 6378R | 6392R | R6234 | 6606R | 6068R | R6513 |
| Days post | 4 | 13 | 21 | 4 | 13 | 21 |

FIGURE 4 Summary of native rabbit IgG antibody in B cell culture supernatant or chimeric recombinant rabbit/human IgG antibody binding activity.

| | | BCC well ID | Human ROR1 directly coated on the plate – detection of ROR1-specific IgG ELISA (OD$_{450}$) | Biotinylated human ROR1 added to an avidin coated plate - detection of ROR1-specific IgG ELISA (OD$_{450}$) | Biotinylated human ROR1 "Kringle domain" added to an avidin coated plate - detection of ROR1-Kringle specific IgG ELISA (OD$_{450}$) | Human ROR2 directly coated on the plate – detection of ROR1-specific IgG ELISA (OD$_{450}$) | Mouse ROR1 directly coated on the plate – detection of ROR1-specific IgG ELISA (OD$_{450}$) | Human ROR1 "Frizzled-Kringle domain" directly coated on the plate - detection of ROR1-Frizzled-Kringle-specific IgG ELISA (OD$_{450}$) | Biotinylated human ROR1 "Frizzled-Kringle domain" added to an avidin coated plate - detection of ROR1-Frizzled-Kringle-specific IgG ELISA (OD$_{450}$) | Human ROR1 "Ig-Frizzled domain" directly coated on the plate - detection of ROR1-Ig-Frizzled-specific IgG ELISA (OD$_{450}$) | Biotinylated human ROR1 "Ig-Frizzled domain" added to an avidin coated plate - detection of ROR1-Ig-Frizzled-specific IgG ELISA (OD$_{450}$) | Human ROR1 CHO cells – detection of ROR1-specific IgG by FACS (MFI) |
|---|---|---|---|---|---|---|---|---|---|---|---|---|
| Kringle-specific (mouse cross-reactive) | 1 | 226E12 | nd | nd | 0.41 | 0.09 | 0.25 | nd | nd | nd | nd | 13 |
| | 2 | 340F4 | 1.80 | 0.46 | 4.00 | 0.15 | 2.27 | 1.03 | 0.45 | 0.19 | 0.16 | 7 |
| | 3 | 339G5 | 1.15 | 0.23 | 4.00 | 0.12 | 2.38 | 0.87 | 0.34 | 0.15 | 0.27 | 7 |
| | 4 | 340D5 | 0.59 | 0.13 | 0.89 | 0.11 | 1.17 | 0.36 | 0.21 | 0.10 | 0.13 | 7 |
| | 5 | 341F4 | 0.41 | 0.12 | 3.33 | 0.19 | 1.09 | 0.27 | 0.21 | 0.15 | 0.13 | 7 |
| | 6 | 329E12 | 0.55 | nd | nd | 0.24 | 4.00 | 1.86 | 2.50 | 0.25 | 0.18 | 9 |
| | 7 | 330F11 | 0.98 | nd | nd | 0.25 | 4.00 | 1.89 | 1.71 | 0.28 | 0.15 | 5 |
| Ig domain-specific (mouse cross-reactive) | 8 | 327C2 | 2.20 | nd | nd | 0.21 | 4.00 | 0.20 | 0.13 | 2.15 | 1.19 | 198 |
| | 9 | 322C10 | 1.93 | nd | nd | 0.20 | 4.00 | 0.18 | 0.16 | 2.04 | 2.50 | 196 |
| | 10 | 330F2 | 1.13 | nd | nd | 0.17 | 0.65 | 0.16 | 0.17 | 2.11 | 0.40 | 106 |
| | 11 | 324E2 | 0.48 | nd | nd | 0.21 | 2.17 | 0.18 | 0.10 | 1.29 | 0.62 | 25 |
| | 12 | 324G10 | 1.47 | nd | nd | 0.17 | 4.00 | 0.17 | 0.17 | 2.73 | 1.05 | 22 |
| | 13 | 323D10 | 2.82 | nd | nd | 0.23 | 4.00 | 0.32 | 0.17 | 1.94 | 2.23 | 20 |
| | 14 | 331E1 | 0.77 | nd | nd | 0.25 | 4.00 | 0.12 | 0.11 | 2.65 | 1.25 | 10 |
| Ig domain-specific (NOT mouse cross-reactive) | 15 | 323A3 | 1.97 | nd | nd | 0.18 | 0.29 | 0.18 | 0.17 | 2.46 | 2.34 | 340 |
| | 16 | 327F11 | 2.91 | nd | nd | 0.21 | 0.20 | 0.17 | 0.21 | 2.96 | 2.56 | 320 |
| | 17 | 324H4 | 3.61 | nd | nd | 0.21 | 0.23 | 0.17 | 0.15 | 1.99 | 3.03 | 296 |
| | 18 | 330F7 | 1.23 | nd | nd | 0.20 | 0.17 | 0.16 | 0.16 | 2.27 | 1.43 | 294 |
| | 19 | 326C11 | 2.90 | nd | nd | 0.16 | 0.18 | 0.22 | 0.11 | 2.77 | 1.14 | 234 |
| | 20 | 324G3 | 2.56 | nd | nd | 0.17 | 0.18 | 0.15 | 0.13 | 1.83 | 1.93 | 222 |
| | 21 | 326E12 | 0.46 | nd | nd | 0.20 | 0.19 | 0.15 | 0.13 | 2.49 | 1.21 | 216 |
| | 22 | 324C7 | 2.74 | nd | nd | 0.18 | 0.21 | 0.13 | 0.13 | 2.46 | 2.67 | 190 |
| | 23 | 332A7 | 1.32 | nd | nd | 0.26 | 0.19 | 0.16 | 0.14 | 1.94 | 0.98 | 104 |
| | 24 | 323H7 | 1.82 | nd | nd | 0.18 | 0.20 | 0.16 | 0.16 | 1.67 | 1.78 | 90 |
| Frizzled domain-specific (mouse cross-reactive) | 25 | 324C6 | 1.05 | nd | nd | 0.17 | 4.00 | 2.04 | 2.71 | 2.66 | 1.12 | 49 |
| | 26 | 338H4 | 4.00 | nd | nd | 0.17 | 4.00 | 3.01 | 1.80 | 2.77 | 0.22 | 277 |
| | 27 | 339B7 | 4.00 | nd | nd | 0.21 | 3.32 | 2.95 | 3.21 | 3.16 | 2.96 | 61 |

FIGURE 4a Rabbit IgG in B cell culture supernatant analyzed for binding to various full length forms of recombinant human or mouse ROR1, human ROR2, or truncated recombinant fragments of human ROR1.

|  |  | BCC well ID | Mono-valent binding to human ROR1 kdis(1/s) | Bi-valent binding to human ROR1 kdis(1/s) | Mouse ROR1 kdis(1/s) | Human ROR2 kdis(1/s) | Human ROR1 "Frizzled-Kringle domain kdis(1/s) | Human ROR1 "Ig-Frizzled domain" kdis(1/s) | Human ROR1 CHO FACS | Mouse ROR1 CHO FACS |
|---|---|---|---|---|---|---|---|---|---|---|
| Kringle-specific (mouse cross-reactive) | 1 | 226E12 | nd | 3.40E-03 | nd | nd | nd | nd | YES | nd |
| | 2 | 340F4 | WEAK | 2.28E-10 | YES | NEG | YES | NEG | NEG | nd |
| | 3 | 339G5 | WEAK | 1.55E-10 | YES | NEG | YES | NEG | YES | nd |
| | 4 | 340D5 | NEG | 5.22E-10 | NEG | NEG | NEG | NEG | NEG | nd |
| | 5 | 341F4 | WEAK | 2.28E-10 | YES | NEG | YES | NEG | NEG | nd |
| | 6 | 329E12 | WEAK | 1.79E-10 | YES | NEG | YES | NEG | YES | nd |
| | 7 | 330F11 | 1.26E-08 | 6.37E-10 | YES | NEG | YES | NEG | YES | nd |
| Ig domain-specific (mouse cross-reactive) | 8 | 327C2 | 1.64E-08 | 1.85E-08 | NEG | NEG | NEG | YES | YES | YES |
| | 9 | 322C10 | 1.42E-10 | 5.44E-03 | YES | NEG | NEG | YES | YES | YES |
| | 10 | 330F2 | NEG | 9.33E-03 | NEG | NEG | NEG | NEG | YES | YES |
| | 11 | 324E2 | 1.60E-10 | 5.72E-03 | YES | NEG | NEG | YES | YES | YES |
| | 12 | 324G10 | 3.16E-06 | 4.37E-06 | YES | NEG | NEG | YES | YES | YES |
| | 13 | 323D10 | 1.11E-10 | 9.61E-03 | YES | NEG | NEG | YES | YES | YES |
| | 14 | 331E1 | 1.89E-09 | 1.24E-02 | YES | NEG | NEG | YES | YES | YES |
| Ig domain-specific (NOT mouse cross-reactive) | 15 | 323A3 | NEG | 9.89E-03 | NEG | NEG | NEG | NEG | YES | NEG |
| | 16 | 327F11 | NEG | 3.22E-08 | NEG | NEG | NEG | YES | YES | WEAK |
| | 17 | 324H4 | 1.31E-08 | 9.74E-09 | NEG | NEG | NEG | YES | YES | WEAK |
| | 18 | 330F7 | 8.98E-10 | 9.19E-03 | NEG | NEG | NEG | YES | YES | WEAK |
| | 19 | 326C11 | 3.76E-08 | 1.58E-08 | NEG | NEG | NEG | YES | YES | NEG |
| | 20 | 324G3 | 4.03E-09 | 9.72E-09 | NEG | NEG | NEG | YES | YES | NEG |
| | 21 | 326E12 | 2.87E-10 | 1.30E-02 | NEG | NEG | NEG | YES | YES | WEAK |
| | 22 | 324C7 | 1.35E-08 | 3.55E-08 | NEG | NEG | NEG | YES | YES | NEG |
| | 23 | 332A7 | 1.03E-08 | 5.25E-03 | NEG | NEG | NEG | YES | YES | WEAK |
| | 24 | 323H7 | 2.08E-08 | 6.20E-03 | NEG | NEG | NEG | YES | YES | NEG |
| Frizzled domain-specific (mouse cross-reactive) | 25 | 324C6 | 1.69E-05 | 2.35E-07 | NEG | NEG | YES | YES | YES | YES |
| | 26 | 338H4 | 1.17E-08 | 1.01E-10 | YES | NEG | YES | YES | YES | YES |
| | 27 | 339B7 | 4.00E-08 | 8.50E-05 | YES | NEG | YES | YES | YES | YES |

FIGURE 4b Chimeric rabbit/human IgG analyzed for binding to various full length forms of recombinant human or mouse ROR1, ROR2, or truncated recombinant fragments of human ROR1

FIGURE 5 Full length human IgG1 antibodies with humanized ROR1-specific variable region binding domains analyzed for the rate of antibody dissociation from monovalent binding to recombinant full length human ROR1 by Octet.

|   | Humanized ROR1-specific antibody | Monovalent binding to human ROR1 kdis(1/s) |
|---|---|---|
| 1 | 226E12-L1H1 | 4.15E-02 |
| 2 | 323H7-L1H4 | 7.00E-04 |
| 3 | 324C7-L1H1 | 1.87E-03 |
| 4 | 323D10-L3H2 | 4.24E-03 |
| 5 | 324E2-L6H3 | 6.10E-03 |
| 6 | 324C6-L1H2 | 4.03E-02 |
| 7 | 338H4-L4H3 | 2.38E-03 |
| 8 | 330F11-L1H1 | 2.97E-02 |

FIGURE 6     ELISA analysis of rabbit serum IgG binding to human and mouse ROR1
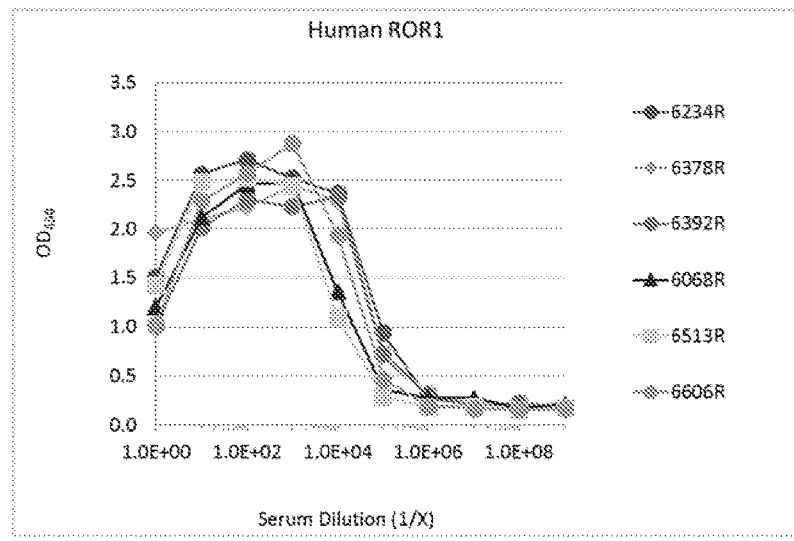
FIGURE 6A Serum from rabbits immunized with human and mouse cell expressed ROR1 analyzed for IgG binding of recombinant human ROR1 by ELISA.
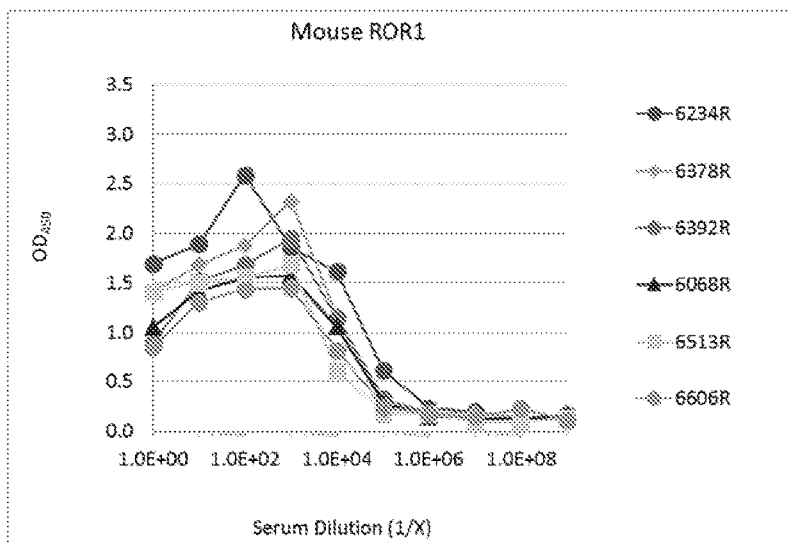
FIGURE 6B Serum from rabbits immunized with human and mouse cell expressed ROR1 analyzed for IgG binding of recombinant mouse ROR1 by ELISA.

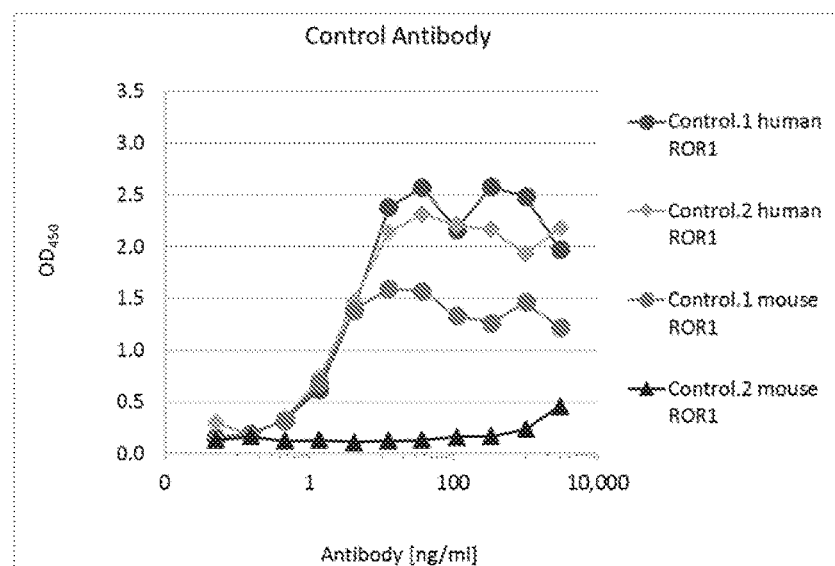
FIGURE 6C Control human IgG1 antibodies analyzed for binding to recombinant human or mouse ROR1 by ELISA.

SEQUENCE LISTING

<160> NUMBER OF SEQ ID NOS: 132

<210> SEQ ID NO 1
<211> LENGTH: 651
<212> TYPE: DNA
<213> ORGANISM: Artificial Sequence
<220> FEATURE:
<223> OTHER INFORMATION: synthesized

<400> SEQUENCE: 1

```
gcctatgata tgacccagac tccatcctcc gtgtctgcag ctgtgggagg cacagtcacc      60
atcaagtgcc aggccagtca gagaatttac agctacttag cctggtatca gcagaaacca     120
gggcagcctc ccaagctcct gatctacagg gcatccactc tggcatctgg ggtcccatcg     180
cggttcaaag gcagtggatc tgggacagag tacactctca ccatcagcga cctggagtgt     240
gccgatgctg ccacttacta ctgtcaacag ggtgctagta tggttgatgt tgagaatatg     300
ttcggcggag ggaccgaggt ggtggtcaaa cgtacggtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg t              651
```

<210> SEQ ID NO 2
<211> LENGTH: 330
<212> TYPE: DNA
<213> ORGANISM: Artificial Sequence
<220> FEATURE:
<223> OTHER INFORMATION: synthesized

<400> SEQUENCE: 2

```
gcctatgata tgacccagac tccatcctcc gtgtctgcag ctgtgggagg cacagtcacc      60
atcaagtgcc aggccagtca gagaatttac agctacttag cctggtatca gcagaaacca     120
```

```
gggcagcctc ccaagctcct gatctacagg gcatccactc tggcatctgg ggtcccatcg    180
cggttcaaag gcagtggatc tgggacagag tacactctca ccatcagcga cctggagtgt    240
gccgatgctg ccacttacta ctgtcaacag gtgctagta tggttgatgt tgagaatatg    300
ttcggcggag ggaccgaggt ggtggtcaaa                                    330
```

<210> SEQ ID NO 3
<211> LENGTH: 217
<212> TYPE: PRT
<213> ORGANISM: Artificial Sequence
<220> FEATURE:
<223> OTHER INFORMATION: synthesized

<400> SEQUENCE: 3

```
Ala Tyr Asp Met Thr Gln Thr Pro Ser Ser Val Ser Ala Ala Val Gly
1               5                   10                  15

Gly Thr Val Thr Ile Lys Cys Gln Ala Ser Gln Arg Ile Tyr Ser Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Gln Gly Ala Ser Met Val Asp
                85                  90                  95

Val Glu Asn Met Phe Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 4
<211> LENGTH: 110
<212> TYPE: PRT
<213> ORGANISM: Artificial Sequence
<220> FEATURE:
<223> OTHER INFORMATION: synthesized

<400> SEQUENCE: 4

```
Ala Tyr Asp Met Thr Gln Thr Pro Ser Ser Val Ser Ala Ala Val Gly
1               5                   10                  15

Gly Thr Val Thr Ile Lys Cys Gln Ala Ser Gln Arg Ile Tyr Ser Tyr
            20                  25                  30

Leu Ala Trp Tyr Gln Gln Lys Pro Gly Gln Pro Pro Lys Leu Leu Ile
        35                  40                  45
```

Tyr Arg Ala Ser Thr Leu Ala Ser Gly Val Pro Ser Arg Phe Lys Gly
 50                  55                  60

Ser Gly Ser Gly Thr Glu Tyr Thr Leu Thr Ile Ser Asp Leu Glu Cys
 65                  70                  75                  80

Ala Asp Ala Ala Thr Tyr Tyr Cys Gln Gln Gly Ala Ser Met Val Asp
                 85                  90                  95

Val Glu Asn Met Phe Gly Gly Gly Thr Glu Val Val Val Lys
            100                 105                 110

<210> SEQ ID NO 5
<211> LENGTH: 1341
<212> TYPE: DNA
<213> ORGANISM: Artificial Sequence
<220> FEATURE:
<223> OTHER INFORMATION: synthesized

<400> SEQUENCE: 5

```
cagtcgctgg aggagtccgg gggtcgcctg gtcacgcctg ggacacccct gacactcacc      60
tgcacagcct ctgaattctc cctcagtaac tactacatga gctgggtccg ccaggctcca     120
ggggaggggc tggagtggat cggagccatt aatgctgaca gtgataatac atggtacccg     180
agctgggtga aaggccgatt caccatctcc aaaacctcgt cgaccacggt ggatctgaag     240
atcaccagtc cgacaattga ggacacggcc acctatttct gtgccagaag tgtgagtaat     300
aatttcgccg aatataacat ctggggcccg ggcaccctgg tcaccgtctc gagcgctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcacccca gacctacatc     600
tgcaacgtga atcacaagcc cagcaacacc aaggtggaca gagagttga cccaaatct     660
tgtgacaaaa ctcacacatg cccaccgtgc ccagcacctg aagccgcggg ggcaccgtca     720
gtcttcctct tccccccaaa acccaaggac accctcatga tctcccggac ccctgaggtc     780
acatgcgtgt ggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgt cagcgtcct caccgtcctg caccaggact ggctgaatgg caaggagtac     960
aagtgcgcgg tctccaacaa agccctccca gcccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtctccggg t                                              1341
```

<210> SEQ ID NO 6
<211> LENGTH: 354
<212> TYPE: DNA
<213> ORGANISM: Artificial Sequence
<220> FEATURE:
<223> OTHER INFORMATION: synthesized

<400> SEQUENCE: 6

```
cagtcgctgg aggagtccgg gggtcgcctg gtcacgcctg ggacacccct gacactcacc      60
```

```
tgcacagcct ctgaattctc cctcagtaac tactacatga gctgggtccg ccaggctcca    120
ggggaggggc tggagtggat cggagccatt aatgctgaca gtgataatac atggtacccg    180
agctgggtga aggccgatt caccatctcc aaaacctcgt cgaccacggt ggatctgaag    240
atcaccagtc cgacaattga ggacacggcc acctatttct gtgccagaag tgtgagtaat    300
aatttcgccg aatataacat ctggggcccg ggcaccctgg tcaccgtctc gagc          354
```

<210> SEQ ID NO 7
<211> LENGTH: 447
<212> TYPE: PRT
<213> ORGANISM: Artificial Sequence
<220> FEATURE:
<223> OTHER INFORMATION: synthesized

<400> SEQUENCE: 7

```
Gln Ser Leu Glu Glu Ser Gly Gly Arg Leu Val Thr Pro Gly Thr Pro
1               5                   10                  15

Leu Thr Leu Thr Cys Thr Ala Ser Glu Phe Ser Leu Ser Asn Tyr Tyr
            20                  25                  30

Met Ser Trp Val Arg Gln Ala Pro Gly Glu Gly Leu Glu Trp Ile Gly
        35                  40                  45

Ala Ile Asn Ala Asp Ser Asp Asn Thr Trp Tyr Pro Ser Trp Val Lys
    50                  55                  60

Gly Arg Phe Thr Ile Ser Lys Thr Ser Ser Thr Val Asp Leu Lys
65                  70                  75                  80

Ile Thr Ser Pro Thr Ile Glu Asp Thr Ala Thr Tyr Phe Cys Ala Arg
                85                  90                  95

Ser Val Ser Asn Asn Phe Ala Glu Tyr Asn Ile Trp Gly Pro Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
```

```
            305                 310                 315                 320
Lys Cys Ala Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly
                435                 440                 445
```

<210> SEQ ID NO 8
<211> LENGTH: 118
<212> TYPE: PRT
<213> ORGANISM: Artificial Sequence
<220> FEATURE:
<223> OTHER INFORMATION: synthesized

<400> SEQUENCE: 8

```
Gln Ser Leu Glu Glu Ser Gly Gly Arg Leu Val Thr Pro Gly Thr Pro
1               5                   10                  15
Leu Thr Leu Thr Cys Thr Ala Ser Glu Phe Ser Leu Ser Asn Tyr Tyr
                20                  25                  30
Met Ser Trp Val Arg Gln Ala Pro Gly Glu Gly Leu Glu Trp Ile Gly
                35                  40                  45
Ala Ile Asn Ala Asp Ser Asp Asn Thr Trp Tyr Pro Ser Trp Val Lys
        50                  55                  60
Gly Arg Phe Thr Ile Ser Lys Thr Ser Ser Thr Thr Val Asp Leu Lys
65                  70                  75                  80
Ile Thr Ser Pro Thr Ile Glu Asp Thr Ala Thr Tyr Phe Cys Ala Arg
                85                  90                  95
Ser Val Ser Asn Asn Phe Ala Glu Tyr Asn Ile Trp Gly Pro Gly Thr
                100                 105                 110
Leu Val Thr Val Ser Ser
        115
```

<210> SEQ ID NO 9
<211> LENGTH: 660
<212> TYPE: DNA
<213> ORGANISM: Artificial Sequence
<220> FEATURE:
<223> OTHER INFORMATION: synthesized

<400> SEQUENCE: 9

```
caagccgtgg tgacccagac tccatcgtcc gtgtctgcag ctgtgggagg cacagtcacc      60
atcagttgcc agtccagtca gagtgtttat aacaacaacg acttagcctg gtatcagcag     120
aaaccagggc agcctcccaa gctcctgatc tactatgcat ccactctggc atctggggtc     180
tcatcgcggt tcaaaggcag tggatctggg acacagttca ctctcgccat cagcgacctg     240
gagtgtgacg attctgccac ttactactgt gcaggcggtt atgatacgga tggtcttgat     300
```

```
acgtttgctt tcggcggagg caccgaggtg gaggtcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600 gaagtcaccc atcagggcct gagctcgccc gtcacaaaga gcttcaacag gggagagtgt    660
```

<210> SEQ ID NO 10
<211> LENGTH: 339
<212> TYPE: DNA
<213> ORGANISM: Artificial Sequence
<220> FEATURE:
<223> OTHER INFORMATION: synthesized

<400> SEQUENCE: 10

```
caagccgtgg tgacccagac tccatcgtcc gtgtctgcag ctgtgggagg cacagtcacc     60
atcagttgcc agtccagtca gagtgtttat aacaacaacg acttagcctg gtatcagcag    120
aaaccagggc agcctcccaa gctcctgatc tactatgcat ccactctggc atctggggtc    180
tcatcgcggt tcaaaggcag tggatctggg acacagttca ctctcgccat cagcgacctg    240
gagtgtgacg attctgccac ttactactgt gcaggcggtt atgatacgga tggtcttgat    300
acgtttgctt tcggcggagg caccgaggtg gaggtcaaa                           339
```

<210> SEQ ID NO 11
<211> LENGTH: 220
<212> TYPE: PRT
<213> ORGANISM: Artificial Sequence
<220> FEATURE:
<223> OTHER INFORMATION: synthesized

<400> SEQUENCE: 11

Gln Ala Val Val Thr Gln Thr Pro Ser Ser Val Ser Ala Ala Val Gly
1               5                   10                  15

Gly Thr Val Thr Ile Ser Cys Gln Ser Ser Gln Ser Val Tyr Asn Asn
            20                  25                  30

Asn Asp Leu Ala Trp Tyr Gln Gln Lys Pro Gly Gln Pro Pro Lys Leu
        35                  40                  45

Leu Ile Tyr Tyr Ala Ser Thr Leu Ala Ser Gly Val Ser Ser Arg Phe
    50                  55                  60

Lys Gly Ser Gly Ser Gly Thr Gln Phe Thr Leu Ala Ile Ser Asp Leu
65                  70                  75                  80

Glu Cys Asp Asp Ser Ala Thr Tyr Tyr Cys Ala Gly Gly Tyr Asp Thr
                85                  90                  95

Asp Gly Leu Asp Thr Phe Ala Phe Gly Gly Gly Thr Glu Val Glu Val
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr

```
                 180                 185                 190
Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 12
<211> LENGTH: 113
<212> TYPE: PRT
<213> ORGANISM: Artificial Sequence
<220> FEATURE:
<223> OTHER INFORMATION: synthesized

<400> SEQUENCE: 12

Gln Ala Val Val Thr Gln Thr Pro Ser Ser Val Ser Ala Ala Val Gly
1               5                   10                  15

Gly Thr Val Thr Ile Ser Cys Gln Ser Ser Gln Ser Val Tyr Asn Asn
            20                  25                  30

Asn Asp Leu Ala Trp Tyr Gln Gln Lys Pro Gly Gln Pro Pro Lys Leu
        35                  40                  45

Leu Ile Tyr Tyr Ala Ser Thr Leu Ala Ser Gly Val Ser Ser Arg Phe
    50                  55                  60

Lys Gly Ser Gly Ser Gly Thr Gln Phe Thr Leu Ala Ile Ser Asp Leu
65                  70                  75                  80

Glu Cys Asp Asp Ser Ala Thr Tyr Tyr Cys Ala Gly Gly Tyr Asp Thr
                85                  90                  95

Asp Gly Leu Asp Thr Phe Ala Phe Gly Gly Gly Thr Glu Val Glu Val
            100                 105                 110

Lys
```

```
<210> SEQ ID NO 13
<211> LENGTH: 1347
<212> TYPE: DNA
<213> ORGANISM: Artificial Sequence
<220> FEATURE:
<223> OTHER INFORMATION: synthesized

<400> SEQUENCE: 13
caggagcagc tgaaggagtc cggaggaggc ctggtaacgc ctggaggaac cctgacactc      60
acctgcacag cctctggatt caccatcagt cgctaccaca tgacttgggt ccgccaggct     120
ccagggaagg ggctggagtg gatcggtcat atttatgtta ataatgatga cacagactac     180
gcgagctggg cgaaaggccg attcaccatc tccaaaacct cgaccacggt ggatctgaag     240
atcaccagtc cgacaaccga ggacacggcc acctatttct gtgccagatt ggatgttggt     300
ggtggtggtg cttatattgg ggacatctgg ggccaaggga ccctggtcac cgtctcgagc     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaagc cgcgggggca     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
```

```
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcgcggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc tccgggt                                       1347
```

<210> SEQ ID NO 14
<211> LENGTH: 360
<212> TYPE: DNA
<213> ORGANISM: Artificial Sequence
<220> FEATURE:
<223> OTHER INFORMATION: synthesized

<400> SEQUENCE: 14

```
caggagcagc tgaaggagtc cggaggaggc ctggtaacgc ctggaggaac cctgacactc     60
acctgcacag cctctggatt caccatcagt cgctaccaca tgacttgggt ccgccaggct    120
ccagggaagg ggctggagtg gatcggtcat atttatgtta ataatgatga cacagactac    180
gcgagctggg cgaaaggccg attcaccatc tccaaaacct cgaccacggt ggatctgaag    240
atcaccagtc cgacaaccga ggacacggcc acctatttct gtgccagatt ggatgttggt    300
ggtggtggtg cttatattgg ggacatctgg ggccaaggga ccctggtcac cgtctcgagc    360
```

<210> SEQ ID NO 15
<211> LENGTH: 449
<212> TYPE: PRT
<213> ORGANISM: Artificial Sequence
<220> FEATURE:
<223> OTHER INFORMATION: synthesized

<400> SEQUENCE: 15

```
Gln Glu Gln Leu Lys Glu Ser Gly Gly Gly Leu Val Thr Pro Gly Gly
1               5                   10                  15

Thr Leu Thr Leu Thr Cys Thr Ala Ser Gly Phe Thr Ile Ser Arg Tyr
            20                  25                  30

His Met Thr Trp Val Arg Gln Ala Pro Gly Lys Gly Leu Glu Trp Ile
        35                  40                  45

Gly His Ile Tyr Val Asn Asn Asp Asp Thr Asp Tyr Ala Ser Trp Ala
    50                  55                  60

Lys Gly Arg Phe Thr Ile Ser Lys Thr Ser Thr Thr Val Asp Leu Lys
65                  70                  75                  80

Ile Thr Ser Pro Thr Thr Glu Asp Thr Ala Thr Tyr Phe Cys Ala Arg
                85                  90                  95

Leu Asp Val Gly Gly Gly Gly Ala Tyr Ile Gly Asp Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 16
<211> LENGTH: 120
<212> TYPE: PRT
<213> ORGANISM: Artificial Sequence
<220> FEATURE:
<223> OTHER INFORMATION: synthesized

<400> SEQUENCE: 16

Gln Glu Gln Leu Lys Glu Ser Gly Gly Gly Leu Val Thr Pro Gly Gly
1               5                   10                  15

Thr Leu Thr Leu Thr Cys Thr Ala Ser Gly Phe Thr Ile Ser Arg Tyr
            20                  25                  30

His Met Thr Trp Val Arg Gln Ala Pro Gly Lys Gly Leu Glu Trp Ile
            35                  40                  45

Gly His Ile Tyr Val Asn Asn Asp Asp Thr Asp Tyr Ala Ser Trp Ala
        50                  55                  60

```
Lys Gly Arg Phe Thr Ile Ser Lys Thr Ser Thr Val Asp Leu Lys
 65                  70                  75                  80

Ile Thr Ser Pro Thr Thr Glu Asp Thr Ala Thr Tyr Phe Cys Ala Arg
                 85                  90                  95

Leu Asp Val Gly Gly Gly Ala Tyr Ile Gly Asp Ile Trp Gly Gln
            100                 105                 110

Gly Thr Leu Val Thr Val Ser Ser
            115                 120
```

<210> SEQ ID NO 17
<211> LENGTH: 657
<212> TYPE: DNA
<213> ORGANISM: Artificial Sequence
<220> FEATURE:
<223> OTHER INFORMATION: synthesized

<400> SEQUENCE: 17

| | | | | | |
|---|---|---|---|---|---|
| gacattgtga | tgacccagac | tccagcctct | gtggaggtcg | ctgtgggagg | cacagtcacc | 60 |
| atcaagtgcc | aggccagtca | gaacattggt | agtgattag | cctggtatca | gcagaaacca | 120 |
| gggcagcctc | ccaagctcct | gatctatact | acatccaatc | tggcatctgg | ggtcccatcg | 180 |
| cggttcaaag | gcagtggatc | tgggacaggt | ttcactctca | ccatcagcga | cctggagtgt | 240 |
| gccgatgctg | ccagttactg | ctgtcaaggc | ggttatttta | gtggtcgtaa | tatttatggg | 300 |
| aatgctttcg | gcggaggcac | cgaggtggtg | gtcaaacgta | cggtggctgc | accatctgtc | 360 |
| ttcatcttcc | cgccatctga | tgagcagttg | aaatctggaa | ctgcctctgt | tgtgtgcctg | 420 |
| ctgaataact | tctatcccag | agaggccaaa | gtacagtgga | aggtggataa | cgccctccaa | 480 |
| tcgggtaact | cccaggagag | tgtcacagag | caggacagca | aggacagcac | ctacagcctc | 540 |
| agcagcaccc | tgacgctgag | caaagcagac | tacgagaaac | acaaagtcta | cgcctgcgaa | 600 |
| gtcacccatc | agggcctgag | ctcgcccgtc | acaaagagct | tcaacagggg | agagtgt | 657 |

<210> SEQ ID NO 18
<211> LENGTH: 336
<212> TYPE: DNA
<213> ORGANISM: Artificial Sequence
<220> FEATURE:
<223> OTHER INFORMATION: synthesized

<400> SEQUENCE: 18

| | | | | | |
|---|---|---|---|---|---|
| gacattgtga | tgacccagac | tccagcctct | gtggaggtcg | ctgtgggagg | cacagtcacc | 60 |
| atcaagtgcc | aggccagtca | gaacattggt | agtgatttag | cctggtatca | gcagaaacca | 120 |
| gggcagcctc | ccaagctcct | gatctatact | acatccaatc | tggcatctgg | ggtcccatcg | 180 |
| cggttcaaag | gcagtggatc | tgggacaggt | ttcactctca | ccatcagcga | cctggagtgt | 240 |
| gccgatgctg | ccagttactg | ctgtcaaggc | ggttatttta | gtggtcgtaa | tatttatggg | 300 |
| aatgctttcg | gcggaggcac | cgaggtggtg | gtcaaa | | | 336 |

<210> SEQ ID NO 19
<211> LENGTH: 219
<212> TYPE: PRT
<213> ORGANISM: Artificial Sequence
<220> FEATURE:
<223> OTHER INFORMATION: synthesized

<400> SEQUENCE: 19

```
Asp Ile Val Met Thr Gln Thr Pro Ala Ser Val Glu Val Ala Val Gly
 1               5                  10                  15
```

```
Gly Thr Val Thr Ile Lys Cys Gln Ala Ser Gln Asn Ile Gly Ser Asp
            20                  25                  30

Leu Ala Trp Tyr Gln Gln Lys Pro Gly Gln Pro Pro Lys Leu Leu Ile
            35                  40                  45

Tyr Thr Thr Ser Asn Leu Ala Ser Gly Val Pro Ser Arg Phe Lys Gly
 50                  55                  60

Ser Gly Ser Gly Thr Gly Phe Thr Leu Thr Ile Ser Asp Leu Glu Cys
 65                  70                  75                  80

Ala Asp Ala Ala Ser Tyr Cys Cys Gln Gly Gly Tyr Phe Ser Gly Arg
                 85                  90                  95

Asn Ile Tyr Gly Asn Ala Phe Gly Gly Gly Thr Glu Val Val Val Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 20
<211> LENGTH: 112
<212> TYPE: PRT
<213> ORGANISM: Artificial Sequence
<220> FEATURE:
<223> OTHER INFORMATION: synthesized

<400> SEQUENCE: 20

Asp Ile Val Met Thr Gln Thr Pro Ala Ser Val Glu Val Ala Val Gly
1               5                   10                  15

Gly Thr Val Thr Ile Lys Cys Gln Ala Ser Gln Asn Ile Gly Ser Asp
            20                  25                  30

Leu Ala Trp Tyr Gln Gln Lys Pro Gly Gln Pro Pro Lys Leu Leu Ile
            35                  40                  45

Tyr Thr Thr Ser Asn Leu Ala Ser Gly Val Pro Ser Arg Phe Lys Gly
 50                  55                  60

Ser Gly Ser Gly Thr Gly Phe Thr Leu Thr Ile Ser Asp Leu Glu Cys
 65                  70                  75                  80

Ala Asp Ala Ala Ser Tyr Cys Cys Gln Gly Gly Tyr Phe Ser Gly Arg
                 85                  90                  95

Asn Ile Tyr Gly Asn Ala Phe Gly Gly Gly Thr Glu Val Val Val Lys
            100                 105                 110

<210> SEQ ID NO 21
<211> LENGTH: 1323
<212> TYPE: DNA
<213> ORGANISM: Artificial Sequence
<220> FEATURE:
<223> OTHER INFORMATION: synthesized

<400> SEQUENCE: 21
```

```
cagtcggtgg aggagtccgg gggtcgcctg gtcacgcctg ggacacccct gacactcacc      60
tgcacagtct ctggattctc cctcagtggc gctggagtga gctgggtccg ccaggctcca     120
gggaaggggc tggagtggat cggatacatt gatagtggtg ctaccacata ctacgcgagc     180
tgggcaaaag gccgattcac catctccaaa gcctcgacca cggtggatct gaaaatcgcc     240
agtccgacaa ccgaggacac ggccacctat ttctgtgcca gaggatacta cggcatggac     300 ccctgggggcc aaggcaccct ggtcaccgtc tcgagcgcta gcaccaaggg cccatcggtc     360
ttccccctgg caccctcctc caagagcacc tctggggggca gcggccctg ggctgcctg      420 gtcaaggact acttccccga accggtgacg gtgtcgtgga actcaggcgc cctgaccagc     480
ggcgtgcaca ccttcccggc tgtcctacag tcctcaggac tctactccct cagcagcgtg     540
gtgaccgtgc cctccagcag cttgggcacc cagacctaca tctgcaacgt gaatcacaag     600
cccagcaaca ccaaggtgga caagagagtt gagcccaaat cttgtgacaa aactcacaca     660
tgcccaccgt gcccagcacc tgaagccgcg gggcaccgt cagtcttcct cttcccccca     720
aaacccaagg acaccctcat gatctcccgg acccctgagg tcacatgcgt ggtggtggac     780
gtgagccacg aagaccctga ggtcaagttc aactggtacg tggacggcgt ggaggtgcat     840
aatgccaaga caaagccgcg ggaggagcag tacaacagca cgtaccgtgt ggtcagcgtc     900
ctcaccgtcc tgcaccagga ctggctgaat ggcaaggagt acaagtgcgc ggtctccaac     960
aaagccctcc cagcccccat cgagaaaacc atctccaaag ccaagggca gccccgagaa    1020 ccacaggtgt acaccctgcc cccatcccgg gatgagctga ccaagaacca ggtcagcctg    1080
acctgcctgg tcaaaggctt ctatcccagc gacatcgccg tggagtggga gagcaatggg    1140
cagccggaga caactacaa gaccacgcct cccgtgctgg actccgacgg ctccttcttc     1200
ctctatagca agctcaccgt ggacaagagc aggtggcagc aggggaacgt cttctcatgc    1260
tccgtgatgc atgaggctct gcacaaccac tacacgcaga agagcctctc cctgtctccg    1320
ggt                                                                  1323

<210> SEQ ID NO 22
<211> LENGTH: 336
<212> TYPE: DNA
<213> ORGANISM: Artificial Sequence
<220> FEATURE:
<223> OTHER INFORMATION: synthesized

<400> SEQUENCE: 22
cagtcggtgg aggagtccgg gggtcgcctg gtcacgcctg ggacacccct gacactcacc      60
tgcacagtct ctggattctc cctcagtggc gctggagtga gctgggtccg ccaggctcca     120
gggaaggggc tggagtggat cggatacatt gatagtggtg ctaccacata ctacgcgagc     180
tgggcaaaag gccgattcac catctccaaa gcctcgacca cggtggatct gaaaatcgcc     240
agtccgacaa ccgaggacac ggccacctat ttctgtgcca gaggatacta cggcatggac     300
ccctggggcc aaggcaccct ggtcaccgtc tcgagc                              336

<210> SEQ ID NO 23
<211> LENGTH: 441
<212> TYPE: PRT
<213> ORGANISM: Artificial Sequence
<220> FEATURE:
<223> OTHER INFORMATION: synthesized

<400> SEQUENCE: 23
```

```
Gln Ser Val Glu Glu Ser Gly Gly Arg Leu Val Thr Pro Gly Thr Pro
  1               5                  10                 15

Leu Thr Leu Thr Cys Thr Val Ser Gly Phe Ser Leu Ser Gly Ala Gly
             20                  25                  30

Val Ser Trp Val Arg Gln Ala Pro Gly Lys Gly Leu Glu Trp Ile Gly
         35                  40                  45

Tyr Ile Asp Ser Gly Ala Thr Thr Tyr Tyr Ala Ser Trp Ala Lys Gly
     50                  55                  60

Arg Phe Thr Ile Ser Lys Ala Ser Thr Thr Val Asp Leu Lys Ile Ala
 65                  70                  75                  80

Ser Pro Thr Thr Glu Asp Thr Ala Thr Tyr Phe Cys Ala Arg Gly Tyr
                 85                  90                  95

Tyr Gly Met Asp Pro Trp Gly Gln Gly Thr Leu Val Thr Val Ser Ser
             100                 105                 110

Ala Ser Thr Lys Gly Pro Ser Val Phe Pro Leu Ala Pro Ser Ser Lys
             115                 120                 125

Ser Thr Ser Gly Gly Thr Ala Ala Leu Gly Cys Leu Val Lys Asp Tyr
         130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
             165                 170                 175

Leu Ser Ser Val Val Thr Val Pro Ser Ser Leu Gly Thr Gln Thr
             180                 185                 190

Tyr Ile Cys Asn Val Asn His Lys Pro Ser Asn Thr Lys Val Asp Lys
     195                 200                 205

Arg Val Glu Pro Lys Ser Cys Asp Lys Thr His Thr Cys Pro Pro Cys
     210                 215                 220

Pro Ala Pro Glu Ala Ala Gly Ala Pro Ser Val Phe Leu Phe Pro Pro
225                 230                 235                 240

Lys Pro Lys Asp Thr Leu Met Ile Ser Arg Thr Pro Glu Val Thr Cys
                 245                 250                 255

Val Val Val Asp Val Ser His Glu Asp Pro Glu Val Lys Phe Asn Trp
             260                 265                 270

Tyr Val Asp Gly Val Glu Val His Asn Ala Lys Thr Lys Pro Arg Glu
     275                 280                 285

Glu Gln Tyr Asn Ser Thr Tyr Arg Val Val Ser Val Leu Thr Val Leu
     290                 295                 300

His Gln Asp Trp Leu Asn Gly Lys Glu Tyr Lys Cys Ala Val Ser Asn
305                 310                 315                 320

Lys Ala Leu Pro Ala Pro Ile Glu Lys Thr Ile Ser Lys Ala Lys Gly
             325                 330                 335

Gln Pro Arg Glu Pro Gln Val Tyr Thr Leu Pro Pro Ser Arg Asp Glu
             340                 345                 350

Leu Thr Lys Asn Gln Val Ser Leu Thr Cys Leu Val Lys Gly Phe Tyr
             355                 360                 365

Pro Ser Asp Ile Ala Val Glu Trp Glu Ser Asn Gly Gln Pro Glu Asn
             370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                 405                 410                 415

Val Phe Ser Cys Ser Val Met His Glu Ala Leu His Asn His Tyr Thr
```

Gln Lys Ser Leu Ser Leu Ser Pro Gly
    435                 440

<210> SEQ ID NO 24
<211> LENGTH: 112
<212> TYPE: PRT
<213> ORGANISM: Artificial Sequence
<220> FEATURE:
<223> OTHER INFORMATION: synthesized

<400> SEQUENCE: 24

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Gly Ala Gly
            20                  25                  30

Val Ser Trp Val Arg Gln Ala Pro Gly Lys Gly Leu Glu Trp Ile Gly
        35                  40                  45

Tyr Ile Asp Ser Gly Ala Thr Thr Tyr Tyr Ala Ser Trp Ala Lys Gly
    50                  55                  60

Arg Phe Thr Ile Ser Lys Ala Ser Thr Thr Val Asp Leu Lys Ile Ala
65                  70                  75                  80

Ser Pro Thr Thr Glu Asp Thr Ala Thr Tyr Phe Cys Ala Arg Gly Tyr
                85                  90                  95

Tyr Gly Met Asp Pro Trp Gly Gln Gly Thr Leu Val Thr Val Ser Ser
            100                 105                 110

<210> SEQ ID NO 25
<211> LENGTH: 657
<212> TYPE: DNA
<213> ORGANISM: Artificial Sequence
<220> FEATURE:
<223> OTHER INFORMATION: synthesized

<400> SEQUENCE: 25
gccatcgatt tgacccagac tccagcctcc gtggaggcag ctgtgggagg cacaatcacc     60
atcaattgcc aagccagtga gagcattagc agttggttag cctggtatca gcagaaacca    120
gggcagcgtc ccaagctcct gatctacgaa acatccaaac tggcatctgg ggtcccaccg    180
cggttcagcg gcagtggatc tgggacacag ttcactctca ccatcagcgg cgtgcagtgt    240
gacgatgctg ccacttacta ctgtcaaagt tattatcgta ttaataatat tggttacgat    300
aatgctttcg gcggaggcac cgaggtggag ttcaaacgta cggtggctgc accatctgtc    360
ttcatcttcc cgccatctga tgagcagttg aaatctggaa ctgcctctgt tgtgtgcctg    420
ctgaataact ctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt       657

<210> SEQ ID NO 26
<211> LENGTH: 336
<212> TYPE: DNA
<213> ORGANISM: Artificial Sequence
<220> FEATURE:
<223> OTHER INFORMATION: synthesized

<400> SEQUENCE: 26
gccatcgatt tgacccagac tccagcctcc gtggaggcag ctgtgggagg cacaatcacc     60

```
atcaattgcc aagccagtga gagcattagc agttggttag cctggtatca gcagaaacca    120
gggcagcgtc ccaagctcct gatctacgaa acatccaaac tggcatctgg ggtcccaccg    180
cggttcagcg gcagtggatc tgggacacag ttcactctca ccatcagcgg cgtgcagtgt    240
gacgatgctg ccacttacta ctgtcaaagt tattatcgta ttaataatat tggttacgat    300
aatgctttcg gcggaggcac cgaggtggag ttcaaa                              336
```

<210> SEQ ID NO 27
<211> LENGTH: 219
<212> TYPE: PRT
<213> ORGANISM: Artificial Sequence
<220> FEATURE:
<223> OTHER INFORMATION: synthesized

<400> SEQUENCE: 27

```
Ala Ile Asp Leu Thr Gln Thr Pro Ala Ser Val Glu Ala Ala Val Gly
1               5                   10                  15

Gly Thr Ile Thr Ile Asn Cys Gln Ala Ser Glu Ser Ile Ser Ser Trp
            20                  25                  30

Leu Ala Trp Tyr Gln Gln Lys Pro Gly Gln Arg Pro Lys Leu Leu Ile
        35                  40                  45

Tyr Glu Thr Ser Lys Leu Ala Ser Gly Val Pro Pro Arg Phe Ser Gly
    50                  55                  60

Ser Gly Ser Gly Thr Gln Phe Thr Leu Thr Ile Ser Gly Val Gln Cys
65                  70                  75                  80

Asp Asp Ala Ala Thr Tyr Tyr Cys Gln Ser Tyr Tyr Arg Ile Asn Asn
                85                  90                  95

Ile Gly Tyr Asp Asn Ala Phe Gly Gly Gly Thr Glu Val Glu Phe Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 28
<211> LENGTH: 112
<212> TYPE: PRT
<213> ORGANISM: Artificial Sequence
<220> FEATURE:
<223> OTHER INFORMATION: synthesized

<400> SEQUENCE: 28

```
Ala Ile Asp Leu Thr Gln Thr Pro Ala Ser Val Glu Ala Ala Val Gly
1               5                   10                  15

Gly Thr Ile Thr Ile Asn Cys Gln Ala Ser Glu Ser Ile Ser Ser Trp
            20                  25                  30
```

```
Leu Ala Trp Tyr Gln Gln Lys Pro Gly Gln Arg Pro Lys Leu Leu Ile
             35                  40                  45
Tyr Glu Thr Ser Lys Leu Ala Ser Gly Val Pro Pro Arg Phe Ser Gly
         50                  55                  60
Ser Gly Ser Gly Thr Gln Phe Thr Leu Thr Ile Ser Gly Val Gln Cys
65                  70                  75                  80
Asp Asp Ala Ala Thr Tyr Tyr Cys Gln Ser Tyr Tyr Arg Ile Asn Asn
                 85                  90                  95
Ile Gly Tyr Asp Asn Ala Phe Gly Gly Gly Thr Glu Val Glu Phe Lys
            100                 105                 110
```

<210> SEQ ID NO 29
<211> LENGTH: 1326
<212> TYPE: DNA
<213> ORGANISM: Artificial Sequence
<220> FEATURE:
<223> OTHER INFORMATION: synthesized

<400> SEQUENCE: 29

| | | |
|---|---|---|
| cagtcggtgg aggagtccgg gggtcgcctg gtcacgcctg ggacacccct gacactcacc | 60 |
| tgcaccgtct ctggattctc cctcagtagg aatgcaatga actgggtccg ccaggctcca | 120 |
| gggaaggggc tggaatacat cggatacatt agcactagtg gtaccacatt ctacgcgaac | 180 |
| tgggtgaaag gccgattcac catctccaaa acctcgacca cggtggatct gaaaatgacc | 240 |
| agtctgacaa ccgaggacac ggccacctat ttctgtgcca gagactataa ctacgccatg | 300 |
| gacatctggg gccaaggcac cctggtcacc gtctcgagcg ctagcaccaa gggcccatcg | 360 |
| gtcttccccc tggcaccctc ctccaagagc acctctgggg gcacagcggc cctgggctgc | 420 |
| ctggtcaagg actacttccc cgaaccggtg acggtgtcgt ggaactcagg cgccctgacc | 480 |
| agcggcgtgc acaccttccc ggctgtccta cagtcctcag gactctactc cctcagcagc | 540 |
| gtggtgaccg tgccctccag cagcttgggc acccagacct acatctgcaa cgtgaatcac | 600 |
| aagcccagca acaccaaggt ggacaagaga gttgagccca atcttgtga caaaactcac | 660 |
| acatgcccac cgtgcccagc acctgaagcc gcggggggca cgtcagtctt cctcttcccc | 720 |
| ccaaaaccca aggacaccct catgatctcc cggacccctg aggtcacatg cgtggtggtg | 780 |
| gacgtgagcc acgaagaccc tgaggtcaag ttcaactggt acgtggacgg cgtggaggtg | 840 |
| cataatgcca agacaaagcc gcgggaggag cagtacaaca gcacgtaccg tgtggtcagc | 900 |
| gtcctcaccg tcctgcacca ggactggctg aatggcaagg agtacaagtg cgcggtctcc | 960 |
| aacaaagccc tcccagcccc catcgagaaa accatctcca aagccaaagg gcagccccga | 1020 |
| gaaccacagg tgtacaccct gcccccatcc cgggatgagc tgaccaagaa ccaggtcagc | 1080 |
| ctgacctgcc tggtcaaagg cttctatccc agcgacatcg ccgtggagtg ggagagcaat | 1140 |
| gggcagccgg agaacaacta caagaccacg cctcccgtgc tggactccga cggctccttc | 1200 |
| ttcctctata gcaagctcac cgtggacaag agcaggtggc agcaggggaa cgtcttctca | 1260 |
| tgctccgtga tgcatgaggc tctgcacaac cactacacgc agaagagcct ctccctgtct | 1320 |
| ccgggt | 1326 |

<210> SEQ ID NO 30
<211> LENGTH: 339
<212> TYPE: DNA
<213> ORGANISM: Artificial Sequence
<220> FEATURE:
<223> OTHER INFORMATION: synthesized

<400> SEQUENCE: 30

```
cagtcggtgg aggagtccgg gggtcgcctg gtcacgcctg ggacacccct gacactcacc    60
tgcaccgtct ctggattctc cctcagtagg aatgcaatga actgggtccg ccaggctcca   120
gggaaggggc tggaatacat cggatacatt agcactagtg gtaccacatt ctacgcgaac   180
tgggtgaaag gccgattcac catctccaaa acctcgacca cggtggatct gaaaatgacc   240
agtctgacaa ccgaggacac ggccacctat ttctgtgcca gagactataa ctacgccatg   300
gacatctggg gccaaggcac cctggtcacc gtctcgagc                           339
```

<210> SEQ ID NO 31
<211> LENGTH: 442
<212> TYPE: PRT
<213> ORGANISM: Artificial Sequence
<220> FEATURE:
<223> OTHER INFORMATION: synthesized

<400> SEQUENCE: 31

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Arg Asn Ala
            20                  25                  30

Met Asn Trp Val Arg Gln Ala Pro Gly Lys Gly Leu Glu Tyr Ile Gly
        35                  40                  45

Tyr Ile Ser Thr Ser Gly Thr Thr Phe Tyr Ala Asn Trp Val Lys Gly
    50                  55                  60

Arg Phe Thr Ile Ser Lys Thr Ser Thr Val Asp Leu Lys Met Thr
65                  70                  75                  80

Ser Leu Thr Thr Glu Asp Thr Ala Thr Tyr Phe Cys Ala Arg Asp Tyr
                85                  90                  95

Asn Tyr Ala Met Asp Ile Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Ala Ala Gly Ala Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
```

```
                    290                 295                 300
Leu His Gln Asp Trp Leu Asn Gly Lys Glu Tyr Lys Cys Ala Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
                340                 345                 350

Glu Leu Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly
            435                 440

<210> SEQ ID NO 32
<211> LENGTH: 113
<212> TYPE: PRT
<213> ORGANISM: Artificial Sequence
<220> FEATURE:
<223> OTHER INFORMATION: synthesized

<400> SEQUENCE: 32

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Arg Asn Ala
                20                  25                  30

Met Asn Trp Val Arg Gln Ala Pro Gly Lys Gly Leu Glu Tyr Ile Gly
            35                  40                  45

Tyr Ile Ser Thr Ser Gly Thr Thr Phe Tyr Ala Asn Trp Val Lys Gly
    50                  55                  60

Arg Phe Thr Ile Ser Lys Thr Ser Thr Val Asp Leu Lys Met Thr
65                  70                  75                  80

Ser Leu Thr Thr Glu Asp Thr Ala Thr Tyr Phe Cys Ala Arg Asp Tyr
                85                  90                  95

Asn Tyr Ala Met Asp Ile Trp Gly Gln Gly Thr Leu Val Thr Val Ser
                100                 105                 110

Ser

<210> SEQ ID NO 33
<211> LENGTH: 648
<212> TYPE: DNA
<213> ORGANISM: Artificial Sequence
<220> FEATURE:
<223> OTHER INFORMATION: synthesized

<400> SEQUENCE: 33
gctcaagtgc tgacccagac tccatcctcc gtgtctgcag ctgtgggagg cacagtcacc      60
atcaattgcc agtccagtca gagtgttaat aacaacgact tagcctggtt tcagcagaaa    120
ccagggcagc ctcccaagcg cctgatctac tgggcatcca aactggcatc tggggtccca    180
tcgcggttca aaggcagtgg atctgggaca cagttcattc tcaccatcag cgacctggag    240
```

-continued

```
tgtgacgatg ctgccactta ctactgtgca ggcggttata gtggtaatat ttatggtttc    300
ggcggaggca ccgaggtgga ggtcaaacgt acggtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata cgccctcca atcgggtaac     480 tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt                 648
```

<210> SEQ ID NO 34
<211> LENGTH: 327
<212> TYPE: DNA
<213> ORGANISM: Artificial Sequence
<220> FEATURE:
<223> OTHER INFORMATION: synthesized

<400> SEQUENCE: 34

```
gctcaagtgc tgacccagac tccatcctcc gtgtctgcag ctgtgggagg cacagtcacc     60
atcaattgcc agtccagtca gagtgttaat aacaacgact tagcctggtt tcagcagaaa    120
ccagggcagc ctcccaagcg cctgatctac tgggcatcca aactggcatc tggggtccca    180
tcgcggttca aaggcagtgg atctgggaca cagttcattc tcaccatcag cgacctggag    240
tgtgacgatg ctgccactta ctactgtgca ggcggttata gtggtaatat ttatggtttc    300
ggcggaggca ccgaggtgga ggtcaaa                                        327
```

<210> SEQ ID NO 35
<211> LENGTH: 216
<212> TYPE: PRT
<213> ORGANISM: Artificial Sequence
<220> FEATURE:
<223> OTHER INFORMATION: synthesized

<400> SEQUENCE: 35

```
Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Asn Asn Asn
            20                  25                  30

Asp Leu Ala Trp Phe Gln Gln Lys Pro Gly Pro Pro Lys Arg Leu
        35                  40                  45

Ile Tyr Trp Ala Ser Lys Leu Ala Ser Gly Val Pro Ser Arg Phe Lys
50                  55                  60

Gly Ser Gly Ser Gly Thr Gln Phe Ile Leu Thr Ile Ser Asp Leu Glu
65                  70                  75                  80

Cys Asp Asp Ala Ala Thr Tyr Tyr Cys Ala Gly Gly Tyr Ser Gly Asn
                85                  90                  95

Ile Tyr Gly Phe Gly Gly Gly Thr Glu Val Glu Val Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175
```

```
Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 36
<211> LENGTH: 109
<212> TYPE: PRT
<213> ORGANISM: Artificial Sequence
<220> FEATURE:
<223> OTHER INFORMATION: synthesized

<400> SEQUENCE: 36

Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Asn Asn Asn
            20                  25                  30

Asp Leu Ala Trp Phe Gln Gln Lys Pro Gly Gln Pro Pro Lys Arg Leu
        35                  40                  45

Ile Tyr Trp Ala Ser Lys Leu Ala Ser Gly Val Pro Ser Arg Phe Lys
    50                  55                  60

Gly Ser Gly Ser Gly Thr Gln Phe Ile Leu Thr Ile Ser Asp Leu Glu
65                  70                  75                  80

Cys Asp Asp Ala Ala Thr Tyr Tyr Cys Ala Gly Gly Tyr Ser Gly Asn
                85                  90                  95

Ile Tyr Gly Phe Gly Gly Gly Thr Glu Val Glu Val Lys
            100                 105

<210> SEQ ID NO 37
<211> LENGTH: 1317
<212> TYPE: DNA
<213> ORGANISM: Artificial Sequence
<220> FEATURE:
<223> OTHER INFORMATION: synthesized

<400> SEQUENCE: 37
cagtcggtgg aggagtccgg gggtcgcctg gtcacgcctg gacacccct gacactcacc      60 tgcaccgtct ctggattctc cctcagtaac aatgcaataa cctgggtccg ccaggctcca    120 gggaagggc tggaatacat cggaatcatt agtagtagtg gtaccacata ctacgcgagc     180
tgggcgaaag gccgattcac catctccaaa acctcgtcga ccacggtgga tctgaaaatg    240
accagtctga aaccgagga cacggccacc tatttctgtg ccggagcatt agcgtctgg     300 ggcccgggca cctcgtcac cgtctcgagc gctagcacca agggcccatc ggtcttcccc     360
ctggcaccct cctccaagag cacctctggg ggcacagcgg ccctgggctg cctggtcaag    420
gactacttcc ccgaaccggt gacggtgtcg tggaactcag cgccctgac cagcggcgtg     480 cacaccttcc cggctgtcct acagtcctca ggactctact ccctcagcag cgtggtgacc    540
gtgccctcca gcagcttggg cacccagacc tacatctgca acgtgaatca caagcccagc    600
aacaccaagg tggacaagag agttgagccc aaatcttgtg acaaaactca cacatgccca    660
ccgtgcccag cacctgaagc cgcggggca ccgtcagtct tcctcttccc cccaaaaccc     720
aaggacaccc tcatgatctc ccggaccct gaggtcacat gcgtggtggt ggacgtgagc     780
cacgaagacc ctgaggtcaa gttcaactgg tacgtggacg gcgtggaggt gcataatgcc    840
```

```
aagacaaagc cgcgggagga gcagtacaac agcacgtacc gtgtggtcag cgtcctcacc    900
gtcctgcacc aggactggct gaatggcaag gagtacaagt gcgcggtctc caacaaagcc    960
ctcccagccc ccatcgagaa aaccatctcc aaagccaaag ggcagccccg agaaccacag   1020
gtgtacaccc tgcccccatc ccgggatgag ctgaccaaga accaggtcag cctgacctgc   1080
ctggtcaaag gcttctatcc cagcgacatc gccgtggagt gggagagcaa tgggcagccg   1140
gagaacaact acaagaccac gcctcccgtg ctggactccg acggctcctt cttcctctat   1200
agcaagctca ccgtggacaa gagcaggtgg cagcagggga acgtcttctc atgctccgtg   1260
atgcatgagg ctctgcacaa ccactacacg cagaagagcc tctccctgtc tccgggt     1317
```

<210> SEQ ID NO 38
<211> LENGTH: 330
<212> TYPE: DNA
<213> ORGANISM: Artificial Sequence
<220> FEATURE:
<223> OTHER INFORMATION: synthesized

<400> SEQUENCE: 38

```
cagtcggtgg aggagtccgg gggtcgcctg gtcacgcctg ggacacccct gacactcacc     60
tgcaccgtct ctggattctc cctcagtaac aatgcaataa cctgggtccg ccaggctcca    120
gggaaggggc tggaatacat cggaatcatt agtagtagtg gtaccacata ctacgcgagc    180
tgggcgaaag gccgattcac catctccaaa acctcgtcga ccacggtgga tctgaaaatg    240
accagtctga caaccgagga cacggccacc tatttctgtg ccggagcatt tagcgtctgg    300
ggcccgggca ccctcgtcac cgtctcgagc                                    330
```

<210> SEQ ID NO 39
<211> LENGTH: 439
<212> TYPE: PRT
<213> ORGANISM: Artificial Sequence
<220> FEATURE:
<223> OTHER INFORMATION: synthesized

<400> SEQUENCE: 39

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Asn Ala
            20                  25                  30

Ile Thr Trp Val Arg Gln Ala Pro Gly Lys Gly Leu Glu Tyr Ile Gly
        35                  40                  45

Ile Ile Ser Ser Ser Gly Thr Thr Tyr Tyr Ala Ser Trp Ala Lys Gly
    50                  55                  60

Arg Phe Thr Ile Ser Lys Thr Ser Ser Thr Val Asp Leu Lys Met
65                  70                  75                  80

Thr Ser Leu Thr Thr Glu Asp Thr Ala Thr Tyr Phe Cys Ala Gly Ala
                85                  90                  95

Phe Ser Val Trp Gly Pro Gly Thr Leu Val Thr Val Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
```

```
                    165                 170                 175
Ser Val Val Thr Val Pro Ser Ser Leu Gly Thr Gln Thr Tyr Ile
                180                 185                 190

Cys Asn Val Asn His Lys Pro Ser Asn Thr Lys Val Asp Lys Arg Val
            195                 200                 205

Glu Pro Lys Ser Cys Asp Lys Thr His Thr Cys Pro Pro Cys Pro Ala
210                 215                 220

Pro Glu Ala Ala Gly Ala Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Lys Phe Asn Trp Tyr Val
                260                 265                 270

Asp Gly Val Glu Val His Asn Ala Lys Thr Lys Pro Arg Glu Glu Gln
                275                 280                 285

Tyr Asn Ser Thr Tyr Arg Val Val Ser Val Leu Thr Val Leu His Gln
            290                 295                 300

Asp Trp Leu Asn Gly Lys Glu Tyr Lys Cys Ala Val Ser Asn Lys Ala
305                 310                 315                 320

Leu Pro Ala Pro Ile Glu Lys Thr Ile Ser Lys Ala Lys Gly Gln Pro
                325                 330                 335

Arg Glu Pro Gln Val Tyr Thr Leu Pro Pro Ser Arg Asp Glu Leu Thr
                340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
            420                 425                 430

Ser Leu Ser Leu Ser Pro Gly
        435

<210> SEQ ID NO 40
<211> LENGTH: 110
<212> TYPE: PRT
<213> ORGANISM: Artificial Sequence
<220> FEATURE:
<223> OTHER INFORMATION: synthesized

<400> SEQUENCE: 40

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Asn Ala
                20                  25                  30

Ile Thr Trp Val Arg Gln Ala Pro Gly Lys Gly Leu Glu Tyr Ile Gly
            35                  40                  45

Ile Ile Ser Ser Ser Gly Thr Thr Tyr Tyr Ala Ser Trp Ala Lys Gly
        50                  55                  60

Arg Phe Thr Ile Ser Lys Thr Ser Ser Thr Val Asp Leu Lys Met Thr
65                  70                  75                  80

Thr Ser Leu Thr Thr Glu Asp Thr Ala Thr Tyr Phe Cys Ala Gly Ala
```

```
                    85                  90                  95

Phe Ser Val Trp Gly Pro Gly Thr Leu Val Thr Val Ser Ser
            100                 105                 110
```

<210> SEQ ID NO 41
<211> LENGTH: 660
<212> TYPE: DNA
<213> ORGANISM: Artificial Sequence
<220> FEATURE:
<223> OTHER INFORMATION: synthesized

<400> SEQUENCE: 41

```
gatgttgtga tgacccagac tccagcctcc gtggaggcag ctgtgggagg cacagtcacc    60
atcaagtgcc aggccagtca gagcattgat agttggttat cctggtatca acagaaacca   120 ggcagcctc ccaagctcct gatctaccag gcatccactc tggcatctgg ggtctcatcg    180
cggttcaaag gcagtggatc tgggacagag ttcactctca ccatcagcga cctggagtgt   240
gccgatgctg ccacttacta ctgtcaatgc gcttatggtg ttagtggtac tagtagttat   300
ttatatactt tcggcggagg caccgaggtg gaggtcaaac gtacggtggc tgcaccatct   360
gtcttcatct cccgccatc tgatgagcag ttgaaatctg gaactgcctc tgttgtgtgc    420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
```

<210> SEQ ID NO 42
<211> LENGTH: 339
<212> TYPE: DNA
<213> ORGANISM: Artificial Sequence
<220> FEATURE:
<223> OTHER INFORMATION: synthesized

<400> SEQUENCE: 42

```
gatgttgtga tgacccagac tccagcctcc gtggaggcag ctgtgggagg cacagtcacc    60
atcaagtgcc aggccagtca gagcattgat agttggttat cctggtatca acagaaacca   120 ggcagcctc ccaagctcct gatctaccag gcatccactc tggcatctgg ggtctcatcg    180
cggttcaaag gcagtggatc tgggacagag ttcactctca ccatcagcga cctggagtgt   240
gccgatgctg ccacttacta ctgtcaatgc gcttatggtg ttagtggtac tagtagttat   300
ttatatactt tcggcggagg caccgaggtg gaggtcaaa                          339
```

<210> SEQ ID NO 43
<211> LENGTH: 220
<212> TYPE: PRT
<213> ORGANISM: Artificial Sequence
<220> FEATURE:
<223> OTHER INFORMATION: synthesized

<400> SEQUENCE: 43

```
Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Asp Ser Trp
            20                  25                  30

Leu Ser Trp Tyr Gln Gln Lys Pro Gly Gln Pro Pro Lys Leu Leu Ile
        35                  40                  45

Tyr Gln Ala Ser Thr Leu Ala Ser Gly Val Ser Ser Arg Phe Lys Gly
```

```
Ser Gly Ser Gly Thr Glu Phe Thr Leu Thr Ile Ser Asp Leu Glu Cys
 65                  70                  75                  80

Ala Asp Ala Ala Thr Tyr Tyr Cys Gln Cys Ala Tyr Gly Val Ser Gly
                 85                  90                  95

Thr Ser Ser Tyr Leu Tyr Thr Phe Gly Gly Gly Thr Glu Val Glu Val
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 44
<211> LENGTH: 113
<212> TYPE: PRT
<213> ORGANISM: Artificial Sequence
<220> FEATURE:
<223> OTHER INFORMATION: synthesized

<400> SEQUENCE: 44

Asp Val Val Met Thr Gln Thr Pro Ala Ser Val Glu Ala Ala Val Gly
  1               5                  10                  15

Gly Thr Val Thr Ile Lys Cys Gln Ala Ser Gln Ser Ile Asp Ser Trp
                 20                  25                  30

Leu Ser Trp Tyr Gln Gln Lys Pro Gly Gln Pro Pro Lys Leu Leu Ile
             35                  40                  45

Tyr Gln Ala Ser Thr Leu Ala Ser Gly Val Ser Ser Arg Phe Lys Gly
     50                  55                  60

Ser Gly Ser Gly Thr Glu Phe Thr Leu Thr Ile Ser Asp Leu Glu Cys
 65                  70                  75                  80

Ala Asp Ala Ala Thr Tyr Tyr Cys Gln Cys Ala Tyr Gly Val Ser Gly
                 85                  90                  95

Thr Ser Ser Tyr Leu Tyr Thr Phe Gly Gly Gly Thr Glu Val Glu Val
                100                 105                 110

Lys

<210> SEQ ID NO 45
<211> LENGTH: 1338
<212> TYPE: DNA
<213> ORGANISM: Artificial Sequence
<220> FEATURE:
<223> OTHER INFORMATION: synthesized

<400> SEQUENCE: 45
cagtcgctgg aggagtccgg gggtcgcctg gtcacgcctg gacacccct gacactcacc      60 tgcacagcct ctggattctc cctcagtagg tactacatga cctgggtccg ccaggctcca    120
```

-continued

```
gggaaggggc tggagtggat tggaaccatt tatactagtg gtagtacatg gtacgcgagc    180
tggacaaaag gccgattcac catctccaaa acctcgacca cggtggatct gaaaatcact    240
agtccgacaa ccgaggacac ggccacctat ttctgtgcca gatcctatta tggcggtgat    300
aagactggtt taggcatctg ggcccaggc accctcgtca ccgtctcgag cgctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaag ccgcggggc accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcgcggtct ccaacaaagc cctcccagcc cccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta tagcaagctc accgtggaca agagcaggtg gcagcagggg    1260
aacgtcttct catgctccgt gatgcatgag gctctgcaca accactacac gcagaagagc    1320
ctctccctgt ctccgggt                                                  1338
```

<210> SEQ ID NO 46
<211> LENGTH: 351
<212> TYPE: DNA
<213> ORGANISM: Artificial Sequence
<220> FEATURE:
<223> OTHER INFORMATION: synthesized

<400> SEQUENCE: 46

```
cagtcgctgg aggagtccgg gggtcgcctg gtcacgcctg gacacccct gacactcacc     60
tgcacagcct ctggattctc cctcagtagg tactacatga cctgggtccg ccaggctcca   120
gggaaggggc tggagtggat tggaaccatt tatactagtg gtagtacatg gtacgcgagc   180
tggacaaaag gccgattcac catctccaaa acctcgacca cggtggatct gaaaatcact   240
agtccgacaa ccgaggacac ggccacctat ttctgtgcca gatcctatta tggcggtgat   300
aagactggtt taggcatctg ggcccaggc accctcgtca ccgtctcgag c             351
```

<210> SEQ ID NO 47
<211> LENGTH: 446
<212> TYPE: PRT
<213> ORGANISM: Artificial Sequence
<220> FEATURE:
<223> OTHER INFORMATION: synthesized

<400> SEQUENCE: 47

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Arg Tyr Tyr
            20                  25                  30
```

```
Met Thr Trp Val Arg Gln Ala Pro Gly Lys Gly Leu Glu Trp Ile Gly
                 35                  40                  45

Thr Ile Tyr Thr Ser Gly Ser Thr Trp Tyr Ala Ser Trp Thr Lys Gly
 50                  55                  60

Arg Phe Thr Ile Ser Lys Thr Ser Thr Thr Val Asp Leu Lys Ile Thr
 65                  70                  75                  80

Ser Pro Thr Thr Glu Asp Thr Ala Thr Tyr Phe Cys Ala Arg Ser Tyr
                 85                  90                  95

Tyr Gly Gly Asp Lys Thr Gly Leu Gly Ile Trp Gly Pro Gly Thr Leu
                 100                 105                 110

Val Thr Val Ser Ser Ala Ser Thr Lys Gly Pro Ser Val Phe Pro Leu
                 115                 120                 125

Ala Pro Ser Ser Lys Ser Thr Ser Gly Gly Thr Ala Ala Leu Gly Cys
 130                 135                 140

Leu Val Lys Asp Tyr Phe Pro Glu Pro Val Thr Val Ser Trp Asn Ser
 145                 150                 155                 160

Gly Ala Leu Thr Ser Gly Val His Thr Phe Pro Ala Val Leu Gln Ser
                 165                 170                 175

Ser Gly Leu Tyr Ser Leu Ser Ser Val Val Thr Val Pro Ser Ser Ser
                 180                 185                 190

Leu Gly Thr Gln Thr Tyr Ile Cys Asn Val Asn His Lys Pro Ser Asn
                 195                 200                 205

Thr Lys Val Asp Lys Arg Val Glu Pro Lys Ser Cys Asp Lys Thr His
 210                 215                 220

Thr Cys Pro Pro Cys Pro Ala Pro Glu Ala Ala Gly Ala Pro Ser Val
 225                 230                 235                 240

Phe Leu Phe Pro Pro Lys Pro Lys Asp Thr Leu Met Ile Ser Arg Thr
                 245                 250                 255

Pro Glu Val Thr Cys Val Val Val Asp Val Ser His Glu Asp Pro Glu
                 260                 265                 270

Val Lys Phe Asn Trp Tyr Val Asp Gly Val Glu Val His Asn Ala Lys
                 275                 280                 285

Thr Lys Pro Arg Glu Glu Gln Tyr Asn Ser Thr Tyr Arg Val Val Ser
                 290                 295                 300

Val Leu Thr Val Leu His Gln Asp Trp Leu Asn Gly Lys Glu Tyr Lys
 305                 310                 315                 320

Cys Ala Val Ser Asn Lys Ala Leu Pro Ala Pro Ile Glu Lys Thr Ile
                 325                 330                 335

Ser Lys Ala Lys Gly Gln Pro Arg Glu Pro Gln Val Tyr Thr Leu Pro
                 340                 345                 350

Pro Ser Arg Asp Glu Leu Thr Lys Asn Gln Val Ser Leu Thr Cys Leu
                 355                 360                 365

Val Lys Gly Phe Tyr Pro Ser Asp Ile Ala Val Glu Trp Glu Ser Asn
 370                 375                 380

Gly Gln Pro Glu Asn Asn Tyr Lys Thr Thr Pro Val Leu Asp Ser
385                  390                 395                 400

Asp Gly Ser Phe Phe Leu Tyr Ser Lys Leu Thr Val Asp Lys Ser Arg
                 405                 410                 415

Trp Gln Gln Gly Asn Val Phe Ser Cys Ser Val Met His Glu Ala Leu
                 420                 425                 430

His Asn His Tyr Thr Gln Lys Ser Leu Ser Leu Ser Pro Gly
                 435                 440                 445
```

<210> SEQ ID NO 48
<211> LENGTH: 117
<212> TYPE: PRT
<213> ORGANISM: Artificial Sequence
<220> FEATURE:
<223> OTHER INFORMATION: synthesized

<400> SEQUENCE: 48

```
Gln Ser Leu Glu Glu Ser Gly Gly Arg Leu Val Thr Pro Gly Thr Pro
1               5                   10                  15
Leu Thr Leu Thr Cys Thr Ala Ser Gly Phe Ser Leu Ser Arg Tyr Tyr
            20                  25                  30
Met Thr Trp Val Arg Gln Ala Pro Gly Lys Gly Leu Glu Trp Ile Gly
        35                  40                  45
Thr Ile Tyr Thr Ser Gly Ser Thr Trp Tyr Ala Ser Trp Thr Lys Gly
    50                  55                  60
Arg Phe Thr Ile Ser Lys Thr Ser Thr Thr Val Asp Leu Lys Ile Thr
65                  70                  75                  80
Ser Pro Thr Thr Glu Asp Thr Ala Thr Tyr Phe Cys Ala Arg Ser Tyr
                85                  90                  95
Tyr Gly Gly Asp Lys Thr Gly Leu Gly Ile Trp Gly Pro Gly Thr Leu
            100                 105                 110
Val Thr Val Ser Ser
        115
```

<210> SEQ ID NO 49
<211> LENGTH: 642
<212> TYPE: DNA
<213> ORGANISM: Artificial Sequence
<220> FEATURE:
<223> OTHER INFORMATION: synthesized

<400> SEQUENCE: 49

| | | | | | |
|---|---|---|---|---|---|
| gacattgtga | tgacccagac | tccagcctcg | gtgtctgcag | ctgtgggagg | cacagtcacc | 60 |
| atcaattgcc | aggccagtca | gaacatttac | agctactat | cctggtatca | gcagaaacca | 120 |
| gggcagcctc | ccaagcgcct | gatctatctg | catcactc | tggcatctgg | ggtcccatcg | 180 |
| cggttcaaaa | gcagtggatc | tgggacagag | tacactctca | ccatcagcga | cctggagtgt | 240 |
| gacgatgctg | ccacttacta | ctgtcaaagc | aattataacg | gtaattatgg | tttcggcgga | 300 |
| gggaccgagg | tggaggtcaa | acgtacggtg | gctgcaccat | ctgtcttcat | cttcccgcca | 360 |
| tctgatgagc | agttgaaatc | tggaactgcc | tctgttgtgt | gcctgctgaa | taacttctat | 420 |
| cccagagagg | ccaaagtaca | gtggaaggtg | gataacgccc | tccaatcggg | taactcccag | 480 |
| gagagtgtca | cagagcagga | cagcaaggac | agcacctaca | gcctcagcag | caccctgacg | 540 |
| ctgagcaaag | cagactacga | gaaacacaaa | gtctacgcct | gcgaagtcac | ccatcagggc | 600 |
| ctgagctcgc | ccgtcacaaa | gagcttcaac | aggggagagt | gt | | 642 |

<210> SEQ ID NO 50
<211> LENGTH: 321
<212> TYPE: DNA
<213> ORGANISM: Artificial Sequence
<220> FEATURE:
<223> OTHER INFORMATION: synthesized

<400> SEQUENCE: 50

| | | | | | |
|---|---|---|---|---|---|
| gacattgtga | tgacccagac | tccagcctcg | gtgtctgcag | ctgtgggagg | cacagtcacc | 60 |
| atcaattgcc | aggccagtca | gaacatttac | agctactat | cctggtatca | gcagaaacca | 120 |

```
gggcagcctc ccaagcgcct gatctatctg gcatctactc tggcatctgg ggtcccatcg    180
cggttcaaaa gcagtggatc tgggacagag tacactctca ccatcagcga cctggagtgt    240
gacgatgctg ccacttacta ctgtcaaagc aattataacg gtaattatgg tttcggcgga    300
gggaccgagg tggaggtcaa a                                              321
```

<210> SEQ ID NO 51
<211> LENGTH: 214
<212> TYPE: PRT
<213> ORGANISM: Artificial Sequence
<220> FEATURE:
<223> OTHER INFORMATION: synthesized

<400> SEQUENCE: 51

Asp Ile Val Met Thr Gln Thr Pro Ala Ser Val Ser Ala Ala Val Gly
1               5                   10                  15

Gly Thr Val Thr Ile Asn Cys Gln Ala Ser Gln Asn Ile Tyr Ser Tyr
            20                  25                  30

Leu Ser Trp Tyr Gln Gln Lys Pro Gly Gln Pro Pro Lys Arg Leu Ile
        35                  40                  45

Tyr Leu Ala Ser Thr Leu Ala Ser Gly Val Pro Ser Arg Phe Lys Ser
    50                  55                  60

Ser Gly Ser Gly Thr Glu Tyr Thr Leu Thr Ile Ser Asp Leu Glu Cys
65                  70                  75                  80

Asp Asp Ala Ala Thr Tyr Tyr Cys Gln Ser Asn Tyr Asn Gly Asn Tyr
                85                  90                  95

Gly Phe Gly Gly Gly Thr Glu Val Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 52
<211> LENGTH: 107
<212> TYPE: PRT
<213> ORGANISM: Artificial Sequence
<220> FEATURE:
<223> OTHER INFORMATION: synthesized

<400> SEQUENCE: 52

Asp Ile Val Met Thr Gln Thr Pro Ala Ser Val Ser Ala Ala Val Gly
1               5                   10                  15

Gly Thr Val Thr Ile Asn Cys Gln Ala Ser Gln Asn Ile Tyr Ser Tyr
            20                  25                  30

Leu Ser Trp Tyr Gln Gln Lys Pro Gly Gln Pro Pro Lys Arg Leu Ile
        35                  40                  45

Tyr Leu Ala Ser Thr Leu Ala Ser Gly Val Pro Ser Arg Phe Lys Ser
        50                  55                  60

Ser Gly Ser Gly Thr Glu Tyr Thr Leu Thr Ile Ser Asp Leu Glu Cys
65                  70                  75                  80

Asp Asp Ala Ala Thr Tyr Tyr Cys Gln Ser Asn Tyr Asn Gly Asn Tyr
                85                  90                  95

Gly Phe Gly Gly Gly Thr Glu Val Glu Val Lys
            100                 105

<210> SEQ ID NO 53
<211> LENGTH: 1323
<212> TYPE: DNA
<213> ORGANISM: Artificial Sequence
<220> FEATURE:
<223> OTHER INFORMATION: synthesized

<400> SEQUENCE: 53

| | | | | | |
|---|---|---|---|---|---|
| cagtcggtgg | aggagtccgg | gggtcgcctg | gtcacgcctg | ggacacccct | gacactcacc | 60 |
| tgcaccgtct | ctggattctc | cctcagtagc | tatgcaatga | gctgggtccg | ccaggctcca | 120 |
| gggaggggc | tggaatggat | cggaatcatt | tatgctagtg | gtagcacata | ctacgcgagc | 180 |
| tgggcgaaag | gccgattcac | catctccaaa | acctcgacca | cggtggatct | gaaaatcacc | 240 |
| agtccgacaa | ccgaggacac | ggccacctat | ttctgtgcca | gaatttatga | cggcatggac | 300 |
| ctctggggcc | agggaccct | cgtcaccgtc | tcgagcgcta | gcaccaaggg | cccatcggtc | 360 |
| ttcccctgg | cacctcctc | caagagcacc | tctgggggca | cagcggccct | gggctgcctg | 420 |
| gtcaaggact | acttccccga | accggtgacg | gtgtcgtgga | actcaggcgc | cctgaccagc | 480 |
| ggcgtgcaca | ccttccccggc | tgtcctacag | tcctcaggac | tctactccct | cagcagcgtg | 540 |
| gtgaccgtgc | cctccagcag | cttgggcacc | cagacctaca | tctgcaacgt | gaatcacaag | 600 |
| cccagcaaca | ccaaggtgga | caagagagtt | gagcccaaat | cttgtgacaa | aactcacaca | 660 |
| tgcccaccgt | gcccagcacc | tgaagccgcg | ggggcaccgt | cagtcttcct | cttccccca | 720 |
| aaacccaagg | acaccctcat | gatctcccgg | acccctgagg | tcacatgcgt | ggtggtggac | 780 |
| gtgagccacg | aagaccctga | ggtcaagttc | aactggtacg | tggacggcgt | ggaggtgcat | 840 |
| aatgccaaga | caaagccgcg | ggaggagcag | tacaacagca | cgtaccgtgt | ggtcagcgtc | 900 |
| ctcaccgtcc | tgcaccagga | ctggctgaat | ggcaaggagt | acaagtgcgc | ggtctccaac | 960 |
| aaagccctcc | cagcccccat | cgagaaaacc | atctccaaag | ccaaagggca | gccccgagaa | 1020 |
| ccacaggtgt | acaccctgcc | cccatcccgg | gatgagctga | ccaagaacca | ggtcagcctg | 1080 |
| acctgcctgg | tcaaaggctt | ctatcccagc | gacatcgccg | tggagtggga | gagcaatggg | 1140 |
| cagccggaga | acaactacaa | gaccacgcct | cccgtgctgg | actccgacgg | ctccttcttc | 1200 |
| ctctatagca | agctcaccgt | ggacaagagc | aggtggcagc | aggggaacgt | cttctcatgc | 1260 |
| tccgtgatgc | atgaggctct | gcacaaccac | tacacgcaga | agagcctctc | cctgtctccg | 1320 |
| ggt | | | | | | 1323 |

<210> SEQ ID NO 54
<211> LENGTH: 336
<212> TYPE: DNA
<213> ORGANISM: Artificial Sequence
<220> FEATURE:
<223> OTHER INFORMATION: synthesized

<400> SEQUENCE: 54

-continued

```
cagtcggtgg aggagtccgg gggtcgcctg gtcacgcctg ggacacccct gacactcacc    60
tgcaccgtct ctggattctc cctcagtagc tatgcaatga gctgggtccg ccaggctcca   120 gggaggggc tggaatggat cggaatcatt tatgctagtg gtagcacata ctacgcgagc   180
tgggcgaaag gccgattcac catctccaaa acctcgacca cggtggatct gaaaatcacc   240
agtccgacaa ccgaggacac ggccacctat ttctgtgcca gaatttatga cggcatggac   300
ctctggggcc agggaccct cgtcaccgtc tcgagc                             336
```

<210> SEQ ID NO 55
<211> LENGTH: 441
<212> TYPE: PRT
<213> ORGANISM: Artificial Sequence
<220> FEATURE:
<223> OTHER INFORMATION: synthesized

<400> SEQUENCE: 55

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Arg Gly Leu Glu Trp Ile Gly
        35                  40                  45

Ile Ile Tyr Ala Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Ile Tyr
                85                  90                  95

Asp Gly Met Asp Leu Trp Gly Pro Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Arg Val Glu Pro Lys Ser Cys Asp Lys Thr His Thr Cys Pro Pro Cys
    210                 215                 220

Pro Ala Pro Glu Ala Ala Gly Ala Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300
```

His Gln Asp Trp Leu Asn Gly Lys Glu Tyr Lys Cys Ala Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 56
<211> LENGTH: 112
<212> TYPE: PRT
<213> ORGANISM: Artificial Sequence
<220> FEATURE:
<223> OTHER INFORMATION: synthesized

<400> SEQUENCE: 56

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Arg Gly Leu Glu Trp Ile Gly
        35                  40                  45

Ile Ile Tyr Ala Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Ile Tyr
                85                  90                  95

Asp Gly Met Asp Leu Trp Gly Pro Gly Thr Leu Val Thr Val Ser Ser
            100                 105                 110

<210> SEQ ID NO 57
<211> LENGTH: 645
<212> TYPE: DNA
<213> ORGANISM: Artificial Sequence
<220> FEATURE:
<223> OTHER INFORMATION: synthesized

<400> SEQUENCE: 57
gatgttgtga tgacccagac tccagcctcc gtggaggcag ctgtgggagg cacagtcacc      60
atcaagtgcc aggccagtca gagcattaat aactacttag cctggtatca gcagaaacca     120
gggcagcctc ccaagctcct gatctacagg gcatccactc tggaatctgg ggtcccatcg     180
cggttcaaag gcagtggatc tgggacacag ttcactctca ccatcagcga cctggagtgt     240
gccgatgctg ccacttacta ttgtcaaagc tataatggtg ttggtaggac tgctttcggc     300
ggagggaccg aggtggagtt caaacgtacg gtggctgcac catctgtctt catcttcccg     360

```
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                   645
```

<210> SEQ ID NO 58
<211> LENGTH: 324
<212> TYPE: PRT
<213> ORGANISM: Artificial Sequence
<220> FEATURE:
<223> OTHER INFORMATION: synthesized

<400> SEQUENCE: 58

```
Gly Ala Thr Gly Thr Gly Thr Gly Ala Thr Gly Ala Cys Cys Cys
1               5                   10                  15

Ala Gly Ala Cys Thr Cys Cys Ala Gly Cys Cys Thr Cys Gly Thr
                20                  25                  30

Gly Gly Ala Gly Gly Cys Ala Gly Cys Thr Gly Thr Gly Gly Ala
                35                  40                  45

Gly Gly Cys Ala Cys Ala Gly Thr Cys Ala Cys Ala Thr Cys Ala
                50                  55                  60

Ala Gly Thr Gly Cys Cys Ala Gly Cys Cys Ala Gly Thr Cys Ala
65                  70                  75                  80

Gly Ala Gly Cys Ala Thr Thr Ala Ala Thr Ala Ala Cys Thr Ala Cys
                    85                  90                  95

Thr Thr Ala Gly Cys Cys Thr Gly Gly Thr Ala Thr Cys Ala Gly Cys
                    100                 105                 110

Ala Gly Ala Ala Ala Cys Cys Ala Gly Gly Cys Ala Gly Cys Cys
                    115                 120                 125

Thr Cys Cys Cys Ala Ala Gly Cys Thr Cys Cys Thr Gly Ala Thr Cys
                    130                 135                 140

Thr Ala Cys Ala Gly Gly Cys Ala Thr Cys Cys Ala Cys Thr Cys
145                 150                 155                 160

Thr Gly Gly Ala Ala Thr Cys Thr Gly Gly Gly Thr Cys Cys Cys
                    165                 170                 175

Ala Thr Cys Gly Cys Gly Gly Thr Thr Cys Ala Ala Ala Gly Gly Cys
                    180                 185                 190

Ala Gly Thr Gly Gly Ala Thr Cys Thr Gly Gly Ala Cys Ala Cys
                    195                 200                 205

Ala Gly Thr Thr Cys Ala Cys Thr Cys Thr Cys Ala Cys Cys Ala Thr
                    210                 215                 220

Cys Ala Gly Cys Gly Ala Cys Cys Thr Gly Gly Ala Gly Thr Gly Thr
225                 230                 235                 240

Gly Cys Cys Gly Ala Thr Gly Cys Thr Gly Cys Cys Ala Cys Thr
                    245                 250                 255

Ala Cys Thr Ala Thr Thr Gly Thr Cys Ala Ala Gly Cys Thr Ala
                    260                 265                 270

Thr Ala Ala Thr Gly Gly Thr Gly Thr Gly Thr Ala Gly Gly
                    275                 280                 285

Ala Cys Thr Gly Cys Thr Thr Thr Cys Gly Gly Cys Gly Gly Ala Gly
                    290                 295                 300

Gly Gly Ala Cys Cys Gly Ala Gly Gly Thr Gly Gly Ala Gly Thr Thr
```

```
                305                 310                 315                 320

Cys Ala Ala Ala

<210> SEQ ID NO 59
<211> LENGTH: 215
<212> TYPE: PRT
<213> ORGANISM: Artificial Sequence
<220> FEATURE:
<223> OTHER INFORMATION: synthesized

<400> SEQUENCE: 59

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Asn Asn Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Glu Ser Gly Val Pro Ser Arg Phe Lys Gly
50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser Tyr Asn Gly Val Gly Arg
                85                  90                  95

Thr Ala Phe Gly Gly Gly Thr Glu Val Glu Phe Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 60
<211> LENGTH: 108
<212> TYPE: PRT
<213> ORGANISM: Artificial Sequence
<220> FEATURE:
<223> OTHER INFORMATION: synthesized

<400> SEQUENCE: 60

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Asn Asn Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Glu Ser Gly Val Pro Ser Arg Phe Lys Gly
50                  55                  60

Ser Gly Ser Gly Thr Gln Phe Thr Leu Thr Ile Ser Asp Leu Glu Cys
```

```
               65                  70                  75                  80
Ala Asp Ala Ala Thr Tyr Tyr Cys Gln Ser Tyr Asn Gly Val Gly Arg
                        85                  90                  95

Thr Ala Phe Gly Gly Gly Thr Glu Val Glu Phe Lys
            100                 105
```

<210> SEQ ID NO 61
<211> LENGTH: 1338
<212> TYPE: DNA
<213> ORGANISM: Artificial Sequence
<220> FEATURE:
<223> OTHER INFORMATION: synthesized

<400> SEQUENCE: 61

```
cagtcggtgg aggagtccgg gggtcgcctg gtcacgcctg ggacacccct gacactcacc      60
tgcacagtct ctggattctc cctcaataac tactggatga gctgggtccg ccaggctcca     120
ggggaggggc tggaatggat cggaaccatt agtagtggtg cgtatacatg gttcgccacc     180
tgggcgacag gccgattcac catctccaaa acctcgacca cggtggatct gagcatcacc     240
agtccgacaa ccgaggacac ggccacctat ttctgtgcca gatattcttc tactactgat     300
tggacctact ttaacatctg gggccgggc accctggtca ccgtctcgag cgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga gagttgagcc caaatcttgt     660
gacaaaactc acacatgccc accgtgccca gcacctgaag ccgcggggc accgtcagtc     720 ttcctcttcc cccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcgcggtct ccaacaaagc cctcccagcc cccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta tagcaagctc accgtggaca agagcaggtg gcagcagggg    1260
aacgtcttct catgctccgt gatgcatgag gctctgcaca accactacac gcagaagagc    1320
ctctccctgt ctccgggt                                                  1338
```

<210> SEQ ID NO 62
<211> LENGTH: 351
<212> TYPE: DNA
<213> ORGANISM: Artificial Sequence
<220> FEATURE:
<223> OTHER INFORMATION: synthesized

<400> SEQUENCE: 62

```
cagtcggtgg aggagtccgg gggtcgcctg gtcacgcctg ggacacccct gacactcacc      60
tgcacagtct ctggattctc cctcaataac tactggatga gctgggtccg ccaggctcca     120
ggggaggggc tggaatggat cggaaccatt agtagtggtg cgtatacatg gttcgccacc     180
```
tgggcgacag gccgattcac catctccaaa acctcgacca cggtggatct gagcatcacc    240
agtccgacaa ccgaggacac ggccacctat ttctgtgcca gatattcttc tactactgat    300
tggacctact ttaacatctg gggcccgggc accctggtca ccgtctcgag c             351

<210> SEQ ID NO 63
<211> LENGTH: 446
<212> TYPE: PRT
<213> ORGANISM: Artificial Sequence
<220> FEATURE:
<223> OTHER INFORMATION: synthesized

<400> SEQUENCE: 63

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Trp
            20                  25                  30

Met Ser Trp Val Arg Gln Ala Pro Gly Glu Gly Leu Glu Trp Ile Gly
        35                  40                  45

Thr Ile Ser Ser Gly Ala Tyr Thr Trp Phe Ala Thr Trp Ala Thr Gly
    50                  55                  60

Arg Phe Thr Ile Ser Lys Thr Ser Thr Thr Val Asp Leu Ser Ile Thr
65                  70                  75                  80

Ser Pro Thr Thr Glu Asp Thr Ala Thr Tyr Phe Cys Ala Arg Tyr Ser
                85                  90                  95

Ser Thr Thr Asp Trp Thr Tyr Phe Asn Ile Trp Gly Pro Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335
```

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 64
<211> LENGTH: 117
<212> TYPE: PRT
<213> ORGANISM: Artificial Sequence
<220> FEATURE:
<223> OTHER INFORMATION: synthesized

<400> SEQUENCE: 64

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Trp
            20                  25                  30

Met Ser Trp Val Arg Gln Ala Pro Gly Glu Gly Leu Glu Trp Ile Gly
        35                  40                  45

Thr Ile Ser Ser Gly Ala Tyr Thr Trp Phe Ala Thr Trp Ala Thr Gly
    50                  55                  60

Arg Phe Thr Ile Ser Lys Thr Ser Thr Thr Val Asp Leu Ser Ile Thr
65                  70                  75                  80

Ser Pro Thr Thr Glu Asp Thr Ala Thr Tyr Phe Cys Ala Arg Tyr Ser
                85                  90                  95

Ser Thr Thr Asp Trp Thr Tyr Phe Asn Ile Trp Gly Pro Gly Thr Leu
            100                 105                 110

Val Thr Val Ser Ser
        115

<210> SEQ ID NO 65
<211> LENGTH: 651
<212> TYPE: DNA
<213> ORGANISM: Artificial Sequence
<220> FEATURE:
<223> OTHER INFORMATION: synthesized

<400> SEQUENCE: 65
gacatccaga tgacccagtc tccatcctcc ctgtctgcat ctgtaggaga cagagtcacc      60
atcacttgcc aggccagtca gaatttac agctacttag cctggtatca gcagaaacca      120
gggaaagttc ctaagctcct gatctatagg gcatccactc tggcatctgg ggtcccatct      180
cggttcagtg gcagtggatc tgggacagat tcactctca ccatcagcag cctgcagcct      240
gaagatgttg caacttatta ctgtcaacag ggtgctagta tggttgatgt tgagaatatg      300
ttcggcggag ggaccaaggt ggagatcaaa cgtacggtgg ctgcaccatc tgtcttcatc      360
ttcccgccat ctgatgagca gttgaaatct ggaactgcct ctgttgtgtg cctgctgaat      420

```
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t             651
```

<210> SEQ ID NO 66
<211> LENGTH: 330
<212> TYPE: DNA
<213> ORGANISM: Artificial Sequence
<220> FEATURE:
<223> OTHER INFORMATION: synthesized

<400> SEQUENCE: 66

```
gacatccaga tgacccagtc tccatcctcc ctgtctgcat ctgtaggaga cagagtcacc     60
atcacttgcc aggccagtca gagaatttac agctacttag cctggtatca gcagaaacca    120
gggaaagttc ctaagctcct gatctatagg gcatccactc tggcatctgg ggtcccatct    180
cggttcagtg gcagtggatc tgggacagat ttcactctca ccatcagcag cctgcagcct    240
gaagatgttg caacttatta ctgtcaacag ggtgctagta tggttgatgt tgagaatatg    300
ttcggcggag ggaccaaggt ggagatcaaa                                     330
```

<210> SEQ ID NO 67
<211> LENGTH: 217
<212> TYPE: PRT
<213> ORGANISM: Artificial Sequence
<220> FEATURE:
<223> OTHER INFORMATION: synthesized

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Arg Ile Tyr Ser Tyr
            20                  25                  30

Leu Ala Trp Tyr Gln Gln Lys Pro Gly Lys Val Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Ala Ser Met Val Asp
                85                  90                  95

Val Glu Asn Met Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205
```

<210> SEQ ID NO 68
<211> LENGTH: 110
<212> TYPE: PRT
<213> ORGANISM: Artificial Sequence
<220> FEATURE:
<223> OTHER INFORMATION: synthesized

<400> SEQUENCE: 68

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Arg Ile Tyr Ser Tyr
            20                  25                  30

Leu Ala Trp Tyr Gln Gln Lys Pro Gly Lys Val Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Ala Ser Met Val Asp
                85                  90                  95

Val Glu Asn Met Phe Gly Gly Gly Thr Lys Val Glu Ile Lys
            100                 105                 110
```

<210> SEQ ID NO 69
<211> LENGTH: 1347
<212> TYPE: DNA
<213> ORGANISM: Artificial Sequence
<220> FEATURE:
<223> OTHER INFORMATION: synthesized

<400> SEQUENCE: 69

```
gaggtgcagc tgttggagtc tgggggaggc ttggtacagc ctggggggtc cctgagactc      60
tcctgtgcag cctctggatt ctccctcagt aactactaca tgagctgggt ccgccaggct     120
ccagggaagg ggctggagtg gatcggagcc attaatgctg acagtgataa acatggtac     180 ccgagctggg tgaaaggccg gttcaccatc tccagagaca attccaagaa cacgctgtat     240
ctgcaaatga acagcctgag agccgaggac acggccgtat attactgtgc gagaagtgtg     300
agtaataatt cgccgaata taacatctgg ggccagggaa ccctggtcac cgtctcgagc     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaagc cgcgggggca     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcgcggtctc caacaaagcc ctcccagccc ccatcgagaa aaccatctcc    1020
```

```
aaagccaaag ggcagccccg agaaccacag gtgtacaccc tgccccatc ccgggatgag    1080 ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctat agcaagctca ccgtggacaa gagcaggtgg    1260
cagcagggga acgtcttctc atgctccgtg atgcatgagg ctctgcacaa ccactacacg    1320
cagaagagcc tctccctgtc tccgggt                                        1347
```

<210> SEQ ID NO 70
<211> LENGTH: 360
<212> TYPE: DNA
<213> ORGANISM: Artificial Sequence
<220> FEATURE:
<223> OTHER INFORMATION: synthesized

<400> SEQUENCE: 70

```
gaggtgcagc tgttggagtc tgggggaggc ttggtacagc ctgggggtc cctgagactc      60 tcctgtgcag cctctggatt ctccctcagt aactactaca tgagctgggt ccgccaggct    120
ccagggaagg ggctggagtg gatcggagcc attaatgctg acagtgataa tacatggtac    180
ccgagctggg tgaaaggccg gttcaccatc tccagagaca attccaagaa cacgctgtat    240
ctgcaaatga acagcctgag agccgaggac acggccgtat attactgtgc gagaagtgtg    300
agtaataatt tcgccgaata taacatctgg ggccagggaa ccctggtcac cgtctcgagc    360
```

<210> SEQ ID NO 71
<211> LENGTH: 449
<212> TYPE: PRT
<213> ORGANISM: Artificial Sequence
<220> FEATURE:
<223> OTHER INFORMATION: synthesized

<400> SEQUENCE: 71

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Met Ser Trp Val Arg Gln Ala Pro Gly Lys Gly Leu Glu Trp Ile
        35                  40                  45

Gly Ala Ile Asn Ala Asp Ser Asp Asn Thr Trp Tyr Pro Ser Trp Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Val Ser Asn Asn Phe Ala Glu Tyr Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 72
<211> LENGTH: 120
<212> TYPE: PRT
<213> ORGANISM: Artificial Sequence
<220> FEATURE:
<223> OTHER INFORMATION: synthesized

<400> SEQUENCE: 72

Glu Val Gln Leu Leu Glu Ser Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Met Ser Trp Val Arg Gln Ala Pro Gly Lys Gly Leu Glu Trp Ile
        35                  40                  45

Gly Ala Ile Asn Ala Asp Ser Asp Asn Thr Trp Tyr Pro Ser Trp Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Val Ser Asn Asn Phe Ala Glu Tyr Asn Ile Trp Gly Gln
            100                 105                 110

Gly Thr Leu Val Thr Val Ser Ser
        115                 120

<210> SEQ ID NO 73
<211> LENGTH: 660
<212> TYPE: DNA
<213> ORGANISM: Artificial Sequence
<220> FEATURE:
<223> OTHER INFORMATION: synthesized

<400> SEQUENCE: 73
gacatccaga tgacccagtc tccatcctcc ctgtctgcat ctgtaggaga cagagtcacc      60
atcacttgcc agtccagtca gagtgtttat aacaacaacg acttagcctg gtatcagcag     120
aaaccaggga agttcctaa gctcctgatc tattatgcat ccactctggc atctggggtc     180
ccatctcggt tcagtggcag tggatctggg acagatttca ctctcaccat cagcagcctg     240
cagcctgaag atgttgcaac ttattactgt gcaggcggtt atgatacgga tggtcttgat     300
acgtttgctt cggcggagg gaccaaggtg gagatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga acacaaagt ctacgcctgc      600
gaagtcaccc atcagggcct gagctcgccc gtcacaaaga gcttcaacag gggagagtgt     660

<210> SEQ ID NO 74
<211> LENGTH: 339
<212> TYPE: DNA
<213> ORGANISM: Artificial Sequence
<220> FEATURE:
<223> OTHER INFORMATION: synthesized

<400> SEQUENCE: 74
gacatccaga tgacccagtc tccatcctcc ctgtctgcat ctgtaggaga cagagtcacc      60
atcacttgcc agtccagtca gagtgtttat aacaacaacg acttagcctg gtatcagcag     120
aaaccaggga agttcctaa gctcctgatc tattatgcat ccactctggc atctggggtc     180
ccatctcggt tcagtggcag tggatctggg acagatttca ctctcaccat cagcagcctg     240
cagcctgaag atgttgcaac ttattactgt gcaggcggtt atgatacgga tggtcttgat     300
acgtttgctt cggcggagg gaccaaggtg gagatcaaa                             339

<210> SEQ ID NO 75
<211> LENGTH: 220
<212> TYPE: PRT
<213> ORGANISM: Artificial Sequence
<220> FEATURE:
<223> OTHER INFORMATION: synthesized

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Asp Leu Ala Trp Tyr Gln Gln Lys Pro Gly Lys Val Pro Lys Leu
        35                  40                  45

```
Leu Ile Tyr Tyr Ala Ser Thr Leu Ala Ser Gly Val Pro Ser Arg Phe
 50                  55                  60

Ser Gly Ser Gly Ser Gly Thr Asp Phe Thr Leu Thr Ile Ser Ser Leu
 65                  70                  75                  80

Gln Pro Glu Asp Val Ala Thr Tyr Tyr Cys Ala Gly Gly Tyr Asp Thr
                 85                  90                  95

Asp Gly Leu Asp Thr Phe Ala Phe Gly Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 76
<211> LENGTH: 113
<212> TYPE: PRT
<213> ORGANISM: Artificial Sequence
<220> FEATURE:
<223> OTHER INFORMATION: synthesized

<400> SEQUENCE: 76

Asp Ile Gln Met Thr Gln Ser Pro Ser Ser Leu Ser Ala Ser Val Gly
 1                   5                  10                  15

Asp Arg Val Thr Ile Thr Cys Gln Ser Ser Gln Ser Val Tyr Asn Asn
                 20                  25                  30

Asn Asp Leu Ala Trp Tyr Gln Gln Lys Pro Gly Lys Val Pro Lys Leu
             35                  40                  45

Leu Ile Tyr Tyr Ala Ser Thr Leu Ala Ser Gly Val Pro Ser Arg Phe
 50                  55                  60

Ser Gly Ser Gly Ser Gly Thr Asp Phe Thr Leu Thr Ile Ser Ser Leu
 65                  70                  75                  80

Gln Pro Glu Asp Val Ala Thr Tyr Tyr Cys Ala Gly Gly Tyr Asp Thr
                 85                  90                  95

Asp Gly Leu Asp Thr Phe Ala Phe Gly Gly Thr Lys Val Glu Ile
                100                 105                 110

Lys

<210> SEQ ID NO 77
<211> LENGTH: 1353
<212> TYPE: DNA
<213> ORGANISM: Artificial Sequence
<220> FEATURE:
<223> OTHER INFORMATION: synthesized

<400> SEQUENCE: 77
gaggtgcagc tgttggagtc tgggggaggc ttggtacagc ctggggggtc cctgagactc      60
tcctgtgcag cctctggatt caccatcagt cgctaccaca tgacttgggt ccgccaggct     120
```

```
ccagggaagg ggctggagtg gatcggacat atttatgtta ataatgatga cacagactac    180
gcgagctccg cgaaaggccg gttcaccatc tccagagaca attccaagaa cacgctgtat    240
ctgcaaatga acagcctgag agccgaggac acggccacct atttctgtgc gagattggat    300
gttggtggtg gtggtgctta tattggggac atctggggcc agggaaccct ggtcaccgtc    360
tcgagcgcta gcaccaaggg cccatcggtc ttccccctgg cacctcctc caagagcacc    420 tctggggca cagcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
gagcccaaat cttgtgacaa aactcacaca tgcccaccgt gcccagcacc tgaagccgcg    720
ggggcaccgt cagtcttcct cttccccca aacccaagg acaccctcat gatctcccgg    780 accctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcgc ggtctccaac aaagccctcc cagcccccat cgagaaaacc    1020
atctccaaag ccaaagggca gccccgagaa ccacaggtgt acaccctgcc cccatcccgg    1080
gatgagctga ccaagaacca ggtcagcctg acctgcctgg tcaaaggctt ctatcccagc    1140
gacatcgccg tggagtggga gagcaatggg cagccggaga acaactacaa gaccacgcct    1200
cccgtgctgg actccgacgg ctccttcttc ctctatagca agctcaccgt ggacaagagc    1260
aggtggcagc aggggaacgt cttctcatgc tccgtgatgc atgaggctct gcacaaccac    1320
tacacgcaga agagcctctc cctgtctccg ggt                                  1353
```

<210> SEQ ID NO 78
<211> LENGTH: 366
<212> TYPE: DNA
<213> ORGANISM: Artificial Sequence
<220> FEATURE:
<223> OTHER INFORMATION: synthesized

<400> SEQUENCE: 78

```
gaggtgcagc tgttggagtc tgggggaggc ttggtacagc ctgggggtc cctgagactc      60 tcctgtgcag cctctggatt caccatcagt cgctaccaca tgacttgggt ccgccaggct    120
ccagggaagg ggctggagtg gatcggacat atttatgtta ataatgatga cacagactac    180
gcgagctccg cgaaaggccg gttcaccatc tccagagaca attccaagaa cacgctgtat    240
ctgcaaatga acagcctgag agccgaggac acggccacct atttctgtgc gagattggat    300
gttggtggtg gtggtgctta tattggggac atctggggcc agggaaccct ggtcaccgtc    360
tcgagc                                                                366
```

<210> SEQ ID NO 79
<211> LENGTH: 451
<212> TYPE: PRT
<213> ORGANISM: Artificial Sequence
<220> FEATURE:
<223> OTHER INFORMATION: synthesized

<400> SEQUENCE: 79

```
Glu Val Gln Leu Leu Glu Ser Gly Gly Gly Leu Val Gln Pro Gly Gly
 1               5                  10                  15
```

```
Ser Leu Arg Leu Ser Cys Ala Ala Ser Gly Phe Thr Ile Ser Arg Tyr
         20                  25                  30

His Met Thr Trp Val Arg Gln Ala Pro Gly Lys Gly Leu Glu Trp Ile
             35                  40                  45

Gly His Ile Tyr Val Asn Asn Asp Thr Tyr Ala Ser Ser Ala
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Phe Cys
                 85                  90                  95

Ala Arg Leu Asp Val Gly Gly Gly Ala Tyr Ile Gly Asp Ile Trp
             100                 105                 110

Gly Gln Gly Thr Leu Val Thr Val Ser Ser Ala Ser Thr Lys Gly Pro
         115                 120                 125

Ser Val Phe Pro Leu Ala Pro Ser Ser Lys Ser Thr Ser Gly Gly Thr
     130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                 165                 170                 175

Ala Val Leu Gln Ser Ser Gly Leu Tyr Ser Leu Ser Ser Val Val Thr
             180                 185                 190

Val Pro Ser Ser Ser Leu Gly Thr Gln Thr Tyr Ile Cys Asn Val Asn
         195                 200                 205

His Lys Pro Ser Asn Thr Lys Val Asp Lys Arg Val Glu Pro Lys Ser
     210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                 245                 250                 255

Met Ile Ser Arg Thr Pro Glu Val Thr Cys Val Val Val Asp Val Ser
             260                 265                 270

His Glu Asp Pro Glu Val Lys Phe Asn Trp Tyr Val Asp Gly Val Glu
         275                 280                 285

Val His Asn Ala Lys Thr Lys Pro Arg Glu Glu Gln Tyr Asn Ser Thr
     290                 295                 300

Tyr Arg Val Val Ser Val Leu Thr Val Leu His Gln Asp Trp Leu Asn
305                 310                 315                 320

Gly Lys Glu Tyr Lys Cys Ala Val Ser Asn Lys Ala Leu Pro Ala Pro
                 325                 330                 335

Ile Glu Lys Thr Ile Ser Lys Ala Lys Gly Gln Pro Arg Glu Pro Gln
             340                 345                 350

Val Tyr Thr Leu Pro Pro Ser Arg Asp Glu Leu Thr Lys Asn Gln Val
         355                 360                 365

Ser Leu Thr Cys Leu Val Lys Gly Phe Tyr Pro Ser Asp Ile Ala Val
     370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                 405                 410                 415

Val Asp Lys Ser Arg Trp Gln Gln Gly Asn Val Phe Ser Cys Ser Val
             420                 425                 430
```

Met His Glu Ala Leu His Asn His Tyr Thr Gln Lys Ser Leu Ser Leu
            435                 440                 445

Ser Pro Gly
    450

<210> SEQ ID NO 80
<211> LENGTH: 122
<212> TYPE: PRT
<213> ORGANISM: Artificial Sequence
<220> FEATURE:
<223> OTHER INFORMATION: synthesized

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Arg Tyr
            20                  25                  30

His Met Thr Trp Val Arg Gln Ala Pro Gly Lys Gly Leu Glu Trp Ile
        35                  40                  45

Gly His Ile Tyr Val Asn Asn Asp Asp Thr Asp Tyr Ala Ser Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Phe Cys
                85                  90                  95

Ala Arg Leu Asp Val Gly Gly Gly Ala Tyr Ile Gly Asp Ile Trp
            100                 105                 110

Gly Gln Gly Thr Leu Val Thr Val Ser Ser
        115                 120

<210> SEQ ID NO 81
<211> LENGTH: 657
<212> TYPE: DNA
<213> ORGANISM: Artificial Sequence
<220> FEATURE:
<223> OTHER INFORMATION: synthesized

<400> SEQUENCE: 81
gacatccaga tgacccagtc tccatcttcc gtgtctgcat ctgtaggaga cagagtcacc      60
atcacttgtc aggccagtca gaacattggt agtgatttag cctggtatca gcagaaacca     120
gggaaagccc ctaagctcct gatctatact acatccaatc tggcatctgg ggtcccatca     180
aggttcagcg gcagtggatc tgggacagat tcactctcca ccatcagcag cctgcagcct     240
gaagattttg caacttacta ttgtcaaggc ggttatttta gtggtcgtaa tatttatggg     300
aatgctttcg gcggagggac caaggtggag atcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt       657

<210> SEQ ID NO 82
<211> LENGTH: 336
<212> TYPE: DNA
<213> ORGANISM: Artificial Sequence
<220> FEATURE:
<223> OTHER INFORMATION: synthesized

<400> SEQUENCE: 82

```
gacatccaga tgacccagtc tccatcttcc gtgtctgcat ctgtaggaga cagagtcacc    60
atcacttgtc aggccagtca gaacattggt agtgatttag cctggtatca gcagaaacca   120
gggaaagccc ctaagctcct gatctatact acatccaatc tggcatctgg ggtcccatca   180
aggttcagcg gcagtggatc tgggacagat ttcactctca ccatcagcag cctgcagcct   240
gaagattttg caacttacta ttgtcaaggc ggttatttta gtggtcgtaa tatttatggg   300
aatgctttcg gcggagggac caaggtggag atcaaa                             336
```

<210> SEQ ID NO 83
<211> LENGTH: 219
<212> TYPE: PRT
<213> ORGANISM: Artificial Sequence
<220> FEATURE:
<223> OTHER INFORMATION: synthesized

<400> SEQUENCE: 83

```
Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Gly Ser Asp
            20                  25                  30

Leu Ala Trp Tyr Gln Gln Lys Pro Gly Lys Ala Pro Lys Leu Leu Ile
        35                  40                  45

Tyr Thr Thr Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Gly Tyr Phe Ser Gly Arg
                85                  90                  95

Asn Ile Tyr Gly Asn Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 84
<211> LENGTH: 112
<212> TYPE: PRT
<213> ORGANISM: Artificial Sequence
<220> FEATURE:
<223> OTHER INFORMATION: synthesized

<400> SEQUENCE: 84

```
Asp Ile Gln Met Thr Gln Ser Pro Ser Ser Val Ser Ala Ser Val Gly
1               5                   10                  15
```

Asp Arg Val Thr Ile Thr Cys Gln Ala Ser Gln Asn Ile Gly Ser Asp
            20                  25                  30

Leu Ala Trp Tyr Gln Gln Lys Pro Gly Lys Ala Pro Lys Leu Leu Ile
        35                  40                  45

Tyr Thr Thr Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Gly Tyr Phe Ser Gly Arg
                85                  90                  95

Asn Ile Tyr Gly Asn Ala Phe Gly Gly Gly Thr Lys Val Glu Ile Lys
            100                 105                 110

<210> SEQ ID NO 85
<211> LENGTH: 1332
<212> TYPE: DNA
<213> ORGANISM: Artificial Sequence
<220> FEATURE:
<223> OTHER INFORMATION: synthesized

<400> SEQUENCE: 85
gaggtgcagc tggtggagtc tgggggaggc ttggtccagc ctggggggtc cctgagactc      60
tcctgtgcag cctctggatt ctccctcagt ggcgctggag tgagctgggt ccgccaggct     120
ccagggaagg ggctggagtg gatcgggtac attgatagtg gtgctaccac atactacgcg     180
agcagtgcaa aaggcagatt caccatctcc agagacaatt ccaagaacac gctgtatctt     240
caaatgaaca gcctgagagc cgaggacacg gctgtgtatt actgtgcgag aggatactac     300
ggcatggacc cctggggcca gggaaccctg gtcaccgtct cgagcgctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagagagttg agcccaaatc ttgtgacaaa     660
actcacacat gcccaccgtg cccagcacct gaagccgcgg ggcaccgtca gtcttcctc     720
ttcccccccaa aacccaagga caccctcatg atctcccgga ccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcgcg     960
gtctccaaca aagccctccc agcccccatc gagaaaacca tctccaaagc caagggcag    1020
ccccgagaac cacaggtgta caccctgccc ccatcccggg atgagctgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gt                                                        1332

<210> SEQ ID NO 86
<211> LENGTH: 345
<212> TYPE: DNA

<213> ORGANISM: Artificial Sequence
<220> FEATURE:
<223> OTHER INFORMATION: synthesized

<400> SEQUENCE: 86

```
gaggtgcagc tggtggagtc tgggggaggc ttggtccagc ctgggggtc cctgagactc        60 tcctgtgcag cctctggatt ctccctcagt ggcgctggag tgagctgggt ccgccaggct      120
ccagggaagg ggctggagtg gatcgggtac attgatagtg gtgctaccac atactacgcg      180
agcagtgcaa aaggcagatt caccatctcc agagacaatt ccaagaacac gctgtatctt      240
caaatgaaca gcctgagagc cgaggacacg gctgtgtatt actgtgcgag aggatactac      300
ggcatggacc cctggggcca gggaaccctg gtcaccgtct cgagc                      345
```

<210> SEQ ID NO 87
<211> LENGTH: 444
<212> TYPE: PRT
<213> ORGANISM: Artificial Sequence
<220> FEATURE:
<223> OTHER INFORMATION: synthesized

<400> SEQUENCE: 87

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Ser | Leu | Ser | Gly | Ala |
| | | 20 | | | | | 25 | | | | | 30 | | | |

| Gly | Val | Ser | Trp | Val | Arg | Gln | Ala | Pro | Gly | Lys | Gly | Leu | Glu | Trp | Ile |
| | | | 35 | | | | | 40 | | | | | 45 | | |

| Gly | Tyr | Ile | Asp | Ser | Gly | Ala | Thr | Thr | Tyr | Tyr | Ala | Ser | Ser | Ala | Lys |
| | 50 | | | | | 55 | | | | | 60 | | | | |

| Gly | Arg | Phe | Thr | Ile | Ser | Arg | Asp | Asn | Ser | Lys | Asn | Thr | Leu | Tyr | Leu |
| 65 | | | | | 70 | | | | | 75 | | | | | 80 |

| Gln | Met | Asn | Ser | Leu | Arg | Ala | Glu | Asp | Thr | Ala | Val | Tyr | Tyr | Cys | Ala |
| | | | | 85 | | | | | 90 | | | | | 95 | |

| Arg | Gly | Tyr | Tyr | Gly | Met | Asp | Pro | Trp | Gly | Gln | Gly | Thr | Leu | Val | Thr |
| | | | 100 | | | | | 105 | | | | | 110 | | |

| Val | Ser | Ser | Ala | Ser | Thr | Lys | Gly | Pro | Ser | Val | Phe | Pro | Leu | Ala | Pro |
| | | | 115 | | | | | 120 | | | | | 125 | | |

| Ser | Ser | Lys | Ser | Thr | Ser | Gly | Gly | Thr | Ala | Ala | Leu | Gly | Cys | Leu | Val |
| | 130 | | | | | 135 | | | | | 140 | | | | |

| Lys | Asp | Tyr | Phe | Pro | Glu | Pro | Val | Thr | Val | Ser | Trp | Asn | Ser | Gly | Ala |
| 145 | | | | | 150 | | | | | 155 | | | | | 160 |

| Leu | Thr | Ser | Gly | Val | His | Thr | Phe | Pro | Ala | Val | Leu | Gln | Ser | Ser | Gly |
| | | | | 165 | | | | | 170 | | | | | 175 | |

| Leu | Tyr | Ser | Leu | Ser | Ser | Val | Val | Thr | Val | Pro | Ser | Ser | Ser | Leu | Gly |
| | | | 180 | | | | | 185 | | | | | 190 | | |

| Thr | Gln | Thr | Tyr | Ile | Cys | Asn | Val | Asn | His | Lys | Pro | Ser | Asn | Thr | Lys |
| | | | 195 | | | | | 200 | | | | | 205 | | |

| Val | Asp | Lys | Arg | Val | Glu | Pro | Lys | Ser | Cys | Asp | Lys | Thr | His | Thr | Cys |
| | 210 | | | | | 215 | | | | | 220 | | | | |

| Pro | Pro | Cys | Pro | Ala | Pro | Glu | Ala | Ala | Gly | Ala | Pro | Ser | Val | Phe | Leu |
| 225 | | | | | 230 | | | | | 235 | | | | | 240 |

| Phe | Pro | Pro | Lys | Pro | Lys | Asp | Thr | Leu | Met | Ile | Ser | Arg | Thr | Pro | Glu |
| | | | | 245 | | | | | 250 | | | | | 255 | |

| Val | Thr | Cys | Val | Val | Val | Asp | Val | Ser | His | Glu | Asp | Pro | Glu | Val | Lys |
| | | | 260 | | | | | 265 | | | | | 270 | | |

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 88
<211> LENGTH: 115
<212> TYPE: PRT
<213> ORGANISM: Artificial Sequence
<220> FEATURE:
<223> OTHER INFORMATION: synthesized

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Gly Ala
            20                  25                  30

Gly Val Ser Trp Val Arg Gln Ala Pro Gly Lys Gly Leu Glu Trp Ile
        35                  40                  45

Gly Tyr Ile Asp Ser Gly Ala Thr Thr Tyr Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Tyr Gly Met Asp Pro Trp Gly Gln Gly Thr Leu Val Thr
            100                 105                 110

Val Ser Ser
    115

<210> SEQ ID NO 89
<211> LENGTH: 1332
<212> TYPE: DNA
<213> ORGANISM: Artificial Sequence
<220> FEATURE:
<223> OTHER INFORMATION: synthesized

<400> SEQUENCE: 89
gaggtgcagc tggtggagtc tgggggaggc ttggtccagc ctggggggtc cctgagactc       60

```
tcctgtacag cctctggatt ctccctcagt ggcgctggag tgagctgggt ccgccaggct      120
ccagggaagg ggctggagtg gatcgggtac attgatagtg gtgctaccac atactacgcg      180
agcagtgcaa aaggcagatt caccatctcc aaagacaatg ccaagaacac ggtggatctt      240
caaatgaaca gcctgagagc cgaggacacg gctgtgtatt actgtgcgag aggatactac      300
ggcatggacc cctggggcca gggaaccctg gtcaccgtct cgagcgctag caccaagggc      360
ccatcggtct tccccctggc accctcctcc aagagcacct ctgggggcac agcggccctg      420
ggctgcctgg tcaaggacta cttccccgaa ccggtgacgg tgtcgtggaa ctcaggcgcc      480
ctgaccagcg gcgtgcacac cttcccggct gtcctacagt cctcaggact ctactccctc      540
agcagcgtgg tgaccgtgcc ctccagcagc ttgggcaccc agacctacat ctgcaacgtg      600
aatcacaagc ccagcaacac caaggtggac aagagagttg agcccaaatc ttgtgacaaa      660
actcacacat gcccaccgtg cccagcacct gaagccgcgg ggcaccgtc agtcttcctc       720 ttccccccaa acccaagga caccctcatg atctcccgga cccctgaggt cacatgcgtg      780
gtggtggacg tgagccacga agaccctgag gtcaagttca actggtacgt ggacggcgtg      840
gaggtgcata atgccaagac aaagccgcgg gaggagcagt acaacagcac gtaccgtgtg      900
gtcagcgtcc tcaccgtcct gcaccaggac tggctgaatg gcaaggagta caagtgcgcg      960
gtctccaaca agccctccc agccccatc gagaaaacca tctccaaagc caagggcag     1020 ccccgagaac cacaggtgta caccctgccc ccatcccggg atgagctgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gt                                                        1332
```

<210> SEQ ID NO 90
<211> LENGTH: 345
<212> TYPE: DNA
<213> ORGANISM: Artificial Sequence
<220> FEATURE:
<223> OTHER INFORMATION: synthesized

<400> SEQUENCE: 90

```
gaggtgcagc tggtggagtc tgggggaggc ttggtccagc ctggggggtc cctgagactc       60
tcctgtacag cctctggatt ctccctcagt ggcgctggag tgagctgggt ccgccaggct      120
ccagggaagg ggctggagtg gatcgggtac attgatagtg gtgctaccac atactacgcg      180
agcagtgcaa aaggcagatt caccatctcc aaagacaatg ccaagaacac ggtggatctt      240
caaatgaaca gcctgagagc cgaggacacg gctgtgtatt actgtgcgag aggatactac      300
ggcatggacc cctggggcca gggaaccctg gtcaccgtct cgagc                      345
```

<210> SEQ ID NO 91
<211> LENGTH: 444
<212> TYPE: PRT
<213> ORGANISM: Artificial Sequence
<220> FEATURE:
<223> OTHER INFORMATION: synthesized

<400> SEQUENCE: 91

```
Glu Val Gln Leu Val Glu Ser Gly Gly Gly Leu Val Gln Pro Gly Gly
1               5                   10                  15
```

```
Ser Leu Arg Leu Ser Cys Thr Ala Ser Gly Phe Ser Leu Ser Gly Ala
             20                  25                  30

Gly Val Ser Trp Val Arg Gln Ala Pro Gly Lys Gly Leu Glu Trp Ile
         35                  40                  45

Gly Tyr Ile Asp Ser Gly Ala Thr Thr Tyr Tyr Ala Ser Ser Ala Lys
     50                  55                  60

Gly Arg Phe Thr Ile Ser Lys Asp Asn Ala Lys Asn Thr Val Asp Leu
 65                  70                  75                  80

Gln Met Asn Ser Leu Arg Ala Glu Asp Thr Ala Val Tyr Tyr Cys Ala
                 85                  90                  95

Arg Gly Tyr Tyr Gly Met Asp Pro Trp Gly Gln Gly Thr Leu Val Thr
             100                 105                 110

Val Ser Ser Ala Ser Thr Lys Gly Pro Ser Val Phe Pro Leu Ala Pro
         115                 120                 125

Ser Ser Lys Ser Thr Ser Gly Gly Thr Ala Ala Leu Gly Cys Leu Val
     130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                 165                 170                 175

Leu Tyr Ser Leu Ser Ser Val Val Thr Val Pro Ser Ser Ser Leu Gly
             180                 185                 190

Thr Gln Thr Tyr Ile Cys Asn Val Asn His Lys Pro Ser Asn Thr Lys
         195                 200                 205

Val Asp Lys Arg Val Glu Pro Lys Ser Cys Asp Lys Thr His Thr Cys
 210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                 245                 250                 255

Val Thr Cys Val Val Val Asp Val Ser His Glu Asp Pro Glu Val Lys
             260                 265                 270

Phe Asn Trp Tyr Val Asp Gly Val Glu Val His Asn Ala Lys Thr Lys
         275                 280                 285

Pro Arg Glu Glu Gln Tyr Asn Ser Thr Tyr Arg Val Val Ser Val Leu
 290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                 325                 330                 335

Ala Lys Gly Gln Pro Arg Glu Pro Gln Val Tyr Thr Leu Pro Pro Ser
             340                 345                 350

Arg Asp Glu Leu Thr Lys Asn Gln Val Ser Leu Thr Cys Leu Val Lys
         355                 360                 365

Gly Phe Tyr Pro Ser Asp Ile Ala Val Glu Trp Glu Ser Asn Gly Gln
 370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                 405                 410                 415

Gln Gly Asn Val Phe Ser Cys Ser Val Met His Glu Ala Leu His Asn
             420                 425                 430

His Tyr Thr Gln Lys Ser Leu Ser Leu Ser Pro Gly
```

<210> SEQ ID NO 92
<211> LENGTH: 115
<212> TYPE: PRT
<213> ORGANISM: Artificial Sequence
<220> FEATURE:
<223> OTHER INFORMATION: synthesized

<400> SEQUENCE: 92

```
Glu Val Gln Leu Val Glu Ser Gly Gly Gly Leu Val Gln Pro Gly Gly
 1               5                  10                  15
Ser Leu Arg Leu Ser Cys Thr Ala Ser Gly Phe Ser Leu Ser Gly Ala
            20                  25                  30
Gly Val Ser Trp Val Arg Gln Ala Pro Gly Lys Gly Leu Glu Trp Ile
        35                  40                  45
Gly Tyr Ile Asp Ser Gly Ala Thr Thr Tyr Tyr Ala Ser Ser Ala Lys
    50                  55                  60
Gly Arg Phe Thr Ile Ser Lys Asp Asn Ala Lys Asn Thr Val Asp Leu
65                  70                  75                  80
Gln Met Asn Ser Leu Arg Ala Glu Asp Thr Ala Val Tyr Tyr Cys Ala
                85                  90                  95
Arg Gly Tyr Tyr Gly Met Asp Pro Trp Gly Gln Gly Thr Leu Val Thr
            100                 105                 110
Val Ser Ser
        115
```

<210> SEQ ID NO 93
<211> LENGTH: 657
<212> TYPE: DNA
<213> ORGANISM: Artificial Sequence
<220> FEATURE:
<223> OTHER INFORMATION: synthesized

<400> SEQUENCE: 93

```
gccatcgatt tgacccagtc tccttccacc ctgtctgcat ctgtaggagg cacaatcacc    60
atcaattgcc aagccagtga gagcattagc agttggttag cctggtatca gcagaaacca   120
gggaaagccc ctaagctcct gatctatgaa acatccaaac tggcatctgg ggtcccatca   180
aggttcagcg gcagtggatc tgggacagag ttcactctca ccatcagcag cctgcagcct   240
gatgattttg caacttatta ctgccaaagt tattatcgta ttaataatat tggttacgat   300
aatgctttcg gcggagggac caaggtggag atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt      657
```

<210> SEQ ID NO 94
<211> LENGTH: 259
<212> TYPE: DNA
<213> ORGANISM: Artificial Sequence
<220> FEATURE:
<223> OTHER INFORMATION: synthesized

<400> SEQUENCE: 94

```
tgagagcatt agcagttggt tagcctggta tcagcagaaa ccagggaaag cccctaagct    60
```

-continued

```
cctgatctat gaaacatcca aactggcatc tggggtccca tcaaggttca gcggcagtgg      120
atctgggaca gagttcactc tcaccatcag cagcctgcag cctgatgatt ttgcaactta      180
ttactgccaa agttattatc gtattaataa tattggttac gataatgctt tcggcggagg      240
gaccaaggtg gagatcaaa                                                   259
```

<210> SEQ ID NO 95
<211> LENGTH: 219
<212> TYPE: PRT
<213> ORGANISM: Artificial Sequence
<220> FEATURE:
<223> OTHER INFORMATION: synthesized

<400> SEQUENCE: 95

```
Ala Ile Asp Leu Thr Gln Ser Pro Ser Thr Leu Ser Ala Ser Val Gly
1               5                   10                  15

Gly Thr Ile Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Thr Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Tyr Tyr Arg Ile Asn Asn
                85                  90                  95

Ile Gly Tyr Asp Asn Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 96
<211> LENGTH: 112
<212> TYPE: PRT
<213> ORGANISM: Artificial Sequence
<220> FEATURE:
<223> OTHER INFORMATION: synthesized

<400> SEQUENCE: 96

```
Ala Ile Asp Leu Thr Gln Ser Pro Ser Thr Leu Ser Ala Ser Val Gly
1               5                   10                  15

Gly Thr Ile Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45
```

Tyr Glu Thr Ser Lys Leu Ala Ser Gly Val Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Ser Tyr Arg Ile Asn Asn
                85                  90                  95

Ile Gly Tyr Asp Asn Ala Phe Gly Gly Gly Thr Lys Val Glu Ile Lys
                100                 105                 110

<210> SEQ ID NO 97
<211> LENGTH: 1335
<212> TYPE: DNA
<213> ORGANISM: Artificial Sequence
<220> FEATURE:
<223> OTHER INFORMATION: synthesized

<400> SEQUENCE: 97
gaggtgcagc tggtggagtc tgggggaggc ttggtccagc ctggggggtc cctgagactc     60
tcctgtaccg cctctggatt ctccctcagt aggaatgcaa tgaactgggt ccgccaggct    120
ccagggaagg ggctggagta catcggatac attagcacta gtggtaccac attctacgcg    180
aacagcgtga aggcagatt caccatctcc aaagacaata ccaagaacac ggtggatctt    240
caaatgaaca gcctgagagc cgaggacacg gctgtgtatt actgtgcgag agactataac    300
tacgccatgg acatctgggg ccagggaacc ctggtcaccg tctcgagcgc tagcaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagagag ttgagcccaa atcttgtgac    660
aaaactcaca catgcccacc gtgcccagca cctgaagccg cggggcacc gtcagtcttc    720 ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
gcggtctcca acaaagccct cccagccccc atcgagaaaa ccatctccaa agccaaaggg   1020
cagccccgag aaccacaggt gtacaccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctatag caagctcacc gtggacaaga gcaggtggca gcagggaac   1260 gtcttctcat gctccgtgat gcatgaggct ctgcacaacc actacacgca gaagagcctc   1320
tccctgtctc cgggt                                                    1335

<210> SEQ ID NO 98
<211> LENGTH: 348
<212> TYPE: DNA
<213> ORGANISM: Artificial Sequence
<220> FEATURE:
<223> OTHER INFORMATION: synthesized

<400> SEQUENCE: 98

```
gaggtgcagc tggtggagtc tggggggaggc ttggtccagc ctgggggtc cctgagactc    60 tcctgtaccg cctctggatt ctccctcagt aggaatgcaa tgaactgggt ccgccaggct   120
ccagggaagg ggctggagta catcggatac attagcacta gtggtaccac attctacgcg   180
aacagcgtga aaggcagatt caccatctcc aaagacaata ccaagaacac ggtggatctt   240
caaatgaaca gcctgagagc cgaggacacg gctgtgtatt actgtgcgag agactataac   300
tacgccatgg acatctgggg ccagggaacc ctggtcaccg tctcgagc                348
```

<210> SEQ ID NO 99
<211> LENGTH: 445
<212> TYPE: PRT
<213> ORGANISM: Artificial Sequence
<220> FEATURE:
<223> OTHER INFORMATION: synthesized

<400> SEQUENCE: 99

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Arg Asn
            20                  25                  30

Ala Met Asn Trp Val Arg Gln Ala Pro Gly Lys Gly Leu Glu Tyr Ile
        35                  40                  45

Gly Tyr Ile Ser Thr Ser Gly Thr Thr Phe Tyr Ala Asn Ser Val Lys
    50                  55                  60

Gly Arg Phe Thr Ile Ser Lys Asp Asn Thr Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Asp Tyr Asn Tyr Ala Met Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

Leu Thr Val Leu His Gln Asp Trp Leu Asn Gly Lys Glu Tyr Lys Cys
305                 310                 315                 320

Ala Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly
            435                 440                 445

<210> SEQ ID NO 100
<211> LENGTH: 116
<212> TYPE: PRT
<213> ORGANISM: Artificial Sequence
<220> FEATURE:
<223> OTHER INFORMATION: synthesized

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Arg Asn
            20                  25                  30

Ala Met Asn Trp Val Arg Gln Ala Pro Gly Lys Gly Leu Glu Tyr Ile
        35                  40                  45

Gly Tyr Ile Ser Thr Ser Gly Thr Thr Phe Tyr Ala Asn Ser Val Lys
    50                  55                  60

Gly Arg Phe Thr Ile Ser Lys Asp Asn Thr Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Asp Tyr Asn Tyr Ala Met Asp Ile Trp Gly Gln Gly Thr Leu Val
            100                 105                 110

Thr Val Ser Ser
        115

<210> SEQ ID NO 101
<211> LENGTH: 648
<212> TYPE: DNA
<213> ORGANISM: Artificial Sequence
<220> FEATURE:
<223> OTHER INFORMATION: synthesized

<400> SEQUENCE: 101
gacatccaga tgacccagtc tccatcctcc ctgtctgcat ctgtaggaga cagagtcacc    60
atcacttgcc agtccagtca gagtgttaac aacaacgact tagcctggta tcagcagaaa   120
ccagggaaag cccctaagcg cctgatctat tgggcatcca aactggcatc tggggtccca   180
tcaaggttca gcggcagtgg atctgggaca gaattcactc tcacaatcag caacctgcag   240

```
cctgaagatt ttgcaactta ttactgtgca ggcggttata gtggtaatat ttatggtttc    300
ggcggaggga ccaaggtgga gatcaaacgt acggtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt                 648
```

<210> SEQ ID NO 102
<211> LENGTH: 327
<212> TYPE: DNA
<213> ORGANISM: Artificial Sequence
<220> FEATURE:
<223> OTHER INFORMATION: synthesized

<400> SEQUENCE: 102

```
gacatccaga tgacccagtc tccatcctcc ctgtctgcat ctgtaggaga cagagtcacc     60
atcacttgcc agtccagtca gagtgttaac aacaacgact tagcctggta tcagcagaaa    120
ccagggaaag cccctaagcg cctgatctat tgggcatcca aactggcatc tggggtccca    180
tcaaggttca gcggcagtgg atctgggaca gaattcactc tcacaatcag caacctgcag    240
cctgaagatt ttgcaactta ttactgtgca ggcggttata gtggtaatat ttatggtttc    300
ggcggaggga ccaaggtgga gatcaaa                                        327
```

<210> SEQ ID NO 103
<211> LENGTH: 216
<212> TYPE: PRT
<213> ORGANISM: Artificial Sequence
<220> FEATURE:
<223> OTHER INFORMATION: synthesized

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Asn Asn Asn
            20                  25                  30

Asp Leu Ala Trp Tyr Gln Gln Lys Pro Gly Lys Ala Pro Lys Arg Leu
        35                  40                  45

Ile Tyr Trp Ala Ser Lys Leu Ala Ser Gly Val Pro Ser Arg Phe Ser
    50                  55                  60

Gly Ser Gly Ser Gly Thr Glu Phe Thr Leu Thr Ile Ser Asn Leu Gln
65                  70                  75                  80

Pro Glu Asp Phe Ala Thr Tyr Tyr Cys Ala Gly Gly Tyr Ser Gly Asn
                85                  90                  95

Ile Tyr Gly Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 104
<211> LENGTH: 109
<212> TYPE: PRT
<213> ORGANISM: Artificial Sequence
<220> FEATURE:
<223> OTHER INFORMATION: synthesized

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Asn Asn Asn
            20                  25                  30

Asp Leu Ala Trp Tyr Gln Gln Lys Pro Gly Lys Ala Pro Lys Arg Leu
        35                  40                  45

Ile Tyr Trp Ala Ser Lys Leu Ala Ser Gly Val Pro Ser Arg Phe Ser
    50                  55                  60

Gly Ser Gly Ser Gly Thr Glu Phe Thr Leu Thr Ile Ser Asn Leu Gln
65                  70                  75                  80

Pro Glu Asp Phe Ala Thr Tyr Tyr Cys Ala Gly Gly Tyr Ser Gly Asn
                85                  90                  95

Ile Tyr Gly Phe Gly Gly Gly Thr Lys Val Glu Ile Lys
            100                 105

<210> SEQ ID NO 105
<211> LENGTH: 1320
<212> TYPE: DNA
<213> ORGANISM: Artificial Sequence
<220> FEATURE:
<223> OTHER INFORMATION: synthesized

<400> SEQUENCE: 105
cagtcggtgg aggagtctgg gggaggcttg gtccagcctg ggggtccct gagactctcc      60 tgtaccgcct ctggattctc cctcagtaac aatgcaataa cctgggtccg ccaggctcca    120
gggaaggggc tggagtacat cggaatcatt agtagtagtg gtaccacata ctacgcgagc    180
tccgcgaaag gcagattcac catctccaaa gacacctcca agaacacggt ggatcttcaa    240
atgaacagcc tgagagccga ggacacggct gtgtattact gtgcgggagc atttagcgtc    300
tggggccagg gaaccctggt caccgtctcg agcgctagca ccaagggccc atcggtcttc    360
cccctggcac cctcctccaa gagcacctct ggggcacag cggccctggg ctgcctggtc     420
aaggactact ccccgaacc ggtgacggtg tcgtggaact caggcgccct gaccagcggc     480
gtgcacacct tcccggctgt cctacagtcc tcaggactct actccctcag cagcgtggtg    540
accgtgccct ccagcagctt gggcacccag acctacatct gcaacgtgaa tcacaagccc    600
agcaacacca aggtggacaa gagagttgag cccaaatctt gtgacaaaac tcacacatgc    660
ccaccgtgcc cagcacctga gccgcgggg gcaccgtcag tcttcctctt ccccccaaaa    720
cccaaggaca cccctcatgat ctcccggacc cctgaggtca catgcgtggt ggtggacgtg   780
agccacgaag accctgaggt caagttcaac tggtacgtgg acggcgtgga ggtgcataat    840
gccaagacaa agccgcggga ggagcagtac aacagcacgt accgtgtggt cagcgtcctc    900

```
accgtcctgc accaggactg gctgaatggc aaggagtaca agtgcgcggt ctccaacaaa    960
gccctcccag cccccatcga gaaaaccatc tccaaagcca agggcagcc ccgagaacca   1020 caggtgtaca ccctgccccc atcccgggat gagctgacca agaaccaggt cagcctgacc   1080
tgcctggtca aaggcttcta tcccagcgac atcgccgtgg agtgggagag caatgggcag   1140
ccggagaaca actacaagac cacgcctccc gtgctggact ccgacggctc cttcttcctc   1200
tatagcaagc tcaccgtgga caagagcagg tggcagcagg ggaacgtctt ctcatgctcc   1260
gtgatgcatg aggctctgca caaccactac acgcagaaga gcctctccct gtctccgggt   1320
```

<210> SEQ ID NO 106
<211> LENGTH: 333
<212> TYPE: DNA
<213> ORGANISM: Artificial Sequence
<220> FEATURE:
<223> OTHER INFORMATION: synthesized

<400> SEQUENCE: 106

```
cagtcggtgg aggagtctgg gggaggcttg gtccagcctg gggggtccct gagactctcc     60
tgtaccgcct ctggattctc cctcagtaac aatgcaataa cctgggtccg ccaggctcca    120
gggaaggggc tggagtacat cggaatcatt agtagtagtg gtaccacata ctacgcgagc    180
tccgcgaaag gcagattcac catctccaaa gacacctcca agaacacggt ggatcttcaa    240
atgaacagcc tgagagccga ggacacggct gtgtattact gtgcgggagc atttagcgtc    300
tggggccagg gaaccctggt caccgtctcg agc                                  333
```

<210> SEQ ID NO 107
<211> LENGTH: 440
<212> TYPE: PRT
<213> ORGANISM: Artificial Sequence
<220> FEATURE:
<223> OTHER INFORMATION: synthesized

<400> SEQUENCE: 107

```
Gln Ser Val Glu Glu Ser Gly Gly Gly Leu Val Gln Pro Gly Gly Ser
1               5                   10                  15

Leu Arg Leu Ser Cys Thr Ala Ser Gly Phe Ser Leu Ser Asn Asn Ala
            20                  25                  30

Ile Thr Trp Val Arg Gln Ala Pro Gly Lys Gly Leu Glu Tyr Ile Gly
        35                  40                  45

Ile Ile Ser Ser Ser Gly Thr Thr Tyr Tyr Ala Ser Ser Ala Lys Gly
    50                  55                  60

Arg Phe Thr Ile Ser Lys Asp Thr Ser Lys Asn Thr Val Asp Leu Gln
65                  70                  75                  80

Met Asn Ser Leu Arg Ala Glu Asp Thr Ala Val Tyr Tyr Cys Ala Gly
                85                  90                  95

Ala Phe Ser Val Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175
```

-continued

```
Ser Ser Val Val Thr Val Pro Ser Ser Leu Gly Thr Gln Thr Tyr
            180                 185                 190

Ile Cys Asn Val Asn His Lys Pro Ser Asn Thr Lys Val Asp Lys Arg
        195                 200                 205

Val Glu Pro Lys Ser Cys Asp Lys Thr His Thr Cys Pro Pro Cys Pro
210                 215                 220

Ala Pro Glu Ala Ala Gly Ala Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
        260                 265                 270

Val Asp Gly Val Glu Val His Asn Ala Lys Thr Lys Pro Arg Glu Glu
    275                 280                 285

Gln Tyr Asn Ser Thr Tyr Arg Val Val Ser Val Leu Thr Val Leu His
290                 295                 300

Gln Asp Trp Leu Asn Gly Lys Glu Tyr Lys Cys Ala Val Ser Asn Lys
305                 310                 315                 320

Ala Leu Pro Ala Pro Ile Glu Lys Thr Ile Ser Lys Ala Lys Gly Gln
            325                 330                 335

Pro Arg Glu Pro Gln Val Tyr Thr Leu Pro Pro Ser Arg Asp Glu Leu
        340                 345                 350

Thr Lys Asn Gln Val Ser Leu Thr Cys Leu Val Lys Gly Phe Tyr Pro
    355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
        420                 425                 430

Lys Ser Leu Ser Leu Ser Pro Gly
            435                 440

<210> SEQ ID NO 108
<211> LENGTH: 111
<212> TYPE: PRT
<213> ORGANISM: Artificial Sequence
<220> FEATURE:
<223> OTHER INFORMATION: synthesized

<400> SEQUENCE: 108

Gln Ser Val Glu Glu Ser Gly Gly Gly Leu Val Gln Pro Gly Gly Ser
1               5                   10                  15

Leu Arg Leu Ser Cys Thr Ala Ser Gly Phe Ser Leu Ser Asn Asn Ala
            20                  25                  30

Ile Thr Trp Val Arg Gln Ala Pro Gly Lys Gly Leu Glu Tyr Ile Gly
        35                  40                  45

Ile Ile Ser Ser Ser Gly Thr Thr Tyr Tyr Ala Ser Ser Ala Lys Gly
    50                  55                  60

Arg Phe Thr Ile Ser Lys Asp Thr Ser Lys Asn Thr Val Asp Leu Gln
65                  70                  75                  80

Met Asn Ser Leu Arg Ala Glu Asp Thr Ala Val Tyr Tyr Cys Ala Gly
            85                  90                  95
```

Ala Phe Ser Val Trp Gly Gln Gly Thr Leu Val Thr Val Ser Ser
            100                 105                 110

<210> SEQ ID NO 109
<211> LENGTH: 660
<212> TYPE: DNA
<213> ORGANISM: Artificial Sequence
<220> FEATURE:
<223> OTHER INFORMATION: synthesized

<400> SEQUENCE: 109
gacatccaga tgacccagtc tccttccacc ctgtctgcat ctgtaggaga cagagtcacc    60
atcacttgcc aggccagtca gagcattgat agttggttat cctggtatca gcagaaacca   120
gggaaagccc ctaagctcct gatctatcag gcatccactc tggcatctgg ggtcccatca   180
aggttcagcg gcagtggatc tgggacagag ttcactctca ccatcagcag cctgcagcct   240
gatgattttg caacttatta ctgccaatct gcttatggtg ttagtggtac tagtagttat   300
ttatatactt tcggcggagg gaccaaggtg gagatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660

<210> SEQ ID NO 110
<211> LENGTH: 339
<212> TYPE: DNA
<213> ORGANISM: Artificial Sequence
<220> FEATURE:
<223> OTHER INFORMATION: synthesized

<400> SEQUENCE: 110
gacatccaga tgacccagtc tccttccacc ctgtctgcat ctgtaggaga cagagtcacc    60
atcacttgcc aggccagtca gagcattgat agttggttat cctggtatca gcagaaacca   120
gggaaagccc ctaagctcct gatctatcag gcatccactc tggcatctgg ggtcccatca   180
aggttcagcg gcagtggatc tgggacagag ttcactctca ccatcagcag cctgcagcct   240
gatgattttg caacttatta ctgccaatct gcttatggtg ttagtggtac tagtagttat   300
ttatatactt tcggcggagg gaccaaggtg gagatcaaa                          339

<210> SEQ ID NO 111
<211> LENGTH: 220
<212> TYPE: PRT
<213> ORGANISM: Artificial Sequence
<220> FEATURE:
<223> OTHER INFORMATION: synthesized

<400> SEQUENCE: 111

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asp Ser Trp
            20                  25                  30

Leu Ser Trp Tyr Gln Gln Lys Pro Gly Lys Ala Pro Lys Leu Leu Ile
        35                  40                  45

Tyr Gln Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Ala Tyr Gly Val Ser Gly
                85                  90                  95

Thr Ser Ser Tyr Leu Tyr Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 112
<211> LENGTH: 113
<212> TYPE: PRT
<213> ORGANISM: Artificial Sequence
<220> FEATURE:
<223> OTHER INFORMATION: synthesized

<400> SEQUENCE: 112

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asp Ser Trp
            20                  25                  30

Leu Ser Trp Tyr Gln Gln Lys Pro Gly Lys Ala Pro Lys Leu Leu Ile
        35                  40                  45

Tyr Gln Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Ala Tyr Gly Val Ser Gly
                85                  90                  95

Thr Ser Ser Tyr Leu Tyr Thr Phe Gly Gly Gly Thr Lys Val Glu Ile
            100                 105                 110

Lys

<210> SEQ ID NO 113
<211> LENGTH: 1344
<212> TYPE: DNA
<213> ORGANISM: Artificial Sequence
<220> FEATURE:
<223> OTHER INFORMATION: synthesized

<400> SEQUENCE: 113
cagtcgctgg tggagtctgg gggaggcttg gtccagcctg ggggtccct gagactctcc      60 tgtacagcct ctggattctc cctcagtagg tactacatga cctgggtccg ccaggctcca    120
gggaaggggc tggagtggat cggaaccatt tatactagtg gtagtacatg gtacgcgagc    180

```
tggacaaaag gcagattcac catctccaaa gacaatacca agaacacggt ggatcttcaa      240
atgaacagcc tgagagccga ggacacggct gtgtattact gtgcgagatc ctattatggc      300
ggtgataaga ctggtttagg catctggggc cagggaaccc tggtcaccgt ctcgagcgct      360
agcaccaagg gcccatcggt cttccccctg gcacctcct ccaagagcac ctctgggggc       420
acagcggccc tgggctgcct ggtcaaggac tacttccccg aaccggtgac ggtgtcgtgg      480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaagccgc ggggggcaccg    720 tcagtcttcc tcttcccccc aaaacccaag gacaccctca tgatctcccg gaccccgag    780 gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgcg cggtctccaa caaagccctc ccagccccca tcgagaaaac catctccaaa   1020
gccaaagggc agccccgaga accacaggtg tacaccctgc ccccatcccg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctatagc aagctcaccg tggacaagag caggtggcag   1260
caggggaacg tcttctcatg ctccgtgatg catgaggctc tgcacaacca ctacacgcag   1320
aagagcctct ccctgtctcc gggt                                           1344

<210> SEQ ID NO 114
<211> LENGTH: 357
<212> TYPE: DNA
<213> ORGANISM: Artificial Sequence
<220> FEATURE:
<223> OTHER INFORMATION: synthesized

<400> SEQUENCE: 114
cagtcgctgg tggagtctgg gggaggcttg gtccagcctg gggggtccct gagactctcc       60
tgtacagcct ctggattctc cctcagtagg tactacatga cctgggtccg ccaggctcca     120 gggaagggc tggagtggat cggaaccatt tatactagtg gtagtacatg gtacgcgagc      180
tggacaaaag gcagattcac catctccaaa gacaatacca agaacacggt ggatcttcaa     240
atgaacagcc tgagagccga ggacacggct gtgtattact gtgcgagatc ctattatggc     300
ggtgataaga ctggtttagg catctggggc cagggaaccc tggtcaccgt ctcgagc        357

<210> SEQ ID NO 115
<211> LENGTH: 448
<212> TYPE: PRT
<213> ORGANISM: Artificial Sequence
<220> FEATURE:
<223> OTHER INFORMATION: synthesized

<400> SEQUENCE: 115

Gln Ser Leu Val Glu Ser Gly Gly Gly Leu Val Gln Pro Gly Gly Ser
 1               5                  10                  15

Leu Arg Leu Ser Cys Thr Ala Ser Gly Phe Ser Leu Ser Arg Tyr Tyr
            20                  25                  30
```

```
Met Thr Trp Val Arg Gln Ala Pro Gly Lys Gly Leu Glu Trp Ile Gly
         35                  40                  45
Thr Ile Tyr Thr Ser Gly Ser Thr Trp Tyr Ala Ser Trp Thr Lys Gly
 50                  55                  60
Arg Phe Thr Ile Ser Lys Asp Asn Thr Lys Asn Thr Val Asp Leu Gln
 65                  70                  75                  80
Met Asn Ser Leu Arg Ala Glu Asp Thr Ala Val Tyr Tyr Cys Ala Arg
                 85                  90                  95
Ser Tyr Tyr Gly Gly Asp Lys Thr Gly Leu Gly Ile Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
        210                 215                 220
Thr His Thr Cys Pro Pro Cys Pro Ala Pro Glu Ala Ala Gly Ala Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Ala Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
```

<210> SEQ ID NO 116
<211> LENGTH: 119
<212> TYPE: PRT
<213> ORGANISM: Artificial Sequence
<220> FEATURE:
<223> OTHER INFORMATION: synthesized

<400> SEQUENCE: 116

Gln Ser Leu Val Glu Ser Gly Gly Leu Val Gln Pro Gly Gly Ser
1               5                   10                  15

Leu Arg Leu Ser Cys Thr Ala Ser Gly Phe Ser Leu Ser Arg Tyr Tyr
            20                  25                  30

Met Thr Trp Val Arg Gln Ala Pro Gly Lys Gly Leu Glu Trp Ile Gly
        35                  40                  45

Thr Ile Tyr Thr Ser Gly Ser Thr Trp Tyr Ala Ser Trp Thr Lys Gly
    50                  55                  60

Arg Phe Thr Ile Ser Lys Asp Asn Thr Lys Asn Thr Val Asp Leu Gln
65              70                  75                  80

Met Asn Ser Leu Arg Ala Glu Asp Thr Ala Val Tyr Tyr Cys Ala Arg
                85                  90                  95

Ser Tyr Tyr Gly Gly Asp Lys Thr Gly Leu Gly Ile Trp Gly Gln Gly
            100                 105                 110

Thr Leu Val Thr Val Ser Ser
        115

<210> SEQ ID NO 117
<211> LENGTH: 642
<212> TYPE: DNA
<213> ORGANISM: Artificial Sequence
<220> FEATURE:
<223> OTHER INFORMATION: synthesized

<400> SEQUENCE: 117
gacatccaga tgacccagtc tccatcctcc ctgtctgcat ctgtaggaga cagagtcacc    60
atcaattgcc aggccagtca gaacatttac agctacttat cctggtatca gcagaaacca   120
gggaaagttc ctaagcgcct gatctatctg catctactc tggcatctgg ggtcccatct    180
cggttcagtg gcagtggatc tgggacagat tacactctca ccatcagcag cctgcagcct   240
gaagatgttg caacttatta ctgtcaaagc aattataacg gtaattatgg tttcggcgga   300
gggaccaagg tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacccctgacg   540 ctgagcaaag cagactacga aaacacaaa gtctacgcct gcgaagtcac ccatcagggc   600
ctgagctcgc ccgtcacaaa gagcttcaac aggggagagt gt                      642

<210> SEQ ID NO 118
<211> LENGTH: 321
<212> TYPE: DNA
<213> ORGANISM: Artificial Sequence
<220> FEATURE:
<223> OTHER INFORMATION: synthesized

<400> SEQUENCE: 118
gacatccaga tgacccagtc tccatcctcc ctgtctgcat ctgtaggaga cagagtcacc    60
atcaattgcc aggccagtca gaacatttac agctacttat cctggtatca gcagaaacca   120

```
gggaaagttc ctaagcgcct gatctatctg gcatctactc tggcatctgg ggtcccatct    180
cggttcagtg gcagtggatc tgggacagat tacactctca ccatcagcag cctgcagcct    240
gaagatgttg caacttatta ctgtcaaagc aattataacg gtaattatgg tttcggcgga    300
gggaccaagg tggagatcaa a                                              321
```

```
<210> SEQ ID NO 119
<211> LENGTH: 214
<212> TYPE: PRT
<213> ORGANISM: Artificial Sequence
<220> FEATURE:
<223> OTHER INFORMATION: synthesized

<400> SEQUENCE: 119
```

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Asn Ile Tyr Ser Tyr
            20                  25                  30

Leu Ser Trp Tyr Gln Gln Lys Pro Gly Lys Val Pro Lys Arg Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Ser Asn Tyr Asn Gly Asn Tyr
                85                  90                  95

Gly Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 120
<211> LENGTH: 107
<212> TYPE: PRT
<213> ORGANISM: Artificial Sequence
<220> FEATURE:
<223> OTHER INFORMATION: synthesized

<400> SEQUENCE: 120
```

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Asn Ile Tyr Ser Tyr
            20                  25                  30

Leu Ser Trp Tyr Gln Gln Lys Pro Gly Lys Val Pro Lys Arg Leu Ile
        35                  40                  45
```

Tyr Leu Ala Ser Thr Leu Ala Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Val Ala Thr Tyr Tyr Cys Gln Ser Asn Tyr Asn Gly Asn Tyr
                 85                  90                  95

Gly Phe Gly Gly Gly Thr Lys Val Glu Ile Lys
                100                 105

<210> SEQ ID NO 121
<211> LENGTH: 1332
<212> TYPE: DNA
<213> ORGANISM: Artificial Sequence
<220> FEATURE:
<223> OTHER INFORMATION: synthesized

<400> SEQUENCE: 121
gaggtgcagc tggtggagtc tgggggaggc ttggtccagc ctgggggtc cctgagactc    60 tcctgtacag cctctggatt ctccctcagt agctatgcaa tgagctgggt ccgccaggct   120
ccagggaggg gctggagtg gatcggaatc atttatgcta gtggtagcac atactacgcg   180
agctcggcga aaggcagatt caccatctcc aaagacaata ccaagaacac ggtggatctt   240
caaatgaaca gcctgagagc cgaggacacg gctgtgtatt actgtgcgag aatttatgac   300
ggcatggacc tctggggcca gggaaccctg gtcaccgtct cgagcgctag caccaagggc   360
ccatcggtct tccccctggc accctcctcc aagagcacct ctggggcac agcggccctg   420 ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540 agcagcgtg tgaccgtgcc ctccagcagc ttgggcaccc agacctacat ctgcaacgtg   600
aatcacaagc ccagcaacac caaggtggac aagagagttg agcccaaatc ttgtgacaaa   660
actcacacat gcccaccgtg cccagcacct gaagccgcgg ggcaccgtc agtcttcctc   720 ttccccccaa aacccaagga caccctcatg atctcccgga cccctgaggt cacatgcgtg   780
gtggtggacg tgagccacga agaccctgag gtcaagttca actggtacgt ggacggcgtg   840
gaggtgcata atgccaagac aaagccgcgg gaggagcagt acaacagcac gtaccgtgtg   900
gtcagcgtcc tcaccgtcct gcaccaggac tggctgaatg caaggagta caagtgcgcg   960 gtctccaaca aagccctccc agccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                      1332

<210> SEQ ID NO 122
<211> LENGTH: 345
<212> TYPE: DNA
<213> ORGANISM: Artificial Sequence
<220> FEATURE:
<223> OTHER INFORMATION: synthesized

<400> SEQUENCE: 122
gaggtgcagc tggtggagtc tgggggaggc ttggtccagc ctgggggtc cctgagactc    60

```
tcctgtacag cctctggatt ctccctcagt agctatgcaa tgagctgggt ccgccaggct      120
ccagggaggg ggctggagtg gatcggaatc atttatgcta gtggtagcac atactacgcg      180
agctcggcga aaggcagatt caccatctcc aaagacaata ccaagaacac ggtggatctt      240
caaatgaaca gcctgagagc cgaggacacg gctgtgtatt actgtgcgag aatttatgac      300
ggcatggacc tctggggcca gggaaccctg gtcaccgtct cgagc                     345
```

<210> SEQ ID NO 123
<211> LENGTH: 444
<212> TYPE: PRT
<213> ORGANISM: Artificial Sequence
<220> FEATURE:
<223> OTHER INFORMATION: synthesized

<400> SEQUENCE: 123

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Ser Trp Val Arg Gln Ala Pro Gly Arg Gly Leu Glu Trp Ile
        35                  40                  45

Gly Ile Ile Tyr Ala Ser Gly Ser Thr Tyr Tyr Ala Ser Ser Ala Lys
    50                  55                  60

Gly Arg Phe Thr Ile Ser Lys Asp Asn Thr Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Ile Tyr Asp Gly Met Asp Leu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Ala
```

Val Ser Asn Lys Ala Leu Pro Ala Pro Ile Glu Lys Thr Ile Ser Lys
305                 310                 315                 320

Ala Lys Gly Gln Pro Arg Glu Pro Gln Val Tyr Thr Leu Pro Pro Ser
            325                 330                 335

Arg Asp Glu Leu Thr Lys Asn Gln Val Ser Leu Thr Cys Leu Val Lys
                340                 345                 350

Gly Phe Tyr Pro Ser Asp Ile Ala Val Glu Trp Glu Ser Asn Gly Gln
    355                 360                 365

Pro Glu Asn Asn Tyr Lys Thr Thr Pro Pro Val Leu Asp Ser Asp Gly
370                 375                 380

Ser Phe Phe Leu Tyr Ser Lys Leu Thr Val Asp Lys Ser Arg Trp Gln
385                 390                 395                 400

Gln Gly Asn Val Phe Ser Cys Ser Val Met His Glu Ala Leu His Asn
        405                 410                 415

His Tyr Thr Gln Lys Ser Leu Ser Leu Ser Pro Gly
            420                 425                 430

435                 440

<210> SEQ ID NO 124
<211> LENGTH: 115
<212> TYPE: PRT
<213> ORGANISM: Artificial Sequence
<220> FEATURE:
<223> OTHER INFORMATION: synthesized

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Ser Trp Val Arg Gln Ala Pro Gly Arg Gly Leu Glu Trp Ile
        35                  40                  45

Gly Ile Ile Tyr Ala Ser Gly Ser Thr Tyr Tyr Ala Ser Ser Ala Lys
    50                  55                  60

Gly Arg Phe Thr Ile Ser Lys Asp Asn Thr Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Ile Tyr Asp Gly Met Asp Leu Trp Gly Gln Gly Thr Leu Val Thr
            100                 105                 110

Val Ser Ser
        115

<210> SEQ ID NO 125
<211> LENGTH: 645
<212> TYPE: DNA
<213> ORGANISM: Artificial Sequence
<220> FEATURE:
<223> OTHER INFORMATION: synthesized

<400> SEQUENCE: 125
gacatccaga tgacccagtc tccttccacc ctgtctgcat ctgtaggaga cagagtcacc      60
atcacttgcc aggccagtca gagcattaat aactacttag cctggtatca gcagaaacca    120
gggaaagccc ctaagctcct gatctatagg gcatccactc tggaatctgg ggtcccatca    180
aggttcagcg gcagtggatc tgggacagaa ttcactctca ccatcagcag cctgcagcct    240
gatgattttg caacttatta ctgccaaagc tataatggtg ttggtaggac tgctttcggc    300

```
ggagggacca aggtggagat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacaca aaagtctacg cctgcgaagt cacccatcag    600
ggcctgagct cgcccgtcac aaagagcttc aacaggggag agtgt                    645
```

<210> SEQ ID NO 126
<211> LENGTH: 324
<212> TYPE: DNA
<213> ORGANISM: Artificial Sequence
<220> FEATURE:
<223> OTHER INFORMATION: synthesized

<400> SEQUENCE: 126

```
gacatccaga tgacccagtc tccttccacc ctgtctgcat ctgtaggaga cagagtcacc     60
atcacttgcc aggccagtca gagcattaat aactacttag cctggtatca gcagaaacca    120
gggaaagccc ctaagctcct gatctatagg gcatccactc tggaatctgg ggtcccatca    180
aggttcagcg gcagtggatc tgggacagaa ttcactctca ccatcagcag cctgcagcct    240
gatgattttg caacttatta ctgccaaagc tataatggtg ttggtaggac tgctttcggc    300
ggagggacca aggtggagat caaa                                           324
```

<210> SEQ ID NO 127
<211> LENGTH: 215
<212> TYPE: PRT
<213> ORGANISM: Artificial Sequence
<220> FEATURE:
<223> OTHER INFORMATION: synthesized

<400> SEQUENCE: 127

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asn Asn Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Tyr Asn Gly Val Gly Arg
                85                  90                  95

Thr Ala Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
```

```
               180                 185                 190
Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 128
<211> LENGTH: 108
<212> TYPE: PRT
<213> ORGANISM: Artificial Sequence
<220> FEATURE:
<223> OTHER INFORMATION: synthesized

<400> SEQUENCE: 128

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asn Asn Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Tyr Asn Gly Val Gly Arg
                85                  90                  95

Thr Ala Phe Gly Gly Gly Thr Lys Val Glu Ile Lys
            100                 105

<210> SEQ ID NO 129
<211> LENGTH: 1347
<212> TYPE: DNA
<213> ORGANISM: Artificial Sequence
<220> FEATURE:
<223> OTHER INFORMATION: synthesized

<400> SEQUENCE: 129
gaggtgcagc tggtggagtc tgggggaggc ttggtccagc ctggggggtc cctgagactc      60
tcctgtgcag cctctggatt ctccctcaat aactactgga tgagctgggt ccgccaggct     120
ccagggaagg ggctggagtg gatcggaacc attagtagtg gtgcgtatac atggttcgcc     180
acctgggcga caggcagatt caccatctcc agagacaatt ccaagaacac gctgtatctt     240
caaatgaaca gcctgagagc cgaggacacg gctgtgtatt actgtgcgag atattcttct     300
actactgatt ggacctactt taacatctgg ggccagggaa ccctggtcac cgtctcgagc     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaagc cgcggggggca     720 ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcggaggga gcagtacaac     900
```

```
agcacgtacc gtgtggtcag cgtcctcacc gtcctgcacc aggactggct gaatggcaag    960
gagtacaagt gcgcggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc tccgggt                                       1347
```

<210> SEQ ID NO 130
<211> LENGTH: 360
<212> TYPE: DNA
<213> ORGANISM: Artificial Sequence
<220> FEATURE:
<223> OTHER INFORMATION: synthesized

<400> SEQUENCE: 130

```
gaggtgcagc tggtggagtc tgggggaggc ttggtccagc ctgggggtc cctgagactc     60 tcctgtgcag cctctggatt ctccctcaat aactactgga tgagctgggt ccgccaggct   120
ccagggaagg ggctggagtg gatcggaacc attagtagtg gtgcgtatac atggttcgcc   180
acctgggcga caggcagatt caccatctcc agagacaatt ccaagaacac gctgtatctt   240
caaatgaaca gcctgagagc cgaggacacg gctgtgtatt actgtgcgag atattcttct   300
actactgatt ggacctactt taacatctgg ggccagggaa ccctggtcac cgtctcgagc   360
```

<210> SEQ ID NO 131
<211> LENGTH: 449
<212> TYPE: PRT
<213> ORGANISM: Artificial Sequence
<220> FEATURE:
<223> OTHER INFORMATION: synthesized

<400> SEQUENCE: 131

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Asn Tyr
            20                  25                  30

Trp Met Ser Trp Val Arg Gln Ala Pro Gly Lys Gly Leu Glu Trp Ile
        35                  40                  45

Gly Thr Ile Ser Ser Gly Ala Tyr Thr Trp Phe Ala Thr Trp Ala Thr
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Ser Ser Thr Thr Asp Trp Thr Tyr Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                165                 170                 175
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 132
<211> LENGTH: 120
<212> TYPE: PRT
<213> ORGANISM: Artificial Sequence
<220> FEATURE:
<223> OTHER INFORMATION: synthesized

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Asn Tyr
            20                  25                  30

Trp Met Ser Trp Val Arg Gln Ala Pro Gly Lys Gly Leu Glu Trp Ile
        35                  40                  45

Gly Thr Ile Ser Ser Gly Ala Tyr Thr Trp Phe Ala Thr Trp Ala Thr
    50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Ala
            85                  90                  95

Arg Tyr Ser Ser Thr Thr Asp Trp Thr Tyr Phe Asn Ile Trp Gly Gln
                100             105                 110

Gly Thr Leu Val Thr Val Ser Ser
        115             120
```

ANTI-ROR1 ANTIBODIES AND METHODS OF MAKING AND USING THEREOF

CROSS REFERENCE TO RELATED APPLICATIONS

This application claims the benefit of filing dates of U.S. Provisional Patent Application No. 62/551,035, filed Aug. 28, 2017, U.S. Provisional Patent Application No. 62/551,032 filed Aug. 28, 2017, U.S. Provisional Patent Application No. 62/524,554 filed Jun. 25, 2017, U.S. Provisional Patent Application No. 62/524,557 filed Jun. 25, 2017, U.S. Provisional Patent Application No. 62/524,558 filed Jun. 25, 2017, U.S. Provisional Patent Application No. 62/545,603 filed Aug. 15, 2017, U.S. Provisional Patent Application No. 62/551,032 filed Aug. 28, 2017, and U.S. Provisional Patent Application No. 62/551,065 filed Aug. 28, 2017, the entire disclosures of which are expressly incorporated by reference herein.

TECHNICAL FIELD

The present disclosure generally relates to the technical field of antibodies, and more particularly relates to making and using anti-ROR1 antibodies.

BACKGROUND

Cancer is a major health problem across the world. In the United States alone it is estimated that in 2016 there were 1,685,210 new cases of cancer diagnosed and 595,690 deaths from the disease (http://www.cancer.gov). As such, any pharmaceutical agent that can reduce the severity or mortality rate from cancer is desirable.

In the immune system, resting T-cells can be activated to respond to antigen through a primary signal delivered through the T-cell receptor (TCR) by foreign antigen peptides presented by antigen-presenting cells (APCs). In addition to this primary signal, there are secondary positive and negative co-stimulatory signals that further influence the response of the T-cells. A secondary positive signal is required for full T-cell activation (see, Lafferty et al., Ausl. J. Exp. Biol. Med. Sci. 53: 27-42, 1975). Negative secondary signals can result in T-cell suppression and tolerance.

Tyrosine-protein kinase transmembrane receptor ROR1, also known as neurotrophic tyrosine kinase, receptor-related 1 (NTRKR1), is an enzyme that in humans is encoded by the ROR1 gene. (see, Masiakowski P and Carroll R D, J. Bio. Chem. 267 (36): 26181-90. 1992; Reddy U R, et al, Oncogene. 13 (7): 1555-9, 1996). ROR1 is a member of the receptor tyrosine kinase-like orphan receptor (ROR) family. ROR1 has recently been shown to be expressed on ovarian cancer stem cell, on which it seems to play a functional role in promoting migration/invasion or spheroid formation in vitro and tumour engraftment in immune-deficient mice. Treatment with a humanized mAb specific for ROR1 (UC-961) could inhibit the capacity of ovarian cancer cells to migrate, form spheroids, or engraft immune-deficient mice. Moreover, such treatment inhibited the growth of tumour xenografts, which in turn had a reduced capacity to engraft immune-deficient mice and were relatively depleted of cells with features of CSC, suggesting that treatment with UC-961 could impair CSC renewal. Collectively, these studies indicate that ovarian CSCs express ROR1, which may be targeted for anti-CSC therapy. (see, Zhang S, et al, PNAS. 111 (48): 17266-71, 2014).

ROR1 is expressed in a number of malignancies with low levels of expression in normal adult tissue. Much like the physiological functions of ROR1, ROR1 in cancer can have kinase activity-dependent or -independent function, which could be a result of tissue specific expression of co-receptor or effector proteins. The induction of apoptosis with ROR1 knockdown, EGFR signalling potentiation and ROR1-mediated upregulation of EMT genes support the notion that ROR1 plays an important role in cancer progression. Further research is required to elucidate the tumour-specific mechanisms of ROR1 overexpression and the contribution of ROR1 to initiation and progression of cancer.

SUMMARY

In one aspect, the present disclosure provides, among others, anti-ROR1 monoclonal antibodies, antigen binding portions thereof, therapeutic compositions thereof and/or nucleic acid encoding the same.

In one embodiment, the disclosure provides one or more isolated monoclonal antibodies (mAb) or antigen-binding fragment thereof that binds specifically to human ROR1. In one embodiment, the isolated one or more mAb or antigen-binding fragment includes an antigenic peptide sequence having a sequence as disclosed herein. In one embodiment, the isolated mAb or antigen-binding fragment is selected from the sequences as disclosed herein.

In one embodiment, an isolated monoclonal antibody (mAb) or antigen-binding fragment have an amino acid sequence having a percentage homology with SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, or SEQ ID NO:132. In one embodiment, the percentage homology is not less than 70%, 80%, 90%, 95%, 98%, or 99%

In one embodiment, the isolated one or more mAb or antigen-binding fragment has a binding affinity to ROR1 with a Kd not greater than 30 nM, 40 nM, 50 nM, 60 nM, 70 nM, 80 nM, 90 nM or 100 nM. In one embodiment, the ROR1 is a human ROR1.

In one embodiment, the isolated mAb or antigen-binding fragment exhibits one or more functional properties. Example functional properties include without limitation high affinity binding to ROR1, enhancing T cell activation, the ability to stimulate antibody responses and/or the ability to reverse the suppressive function of immunosuppressive cells, such as T regulatory cells. In one embodiment, the enhancing T-cell activation comprises T-cell proliferation, IFN-γ and/or IL-2 secretion, or a combination thereof. In one embodiment, the immunosuppressive cell comprises a regulatory cell.

In one embodiment, the isolated mAb or antigen-binding fragment comprises a human framework region. In one embodiment, the isolated mAb or antigen-binding fragment is a humanized antibody, a chimeric antibody, or a recombinant antibody.

In one embodiment, the isolated mAb or antigen-binding fragment is an IgG. In one embodiment, the antigen-binding fragment is a Fv, a Fab, a F(ab')2, a scFV or a scFV2 fragment. In one embodiment, the isolated mAb is a bispecific antibody, tri-specific antibody, or multi-specific antibody.

In one embodiment, the application provides an isolated mAb or antigen-binding fragment having a binding specificity to ROR1 and an IgG1 heavy chain. The IgG heavy chain comprises an amino acid sequence having a percentage homology with SEQ ID NO:7, SEQ ID NO:15, SEQ ID NO:23, SEQ ID NO:31, SEQ ID NO:39, SEQ ID NO:47, SEQ ID NO:55, SEQ ID NO:63, SEQ ID NO:71, SEQ ID NO:79, SEQ ID NO:87, SEQ ID NO:91, SEQ ID NO:99, SEQ ID NO:107, SEQ ID NO:115, SEQ ID NO:123, or SEQ ID NO:131. The percentage homology is not less than 70%, 80%, 90%, 95%, 98%, or 99%.

In one embodiment, the application provides an isolated mAb or antigen-binding fragment having a binding specificity to ROR1 and a kappa light chain. The kappa light chain comprises an amino acid sequence having a percentage homology with SEQ ID NO:3, SEQ ID NO:11, SEQ ID NO:19, SEQ ID NO:27, SEQ ID NO:35, SEQ ID NO:43, SEQ ID NO:51, SEQ ID NO:59, SEQ ID NO:67, SEQ ID NO:75, SEQ ID NO:83, SEQ ID NO:95, SEQ ID NO:103, SEQ ID NO:111, SEQ ID NO:119, or SEQ ID NO:127. The percentage homology is not less than 70%, 80%, 90%, 95%, 98%, or 99%.

In one embodiment, the application provides an isolated mAb or antigen-binding fragment having a binding specificity to ROR1 and a variable light chain. The variable chain comprises an amino acid sequence having a percentage homology with SEQ ID NO:4, SEQ ID NO:12, SEQ ID NO:20, SEQ ID NO:28, SEQ ID NO:36, SEQ ID NO:44, SEQ ID NO:52, SEQ ID NO:60, SEQ ID NO: 68, SEQ ID NO:76, SEQ ID NO:84, SEQ ID NO:96, SEQ ID NO:104, SEQ ID NO:112, SEQ ID NO:120, or SEQ ID NO:128. The percentage homology is not less than 70%, 80%, 90%, 95%, 98%, or 99%.

In one embodiment, the application provides an isolated mAb or antigen-binding fragment having a binding specificity to ROR1 and a variable heavy chain. The variable heavy chain comprises an amino acid sequence having at least 90% identity with SEQ ID NO:8, SEQ ID NO:16, SEQ ID NO:24, SEQ ID NO:32, SEQ ID NO:40, SEQ ID NO:48, SEQ ID NO:56, SEQ ID NO:64, SEQ ID NO:72, SEQ ID NO:80, SEQ ID NO:88, SEQ ID NO:92, SEQ ID NO:100, SEQ ID NO:108, SEQ ID NO:116, SEQ ID NO:124, or SEQ ID NO:132. The percentage homology is not less than 70%, 80%, 90%, 95%, 98%, or 99%.

The application further provides isolated nucleic acids encode at least a portion of the isolated mAb or antigen-binding fragment disclosed herein. In one embodiment, the isolated mAb or antigen-binding fragment has a percentage homology with the IgG1 heavy chain SEQ ID NO:7, SEQ ID NO:15, SEQ ID NO:23, SEQ ID NO:31, SEQ ID NO:39, SEQ ID NO:47, SEQ ID NO:55, SEQ ID NO:63, SEQ ID NO:71, SEQ ID NO:79, SEQ ID NO:87, SEQ ID NO:91, SEQ ID NO:99, SEQ ID NO:107, SEQ ID NO:115, SEQ ID NO:123, or SEQ ID NO:131. In one embodiment, the isolated mAb or antigen-binding fragment has a percentage homology with the kappa light: SEQ ID NO:3, SEQ ID NO:11, SEQ ID NO:19, SEQ ID NO:27, SEQ ID NO:35, SEQ ID NO:43, SEQ ID NO:51, SEQ ID NO:59, SEQ ID NO:67, SEQ ID NO:75, SEQ ID NO:83, SEQ ID NO:95, SEQ ID NO:103, SEQ ID NO:111, SEQ ID NO:119, or SEQ ID NO:127. In one embodiment, the isolated mAb or antigen-binding fragment has a percentage homology with the the variable light chain: SEQ ID NO:4, SEQ ID NO:12, SEQ ID NO:20, SEQ ID NO:28, SEQ ID NO:36, SEQ ID NO:44, SEQ ID NO:52, SEQ ID NO:60, SEQ ID NO: 68, SEQ ID NO:76, SEQ ID NO:84, SEQ ID NO:96, SEQ ID NO:104, SEQ ID NO:112, SEQ ID NO:120, or SEQ ID NO:128. In one embodiment, the isolated mAb or antigen-binding fragment has a percentage homology with the variable heavy: SEQ ID NO:8, SEQ ID NO:16, SEQ ID NO:24, SEQ ID NO:32, SEQ ID NO:40, SEQ ID NO:48, SEQ ID NO:56, SEQ ID NO:64, SEQ ID NO:72, SEQ ID NO:80, SEQ ID NO:88, SEQ ID NO:92, SEQ ID NO:100, SEQ ID NO:108, SEQ ID NO:116, SEQ ID NO:124, or SEQ ID NO:132. The percentage homology is not less than 70%, 80%, 90%, 95%, 98%, or 99%.

The application further provides expression vectors containing the isolated nucleic acid encoding an amino acid sequence having a percentage homology with the amino acid sequences disclosed herein. The percentage homology is not less than 70%, 80%, 90%, 95%, 98%, or 99%. In one embodiment, the expression vector is expressible in a cell.

The application further provides host cells comprising nucleic acids that encode an amino acid sequence having a percentage homology with the amino acid sequences disclosed herein. The percentage homology is not less than 70%, 80%, 90%, 95%, 98%, or 99%. In one embodiment, the host cell can be a prokaryotic cell or a eukaryotic cell.

In another aspect, the application provides methods for producing an antibody or its antigen-binding fragment thereof having a binding specificity to human ROR1. In one embodiment, the method includes the steps of providing a host cell that contains an expression vector expressible in the host cell, the expression vector comprises nucleic acids encoding at least at portion of the isolated mAb or antigen-binding fragment, or peptides with at least 70%, 80%, 90%, 95%, 98%, or 99% identity, to produce an antibody by the expression of the nucleic acids.

The application further provides immuno-conjugates. In one embodiment, the immuno-conjugates include a drug unit or an imaging agent linked to an isolated mAb or antigen-binding fragment disclosed herein through a linker.

The linker may be cleavable or non-cleavable. In one embodiment, the linker is a chemical linker. In one embodiment, the linker comprises a covalent bond such as an ester bond, an ether bond, an amine bond, an amide bond, a disulphide bond, an imide bond, a sulfone bond, a phosphate bond, a phosphorus ester bond, a peptide bond, a hydrazone bond or a combination thereof. In one embodiment, the linker comprises a hydrophobic poly(ethylene glycol) linker. In one embodiment, the linker comprises a peptide bond.

In one embodiment, the drug unit in the immuno-conjugate comprises a chemotherapeutic agent, a growth inhibitory agent, a cytotoxic agent from class of calicheamicin, an antimitotic agent, a toxin, a radioactive isotope, or a combination thereof. In one embodiment, the drug unit comprises a calicheamicin, ozogamicin, monomethyl auristatin E, emtansine, a derivative or a combination thereof. In one embodiment, the drug unit comprises a calicheamicin, ozogamicin, monomethyl auristatin E, emtansine, a derivative or a combination thereof.

In one embodiment, the drug unit is selected from a cytotoxic agent, an immune regulatory reagent, an imaging agent or a combination thereof. In one embodiment, the cytotoxic agent is selected from a growth inhibitory agent or a chemotherapeutic agent from a class of tubulin binders, DNA intercalators, DNA alkylators, enzyme inhibitors, immune modulators, antimetabolite agents, radioactive isotopes, or a combination thereof. In one embodiment, the cytotoxic agent is selected from a calicheamicin, ozogamicin, monomethyl auristatin E, emtansine, a derivative or a combination thereof. In one embodiment, the immune regulatory reagents activate or suppress immune cells, T cell, NK cell, B cell, macrophage, or dendritic cell.

In one embodiment, the imaging agent may be radionuclide, a florescent agent, a quantum dots, or a combination thereof.

The application further provides a pharmaceutical composition. In one embodiment, the pharmaceutical composition comprises the isolated mAb or antigen-binding fragment disclosed herein and a pharmaceutically acceptable carrier. In one embodiment, the pharmaceutical composition comprises an immuno-conjugate disclosed herein and pharmaceutically acceptable carrier. In one embodiment, the pharmaceutical composition further a chemotherapeutic agent, a growth inhibitory agent, a drug unit from class of calicheamicin, an antimitotic agent, a toxin, a radioactive isotope, a toxin, a therapeutic agent, or a combination thereof.

In a further aspect, the application provides a method of treating a subject with a cancer using the isolated mAb or antigen-binding fragment thereof as disclosed herein. In one embodiment, the method comprises the step of administering to the subject an effective amount of the isolated mAb or antigen-binding fragment as disclosed herein.

In one embodiment, the method includes directly injecting into the tumour site an effective amount of the monoclonal antibodies, the antigen-binding fragment thereof, and the immuno-conjugates and disclosed herein.

Varieties of cancer may be treated using the disclosed mAB, antigen-binding fragment thereof, or compositions. In one embodiment, the cancer has cells that express ROR-1. Example cancers include without limitation breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer.

In one embodiment, the method further includes co-administering an effective amount of a therapeutic agent. Example therapeutic a chemotherapeutic agent, a growth inhibitory agent, a drug unit from class of calicheamicin, an antimitotic agent, a toxin, a radioactive isotope, an antibody, an enzyme, or a combination thereof. In one embodiment, the therapeutic agent can be capecitabine, cisplatin, Cyclophosphamide, methotrexate, 5-fluorouracil, Doxorubicin, cyclophosphamide, Mustine, vincristine, procarbazine, prednisolone, bleomycin, vinblastine, dacarbazine, etoposide, Epirubicin, pemetrexed, folinic acid, gemicitabine, oxaliplatin, irinotecan, topotecan, camptothecin, docetaxel, paclitaxel, fulvestrant, tamoxifen, letrozole, exemestane, anastrozole, aminoglutethimide, testolactone, vorozole, formestane, fadrozole, letrozole, erlotinib, lafatinib, dasatinib, gefitinib, osimertinib, vandertanib, afatinib, imatinib, pazopinib, lapatinib, sunitinib, nilotinib, sorafenib, nab-palitaxel, Everolimus, temsirolimus, Dabrafenib, vemurafenib, trametinib, vintafolide, apatinib, crizotinib, periforsine, olaparib, Bortezomib, tofacitinib, or a derivative or a combination thereof.

The subject receiving treatment may be a human. In one embodiment, the application provides a solution comprising an effective concentration of the isolated mAb or an antigen-binding fragment disclosed herein, wherein the solution is blood plasma in a subject.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

FIG. 1 provides immunization strategy of NZW rabbits with human or mouse ROR1;

FIG. 2 provides immunization timeline;

FIG. 3 shows the harvest of spleen and lymph tissue from ROR1-immunized rabbits;

FIG. 4 shows the summary of B cell culture screening for ROR1-specific IgG and screening of chimeric rabbit/human IgG;

FIG. 5 shows the binding and off-rate analysis of different ROR1-specific humanized rabbit antibodies; and FIG. 6 is a graph showing analytic results of rabbit serum for human and mouse ROR1-specific IgG before and after immunization, according to one embodiment.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The disclosure provides, among others, isolated antibodies having specificity against ROR1, antigen binding fragment thereof, methods of making such antibodies, bispecific or multi-specific molecules, antibody-drug conjugates and/or immuno-conjugates composed from such antibodies or antigen binding fragment, pharmaceutical compositions containing the antibodies or antigen binding fragment, bispecific or multi-specific molecules, antibody-drug conjugates and/or immuno-conjugates, and methods for using the disclosed antibodies, antigen binding fragments and compositions for treating cancer.

In one aspect, the application provides monoclonal antibodies that bind specifically to human or mouse ROR1. In one embodiment, antibodies exhibit one or more desirable functional properties, such as high affinity binding to ROR1. In one embodiment, the antibodies are derived from specific heavy and light chain amino acid sequences and/or structural features such as rabbit/human chimeric antibodies composed of specific amino acid sequences.

Monoclonal antibodies can be produced using various methods including mouse hybridoma or phage display (see Siegel. Transfus. Clin. Biol. 9:15-22 (2002) for a review) or from molecular cloning of antibodies directly from primary B cells (see Tiller. New Biotechnol. 28:453-7 (2011)). In one embodiment, antibodies were created by the immunization of rabbits with either human or mouse ROR1 extracellular domain (ECD) or HEK 293 cells transiently transfected with mouse or human ROR1. Rabbits are known to create antibodies of high affinity, diversity and specificity (Weber et al. Exp. Mol. Med. 49:e305). B cells from immunized animals were cultured in vitro and screened for the production of anti-ROR1 antibodies. The antibody variable genes were isolated using recombinant DNA techniques and the resulting antibodies were expressed recombinantly. This general method of antibody discovery is similar to that described in Seeber et al. PLOS One. 9:e86184 (2014).

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, and Fv), so long as they exhibit the desired biological activity. In some embodiments, the antibody may be monoclonal, polyclonal, chimeric, single chain, bispecific or bi-effective, simianized, human and humanized antibodies as well as active fragments thereof. Examples of active fragments of molecules that bind to known antigens include Fab, F(ab')$_2$, scFv and Fv fragments, including the products of an Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site that immunospecifically bind an antigen. The immunoglobulin can be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be whole antibodies and any antigen-binding fragment derived from the whole antibodies. A typical antibody refers to heterotetrameric protein comprising typically of two heavy (H) chains and two light (L) chains. Each heavy chain is comprised of a heavy chain variable domain (abbreviated as VH) and a heavy chain constant domain. Each light chain is comprised of a light chain variable domain (abbreviated as VL) and a light chain constant domain. The VH and VL regions can be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the light and heavy chains there are binding regions that interacts with the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler & Milstein, *Nature,* 256:495 (1975), or may be made by recombinant DNA methods (see, e.g., U.S. Pat. No. 4,816,567).

The monoclonal antibodies may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA,* 81:6851-6855 [1984]).

Monoclonal antibodies can be produced using various methods including mouse hybridoma or phage display (see Siegel. Transfus. Clin. Biol. 9:15-22 (2002) for a review) or from molecular cloning of antibodies directly from primary B cells (see Tiller. New Biotechnol. 28:453-7 (2011)). In the present disclosure antibodies were created by the immunization of rabbits with both human PD-L1 protein and cells transiently expressing human PD-L1 on the cell surface. Rabbits are known to create antibodies of high affinity, diversity and specificity (Weber et al. Exp. Mol. Med. 49:e305). B cells from immunized animals were cultured in vitro and screened for the production of anti-PD-L1 antibodies. The antibody variable genes were isolated using recombinant DNA techniques and the resulting antibodies were expressed recombinantly and further screened for desired features such as ability to inhibit the binding of PD-L1 to PD-1, the ability to bind to non-human primate PD-L1 and the ability to enhance human T-cell activation. This general method of antibody discovery is similar to that described in Seeber et al. PLOS One. 9:e86184 (2014).

The term "antigen- or epitope-binding portion or fragment" refers to fragments of an antibody that are capable of binding to an antigen (ROR1 in this case). These fragments may be capable of the antigen-binding function and additional functions of the intact antibody. Examples of binding fragments include, but are not limited to a single-chain Fv fragment (scFv) consisting of the VL and VH domains of a single arm of an antibody connected in a single polypeptide chain by a synthetic linker or a Fab fragment which is a monovalent fragment consisting of the VL, constant light (CL), VH and constant heavy 1 (CH1) domains. Antibody fragments can be even smaller subfragments and can consist of domains as small as a single CDR domain, in particular the CDR3 regions from either the VL and/or VH domains (for example see Beiboer et al., J. Mol. Biol. 296:833-49 (2000)). Antibody fragments are produced using conventional methods known to those skilled in the art. The antibody fragments are can be screened for utility using the same techniques employed with intact antibodies.

The "antigen-or epitope-binding fragments" can be derived from an antibody of the present disclosure by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

The Fab fragment may contain the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other, chemical couplings of antibody fragments are also known.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The "light chains" of antibodies (immunoglobulins) from any vertebrate species can be assigned to one of two clearly distinct types, called kappa and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)).

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

By "isolated" is meant a biological molecule free from at least some of the components with which it naturally occurs. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities.

"Recombinant" means the antibodies are generated using recombinant nucleic acid techniques in exogeneous host cells.

The term "antigen" refers to an entity or fragment thereof which can induce an immune response in an organism, particularly an animal, more particularly a mammal including a human. The term includes immunogens and regions thereof responsible for antigenicity or antigenic determinants.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs. The deviations appearing in the comparison between a given sequence and the above-described sequences of the disclosure may be caused for instance by addition, deletion, substitution, insertion or recombination.

The application further provides immuno-conjugates including a drug unit linked to the antibodies and antigen-binding fragments disclosed herein through a linker. The linker may be cleavable or noncleavable. In one embodiment, the linker is a chemical linker. In one embodiment, the linker comprises a covalent bond such as an ester bond, an ether bond, an amid bond, a disulphide bond, an imide bond, a sulfone bond, a phosphate bond, a phosphorus ester bond, a peptide bond, or a combination thereof. In one embodiment, the linker comprises a hydrophobic poly(ethylene glycol) linker. In one embodiment, the linker comprises a peptide bond.

In one embodiment, the drug unit may be a chemotherapeutic agent, a growth inhibitory agent, a drug unit from class of calicheamicin, an antimitotic agent, a toxin, a radioactive isotope, a toxin, a therapeutic agent, or a combination thereof. In one embodiment, the therapeutic agent comprises an antibody, a chemotherapy agent, an enzyme, or a combination thereof.

In another aspect, the application provides pharmaceutical compositions. In one embodiment, the pharmaceutical composition includes the antibodies or antigen-binding fragments thereof and a pharmaceutically acceptable carrier. In one embodiment, the pharmaceutical composition includes the immuno-conjugate disclosed herein and a pharmaceutically acceptable carrier.

The antibodies and antigen-binding fragments or immuno-conjugates can be prepared in a physiologically acceptable formulation and may comprise a pharmaceutically acceptable carrier, diluent and/or excipient using known techniques. For example, the antibody disclosed herein may include any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions.

The pharmaceutical composition may further comprise proteinaceous carriers such as, for example, serum albumin or immunoglobulin, particularly of human origin. In one embodiment, the proteinaceous pharmaceutically active matter may be present in amounts between 1 ng and 10 mg per dose. Generally, the regime of administration should be in the range of between 0.1 µg and 10 mg of the antibody according to the disclosure, particularly in a range 1.0 µg to 1.0 mg, and more particularly in a range of between 1.0 µg and 100 µg, with all individual numbers falling within these ranges also being part of the disclosure. If the administration occurs through continuous infusion a more proper dosage may be in the range of between 0.01 µg and 10 mg units per kilogram of body weight per hour with all individual numbers falling within these ranges also being part of the disclosure.

"Pharmaceutically acceptable" refers to those compounds, materials, compositions, and dosage forms which are, within the scope of sound medical judgment, suitable for use contact with the tissues of human beings or animals without excessive toxicity, irritation, or other problem or complication, commensurate with a reasonable benefit/risk ratio. Formulation of the pharmaceutical composition according to the disclosure can be accomplished according to standard methodology know to those of ordinary skill in the art.

Further biologically active agents may be present in the pharmaceutical composition of the disclosure dependent on the intended use. In one embodiment, the composition disclosed herein may be administered in combination with other compositions comprising a biologically active/therapeutical substance or compound, particularly at least one compound selected from the group consisting of the therapeutic agent comprises capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, calicheamicin, antimitotic agent, monomethyl auristatin E, emtansine, ozogamicin, a derivative or a combination thereof.

In another aspect, the application provides methods for treating a subject using anti-ROR1 antibodies or other molecules containing the antigen-binding portion of an anti-ROR1 antibody. In one embodiment, the method inhibits growth of tumour cells. In some embodiments, the method uses the disclosed antibodies or compositions to stimulate a protective autoimmune response, to modify an immune response or to stimulate antigen-specific immune responses.

In one embodiment, the method include the step of administering to a subject in need of such treatment an effective amount of the anti-ROR1 antibodies or other molecules or composition disclosed herein.

The compositions may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumour site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumour. The method includes administration of a single dose, administration of repeated doses at predetermined time intervals, and sustained administration for a predetermined period of time.

In one embodiment, administration may be parenterally, e.g. intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

It is well known to those of ordinary skill in the art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The term "therapeutically effective amount" refers to the amount of antibody which, when administered to a human or animal, elicits a response which is sufficient to result in a therapeutic effect in said human or animal. The effective amount is readily determined by one of ordinary skill in the art following routine procedures.

Varieties of cancer may be treated using the disclosed mAb, antigen-binding fragments, or compositions. Cancers, including breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer, may express ROR1 genes. In one embodiment, administering a therapeutically effective amount of composition comprising anti-ROR1 monoclonal antibodies or antigen-binding fragment or its immuno-conjugates thereof is used to cure, prevent, ameliorate, and delay the development or metastasis of cancers.

The present disclosure may be understood more readily by reference to the following detailed description of specific embodiments included herein. Although the present disclosure has been described with reference to specific details of certain embodiments thereof, it is not intended that such details should be regarded as limitations upon the scope of the disclosure.

EXAMPLES

Example 1: Generation of Anti-ROR1 Antibodies

Monoclonal antibodies against human ROR1 were developed by immunizing New Zealand white rabbits. As shown in FIG. 1, animals were immunized with recombinant human or mouse ROR1 extracellular domain (ECD) or HEK 293 cells transiently transfected with mouse or human ROR1 mixed 1:1 v/v with Complete or incomplete Freund's adjuvant (Cohort 1) or Titermax Gold (Cohort 2) alternating with Alhydrogel 2% (Alum) plus CpG 2007 and were performed by subcutaneous injection. Subsequent boosts were performed at days 7, 14, 21, 28 and 37 as shown in FIG. 2.

On week 5 the serum from the animals was tested for ROR1 titer by ELISA. Serum from each rabbit is obtained before immunization as a negative control. After immunization serum is again collected from each animal and compared to the pre-immunization serum from the same animal for the presence of ROR1-specific IgG antibodies. As shown in FIG. 6 all animals immunized with human and mouse ROR1 developed detectable titres of human or mouse ROR1-specific IgG antibodies.

As shown in FIG. 3, spleen and lymph nodes were harvest from 2 animals each on days 4, 13, and 21 following a final immunization. ROR1-specific IgG+B cells were sorted at 1 per well into multiple 96 well tissue culture plates and cultured for 9 days to allow their differentiation into plasma cells and for secretion of antibodies. The supernatants from these plasma cell cultures were screened by ELISA and flow cytometry for the presence of ROR1-specific antibodies in a series of binding assays as listed below:

Human ROR1 directly coated on the plate—detection of ROR1-specific IgG ELISA

Mouse ROR1 directly coated on the plate—detection of ROR1-specific IgG ELISA

Human ROR2 directly coated on the plate—detection of ROR1-specific IgG ELISA

Biotinylated human ROR1 added to an avidin coated plate—detection of ROR1-specific IgG ELISA Biotinylated human ROR1 "Kringle domain" added to an avidin coated plate—detection of ROR1-Kringle-specific IgG ELISA Biotinylated human ROR1 "Frizzled-Kringle domain" added to an avidin coated plate—detection of ROR1-Frizzled-Kringle-specific IgG ELISA Biotinylated human ROR1 "Ig-Frizzled domain" added to an avidin coated plate—detection of ROR1-Ig-Frizzled-specific IgG ELISA Human ROR1 "Frizzled-Kringle domain" directly coated on the plate—detection of ROR1-Frizzled-Kringle-specific IgG ELISA Human ROR1 "Ig-Frizzled domain" directly coated on the plate—detection of ROR1-Ig-Frizzled-specific IgG ELISA Human ROR1-CHO cells—detection of ROR1-specific IgG by FACS On day 9 of B cell culture the supernatants were separated from the B cells and stored in a separate plate for later analysis. RNA later tissue storage reagent was added to each well in the B cell culture plate to preserve the RNA in the B cells for RT-PCR amplification of antibody variable regions.

B cell culture wells identified through ELISA and FACS screening as having the desired antibodies we advanced to molecular "rescue" of the antibody variable regions. The light and heavy chain variable sequences were amplified by multiplex RT-PCR using degenerate primers designed to anneal to leader sequences and the constant regions of rabbit IgG and rabbit kappa sequences. Secondary PCR was performed separately for the light and heavy chains using nested primers containing restriction sites. Amplicons from the variable heavy chain PCR were cloned into an expression vector containing human IgG1. Light chain amplicons were cloned into an expression vector containing human IgK. Resulting clones were sequenced and analyzed.

The heavy and light chain expression plasmids generated from each well were transiently co-transfected to produce rabbit/human chimeric antibodies. Recombinant antibody supernatants were confirmed to contain anti-ROR1 antibodies using bio-layer interferometry analysis on a ForteBio Octet Red 96 instrument. Anti-human Fc biosensors (Pall ForteBio) were used to capture antibodies in the supernatants. Association to ROR1 was observed by real-time interferometry by placing the biosensors in wells containing recombinant human ROR1 extracellular domain protein. Dissociation was measured after transfer of the biosensors into wells containing 10× kinetics buffer (Pall ForteBio). The software provided by the manufacturer was used to analyze the interferometry data.

A summary of the primary BCC screening data and the corresponding screening data for 27 recombinant chimeric rabbit/human IgG antibodies is shown in Tables 4a and 4b.

The heavy and light chain variable regions for 8 of 27 chimeric rabbit/human IgG antibodies listed in FIG. 4 were humanized. Humanized variants for 8 of 27 antibodies showed similar binding kinetics to human ROR1 by octet analysis which is summarized in FIG. 5.

While the disclosure has been particularly shown and described as referenced to the embodiments thereof, those skilled in the art will understand that the foregoing and other changes in form and detail may be made therein without departing from the spirit and scope. All references cited or referred to in this disclosure are hereby incorporated by reference in their entireties.

SEQUENCE LISTING
ANTI-ROR1 ANTIBODY SEQUENCES
226E12 CHIMERIC LIGHT CHAIN FULL-LENGTH NUCLEOTIDE SEQUENCE
SEQ ID NO: 1
GCCTATGATATGACCCAGACTCCATCCTCCGTGTCTGCAGCTGTGGGAGGCACAGTCACCATCAAGTGCCAGGCC

AGTCAGAGAATTTACAGCTACTTAGCCTGGTATCAGCAGAAACCAGGGCAGCCTCCCAAGCTCCTGATCTACAGG

GCATCCACTCTGGCATCTGGGGTCCCATCGCGGTTCAAAGGCAGTGGATCTGGGACAGAGTACACTCTCACCATC

AGCGACCTGGAGTGTGCCGATGCTGCCACTTACTACTGTCAACAGGGTGCTAGTATGGTTGATGTTGAGAATATG

TTCGGCGGAGGGACCGAGGTGGTGGTCAAACGTACGGTGGCTGCACCATCTGTCTTCATCTTCCCGCCATCTGAT

GAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCACC

TACAGCCTCAGCAGCACCCTGACGCTGAGCAAAGCAGACTACGAGAAACACAAAGTCTACGCCTGCGAAGTCACC

CATCAGGGCCTGAGCTCGCCCGTCACAAAGAGCTTCAACAGGGGAGAGTGT

226E12 CHIMERIC LIGHT CHAIN VARIABLE LIGHT CHAIN NUCLEOTIDE
SEQUENCE
SEQ ID NO: 2
GCCTATGATATGACCCAGACTCCATCCTCCGTGTCTGCAGCTGTGGGAGGCACAGTCACCATCAAGTGCCAGGCC

AGTCAGAGAATTTACAGCTACTTAGCCTGGTATCAGCAGAAACCAGGGCAGCCTCCCAAGCTCCTGATCTACAGG

GCATCCACTCTGGCATCTGGGGTCCCATCGCGGTTCAAAGGCAGTGGATCTGGGACAGAGTACACTCTCACCATC

AGCGACCTGGAGTGTGCCGATGCTGCCACTTACTACTGTCAACAGGGTGCTAGTATGGTTGATGTTGAGAATATG

TTCGGCGGAGGGACCGAGGTGGTGGTCAAA

226E12 CHIMERIC LIGHT CHAIN FULL-LENGTH AMINO ACID SEQUENCE.
HUMAN KAPPA CONSTANT DOMAIN IS UNDERLINED
SEQ ID NO: 3
AYDMTQTPSSVSAAVGGTVTIKCQASQRIYSYLAWYQQKPGQPPKLLIYRASTLASGVPSRFKGSGSGTEYTLTI

SDLECADAATYYCQQGASMVDVENMFGGGTEVVVK<u>RTVAAPSVFIFPPSDEQLKSGTASVVCLLNNFYPREAKVQ</u>

<u>WKVDNALQSGNSQESVTEQDSKDSTYSLSSTLTLSKADYEKHKVYACEVTHQGLSSPVTKSFNRGEC</u>

226E12 CHIMERIC LIGHT CHAIN VARIABLE LIGHT CHAIN AMINO ACID
SEQUENCE. COMPIMENTARITY DETERMINING REGIONS ARE UNDERLINED
SEQ ID NO: 4
AYDMTQTPSSVSAAVGGTVTIKC<u>QASQRIYSYLA</u>WYQQKPGQPPKLLIY<u>RASTLAS</u>GVPSRFKGSGSGTEYTLTI

SDLECADAATYY<u>CQQGASMVDVENM</u>FGGGTEVVVK

226E12 CHIMERIC HEAVY CHAIN FULL-LENGTH NUCLEOTIDE SEQUENCE
SEQ ID NO: 5
CAGTCGCTGGAGGAGTCCGGGGGTCGCCTGGTCACGCCTGGGACACCCCTGACACTCACCTGCACAGCCTCTGAA

TTCTCCCTCAGTAACTACTACATGAGCTGGGTCCGCCAGGCTCCAGGGGAGGGGCTGGAGTGGATCGGAGCCATT

AATGCTGACAGTGATAATACATGGTACCCGAGCTGGGTGAAAGGCCGATTCACCATCTCCAAACCTCGTCGACC

ACGGTGGATCTGAAGATCACCAGTCCGACAATTGAGGACACGGCCACCTATTTCTGTGCCAGAAGTGTGAGTAAT

AATTTCGCCGAATATAACATCTGGGGCCCGGGCACCCTGGTCACCGTCTCGAGCGCTAGCACCAAGGGCCCATCG

GTCTTCCCCCTGGCACCCTCCTCCAAGAGCACCTCTGGGGGCACAGCGGCCCTGGGCTGCCTGGTCAAGGACTAC

TTCCCCGAACCGGTGACGGTGTCGTGGAACTCAGGCGCCCTGACCAGCGGCGTGCACACCTTCCCGGCTGTCCTA

CAGTCCTCAGGACTCTACTCCCTCAGCAGCGTGGTGACCGTGCCCTCCAGCAGCTTGGGCACCCAGACCTACATC

TGCAACGTGAATCACAAGCCCAGCAACACCAAGGTGGACAAGAGAGTTGAGCCCAAATCTTGTGACAAAACTCAC

ACATGCCCACCGTGCCCAGCACCTGAAGCCGCGGGGCACCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTGAGGTCAAG

TTCAACTGGTACGTGGACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTACAAGTGCGCGGTCTCC

AACAAAGCCCTCCCAGCCCCCATCGAGAAAACCATCTCCAAAGCCAAAGGGCAGCCCCGAGAACCACAGGTGTAC

-continued

ACCCTGCCCCCATCCCGGGATGAGCTGACCAAGAACCAGGTCAGCCTGACCTGCCTGGTCAAAGGCTTCTATCCC

AGCGACATCGCCGTGGAGTGGGAGAGCAATGGGCAGCCGGAGAACAACTACAAGACCACGCCTCCCGTGCTGGAC

TCCGACGGCTCCTTCTTCCTCTATAGCAAGCTCACCGTGGACAAGAGCAGGTGGCAGCAGGGGAACGTCTTCTCA

TGCTCCGTGATGCATGAGGCTCTGCACAACCACTACACGCAGAAGAGCCTCTCCCTGTCTCCGGGT

226E12 CHIMERIC HEAVY CHAIN VARIABLE HEAVY CHAIN NUCLEOTIDE
SEQUENCE
SEQ ID NO: 6
CAGTCGCTGGAGGAGTCCGGGGGTCGCCTGGTCACGCCTGGGACACCCCTGACACTCACCTGCACAGCCTCTGAA

TTCTCCCTCAGTAACTACTACATGAGCTGGGTCCGCCAGGCTCCAGGGGAGGGGCTGGAGTGGATCGGAGCCATT

AATGCTGACAGTGATAATACATGGTACCCGAGCTGGGTGAAAGGCCGATTCACCATCTCCAAAACCTCGTCGACC

ACGGTGGATCTGAAGATCACCAGTCCGACAATTGAGGACACGGCCACCTATTTCTGTGCCAGAAGTGTGAGTAAT

AATTTCGCCGAATATAACATCTGGGGCCCGGGCACCCTGGTCACCGTCTCGAGC

226E12 CHIMERIC HEAVY CHAIN FULL-LENGTH AMINO ACID SEQUENCE.
HUMAN GAMMA-1 CONSTANT DOMAIN IS UNDERLINED
SEQ ID NO: 7
QSLEESGGRLVTPGTPLTLTCTASEFSLSNYYMSWVRQAPGEGLEWIGAINADSDNTWYPSWVKGRFTISKTSST

TVDLKITSPTIEDTATYFCARSVSNNFAEYNIWGPGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKRVEPKSCDKTH

TCPPCPAPEAAGAPSVFLFPPKPKDTLMISRTPEVTCVVVDVSHEDPEVKFNWYVDGVEVHNAKTKPREEQYNST

YRVVSVLTVLHQDWLNGKEYKCAVSNKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFSCSVMHEALHNHYTQKSLSLSPG

226E12 CHIMERIC HEAVY CHAIN VARIABLE HEAVY CHAIN AMINO ACID
SEQUENCE. COMPLIMENTARITY DETERMINING REGIONS ARE UNDERLINED
SEQ ID NO: 8
QSLEESGGRLVTPGTPLTLTCTASEFSLSNYYMSWVRQAPGEGLEWIGAINADSDNTWYPSWVKGRFTISKTSST

TVDLKITSPTIEDTATYFCARSVSNNFAEYNIWGPGTLVTVSS

323H7 CHIMERIC LIGHT CHAIN FULL-LENGTH NUCLEOTIDE SEQUENCE
SEQ ID NO: 9
CAAGCCGTGGTGACCCAGACTCCATCGTCCGTGTCTGCAGCTGTGGGAGGCACAGTCACCATCAGTTGCCAGTCC

AGTCAGAGTGTTTATAACAACAACGACTTAGCCTGGTATCAGCAGAAACCAGGGCAGCCTCCCAAGCTCCTGATC

TACTATGCATCCACTCTGGCATCTGGGGTCTCATCGCGGTTCAAAGGCAGTGGATCTGGGACACAGTTCACTCTC

GCCATCAGCGACCTGGAGTGTGACGATTCTGCCACTTACTACTGTGCAGGCGGTTATGATACGGATGGTCTTGAT

ACGTTTGCTTTCGGCGGAGGCACCGAGGTGGAGGTCAAACGTACGGTGGCTGCACCATCTGTCTTCATCTTCCCG

CCATCTGATGAGCAGTTGAAATCTGGAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGAGAGTGTCACAGAGCAGGACAGCAAG

GACAGCACCTACAGCCTCAGCAGCACCCTGACGCTGAGCAAAGCAGACTACGAGAAACACAAAGTCTACGCCTGC

GAAGTCACCCATCAGGGCCTGAGCTCGCCCGTCACAAAGAGCTTCAACAGGGGAGAGTGT

323H7 CHIMERIC LIGHT CHAIN VARIABLE LIGHT CHAIN NUCLEOTIDE
SEQUENCE
SEQ ID NO: 10
CAAGCCGTGGTGACCCAGACTCCATCGTCCGTGTCTGCAGCTGTGGGAGGCACAGTCACCATCAGTTGCCAGTCC

AGTCAGAGTGTTTATAACAACAACGACTTAGCCTGGTATCAGCAGAAACCAGGGCAGCCTCCCAAGCTCCTGATC

TACTATGCATCCACTCTGGCATCTGGGGTCTCATCGCGGTTCAAAGGCAGTGGATCTGGGACACAGTTCACTCTC

GCCATCAGCGACCTGGAGTGTGACGATTCTGCCACTTACTACTGTGCAGGCGGTTATGATACGGATGGTCTTGAT

ACGTTTGCTTTCGGCGGAGGCACCGAGGTGGAGGTCAAA

323H7 CHIMERIC LIGHT CHAIN FULL-LENGTH AMINO ACID SEQUENCE.
HUMAN KAPPA CONSTANT DOMAIN IS UNDERLINED
SEQ ID NO: 11
QAVVTQTPSSVSAAVGGTVTISCQSSQSVYNNNDLAWYQQKPGQPPKLLIYYASTLASGVSSRFKGSGSGTQFTL

AISDLECDDSATYYCAGGYDTDGLDTFAFGGGTEVEVKRTVAAPSVFIFPPSDEQLKSGTASVVCLLNNFYPREA

KVQWKVDNALQSGNSQESVTEQDSKDSTYSLSSTLTLSKADYEKHKVYACEVTHQGLSSPVTKSFNRGEC

323H7 CHIMERIC LIGHT CHAIN VARIABLE LIGHT CHAIN AMINO ACID
SEQUENCE. COMPIMENTARITY DETERMINING REGIONS ARE UNDERLINED
SEQ ID NO: 12
QAVVTQTPSSVSAAVGGTVTISCQSSQSVYNNNDLAWYQQKPGQPPKLLIYYASTLASGVSSRFKGSGSGTQFTL

AISDLECDDSATYYCAGGYDTDGLDTFAFGGGTEVEVK

323H7 CHIMERIC HEAVY CHAIN FULL-LENGTH NUCLEOTIDE SEQUENCE
SEQ ID NO: 13
CAGGAGCAGCTGAAGGAGTCCGGAGGAGGCCTGGTAACGCCTGGAGGAACCCTGACACTCACCTGCACAGCCTCT

GGATTCACCATCAGTCGCTACCACATGACTTGGGTCCGCCAGGCTCCAGGGAAGGGGCTGGAGTGGATCGGTCAT

ATTTATGTTAATAATGATGACACAGACTACGCGAGCTGGGCGAAAGGCCGATTCACCATCTCCAAAACCTCGACC

ACGGTGGATCTGAAGATCACCAGTCCGACAACCGAGGACACGGCCACCTATTTCTGTGCCAGATTGGATGTTGGT

GGTGGTGGTGCTTATATTGGGGACATCTGGGGCCAAGGGACCCTGGTCACCGTCTCGAGCGCTAGCACCAAGGGC

CCATCGGTCTTCCCCCTGGCACCCTCCTCCAAGAGCACCTCTGGGGGCACAGCGGCCCTGGGCTGCCTGGTCAAG

GACTACTTCCCCGAACCGGTGACGGTGTCGTGGAACTCAGGCGCCCTGACCAGCGGCGTGCACACCTTCCCGGCT

GTCCTACAGTCCTCAGGACTCTACTCCCTCAGCAGCGTGGTGACCGTGCCCTCCAGCAGCTTGGGCACCCAGACC

TACATCTGCAACGTGAATCACAAGCCCAGCAACACCAAGGTGGACAAGAGAGTTGAGCCCAAATCTTGTGACAAA

ACTCACACATGCCCACCGTGCCCAGCACCTGAAGCCGCGGGGGCACCGTCAGTCTTCCTCTTCCCCCCAAAACCC

AAGGACACCCTCATGATCTCCCGGACCCCTGAGGTCACATGCGTGGTGGTGGACGTGAGCCACGAAGACCCTGAG

GTCAAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGCGCG

GTCTCCAACAAAGCCCTCCCAGCCCCCATCGAGAAAACCATCTCCAAAGCCAAAGGGCAGCCCCGAGAACCACAG

GTGTACACCCTGCCCCCATCCCGGGATGAGCTGACCAAGAACCAGGTCAGCCTGACCTGCCTGGTCAAAGGCTTC

TATCCCAGCGACATCGCCGTGGAGTGGGAGAGCAATGGGCAGCCGGAGAACAACTACAAGACCACGCCTCCCGTG

CTGGACTCCGACGGCTCCTTCTTCCTCTATAGCAAGCTCACCGTGGACAAGAGCAGGTGGCAGCAGGGGAACGTC

TTCTCATGCTCCGTGATGCATGAGGCTCTGCACAACCACTACACGCAGAAGAGCCTCTCCCTGTCTCCGGGT

323H7 CHIMERIC HEAVY CHAIN VARIABLE HEAVY CHAIN NUCLEOTIDE
SEQUENCE
SEQ ID NO: 14
CAGGAGCAGCTGAAGGAGTCCGGAGGAGGCCTGGTAACGCCTGGAGGAACCCTGACACTCACCTGCACAGCCTCT

GGATTCACCATCAGTCGCTACCACATGACTTGGGTCCGCCAGGCTCCAGGGAAGGGGCTGGAGTGGATCGGTCAT

ATTTATGTTAATAATGATGACACAGACTACGCGAGCTGGGCGAAAGGCCGATTCACCATCTCCAAAACCTCGACC

ACGGTGGATCTGAAGATCACCAGTCCGACAACCGAGGACACGGCCACCTATTTCTGTGCCAGATTGGATGTTGGT

GGTGGTGGTGCTTATATTGGGGACATCTGGGGCCAAGGGACCCTGGTCACCGTCTCGAGC

323H7 CHIMERIC HEAVY CHAIN FULL-LENGTH AMINO ACID SEQUENCE.
HUMAN GAMMA-1 CONSTANT DOMAIN IS UNDERLINED
SEQ ID NO: 15
QEQLKESGGGLVTPGGTLTLTCTASGFTISRYHMTWVRQAPGKGLEWIGHIYVNNDDTDYASWAKGRFTISKTST

TVDLKITSPTTEDTATYFCARLDVGGGGAYIGDIWGQGTLVTVSSASTKGPSVFPLAPSSKSTSGGTAALGCLVK

DYFPEPVTVSWNSGALTSGVHTFPAVLQSSGLYSLSSVVTVPSSSLGTQTYICNVNHKPSNTKVDKRVEPKSCDK

THTCPPCPAPEAAGAPSVFLFPPKPKDTLMISRTPEVTCVVVDVSHEDPEVKFNWYVDGVEVHNAKTKPREEQYN

STYRVVSVLTVLHQDWLNGKEYKCAVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALHNHYTQKSLSLSPG

323H7 CHIMERIC HEAVY CHAIN VARIABLE HEAVY CHAIN AMINO ACID
SEQUENCE. COMPLIMENTARITY DETERMINING REGIONS ARE UNDERLINED
SEQ ID NO: 16
QEQLKESGGGLVTPGGTLTLTCTASGFTISRYHMTWVRQAPGKGLEWIGHIYVNNDDTDYASWAKGRFTISKTST

TVDLKITSPTTEDTATYFCARLDVGGGGAYIGDIWGQGTLVTVSS

324C7 CHIMERIC LIGHT CHAIN FULL-LENGTH NUCLEOTIDE SEQUENCE
SEQ ID NO: 17
GACATTGTGATGACCCAGACTCCAGCCTCTGTGGAGGTCGCTGTGGGAGGCACAGTCACCATCAAGTGCCAGGCC

AGTCAGAACATTGGTAGTGATTTAGCCTGGTATCAGCAGAAACCAGGGCAGCCTCCCAAGCTCCTGATCTATACT

ACATCCAATCTGGCATCTGGGGTCCCATCGCGGTTCAAAGGCAGTGGATCTGGGACAGGTTTCACTCTCACCATC

AGCGACCTGGAGTGTGCCGATGCTGCCAGTTACTGCTGTCAAGGCGGTTATTTTAGTGGTCGTAATATTTATGGG

AATGCTTTCGGCGGAGGCACCGAGGTGGTGGTCAAACGTACGGTGGCTGCACCATCTGTCTTCATCTTCCCGCCA

TCTGATGAGCAGTTGAAATCTGGAACTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAGTGTCACAGAGCAGGACAGCAAGGAC

AGCACCTACAGCCTCAGCAGCACCCTGACGCTGAGCAAAGCAGACTACGAGAAACACAAAGTCTACGCCTGCGAA

GTCACCCATCAGGGCCTGAGCTCGCCCGTCACAAAGAGCTTCAACAGGGGAGAGTGT

324C7 CHIMERIC LIGHT CHAIN VARIABLE LIGHT CHAIN NUCLEOTIDE
SEQUENCE
SEQ ID NO: 18
GACATTGTGATGACCCAGACTCCAGCCTCTGTGGAGGTCGCTGTGGGAGGCACAGTCACCATCAAGTGCCAGGCC

AGTCAGAACATTGGTAGTGATTTAGCCTGGTATCAGCAGAAACCAGGGCAGCCTCCCAAGCTCCTGATCTATACT

ACATCCAATCTGGCATCTGGGGTCCCATCGCGGTTCAAAGGCAGTGGATCTGGGACAGGTTTCACTCTCACCATC

AGCGACCTGGAGTGTGCCGATGCTGCCAGTTACTGCTGTCAAGGCGGTTATTTTAGTGGTCGTAATATTTATGGG

AATGCTTTCGGCGGAGGCACCGAGGTGGTGGTCAAA

324C7 CHIMERIC LIGHT CHAIN FULL-LENGTH AMINO ACID SEQUENCE.
HUMAN KAPPA CONSTANT DOMAIN IS UNDERLINED
SEQ ID NO: 19
DIVMTQTPASVEVAVGGTVTIKCQASQNIGSDLAWYQQKPGQPPKLLIYTTSNLASGVPSRFKGSGSGTGFTLTI

SDLECADAASYCCQGGYFSGRNIYGNAFGGGTEVVVKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSFNRGEC

324C7 CHIMERIC LIGHT CHAIN VARIABLE LIGHT CHAIN AMINO ACID
SEQUENCE. COMPIMENTARITY DETERMINING REGIONS ARE UNDERLINED
SEQ ID NO: 20
DIVMTQTPASVEVAVGGTVTIKCQASQNIGSDLAWYQQKPGQPPKLLIYTTSNLASGVPSRFKGSGSGTGFTLTI

SDLECADAASYCCQGGYFSGRNIYGNAFGGGTEVVVK

324C7 CHIMERIC HEAVY CHAIN FULL-LENGTH NUCLEOTIDE SEQUENCE
SEQ ID NO: 21
CAGTCGGTGGAGGAGTCCGGGGGTCGCCTGGTCACGCCTGGGACACCCCTGACACTCACCTGCACAGTCTCTGGA

TTCTCCCTCAGTGGCGCTGGAGTGAGCTGGGTCCGCCAGGCTCCAGGGAAGGGGCTGGAGTGGATCGGATACATT

GATAGTGGTGCTACCACATACTACGCGAGCTGGGCAAAAGGCCGATTCACCATCTCCAAAGCCTCGACCACGGTG

GATCTGAAAATCGCCAGTCCGACAACCGAGGACACGGCCACCTATTTCTGTGCCAGAGGATACTACGGCATGGAC

CCCTGGGGCCAAGGCACCCTGGTCACCGTCTCGAGCGCTAGCACCAAGGGCCCATCGGTCTTCCCCCTGGCACCC

TCCTCCAAGAGCACCTCTGGGGGCACAGCGGCCCTGGGCTGCCTGGTCAAGGACTACTTCCCCGAACCGGTGACG

GTGTCGTGGAACTCAGGCGCCCTGACCAGCGGCGTGCACACCTTCCCGGCTGTCCTACAGTCCTCAGGACTCTAC

TCCCTCAGCAGCGTGGTGACCGTGCCCTCCAGCAGCTTGGGCACCCAGACCTACATCTGCAACGTGAATCACAAG

CCCAGCAACACCAAGGTGGACAAGAGAGTTGAGCCCAAATCTTGTGACAAAACTCACACATGCCCACCGTGCCCA

```
GCACCTGAAGCCGCGGGGGCACCGTCAGTCTTCCTCTTCCCCCCAAAACCCAAGGACACCCTCATGATCTCCCGG

ACCCCTGAGGTCACATGCGTGGTGGTGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAACAGCACGTACCGTGTGGTCAGCGTC

CTCACCGTCCTGCACCAGGACTGGCTGAATGGCAAGGAGTACAAGTGCGCGGTCTCCAACAAAGCCCTCCCAGCC

CCCATCGAGAAAACCATCTCCAAAGCCAAAGGGCAGCCCCGAGAACCACAGGTGTACACCCTGCCCCCATCCCGG

GATGAGCTGACCAAGAACCAGGTCAGCCTGACCTGCCTGGTCAAAGGCTTCTATCCCAGCGACATCGCCGTGGAG

TGGGAGAGCAATGGGCAGCCGGAGAACAACTACAAGACCACGCCTCCCGTGCTGGACTCCGACGGCTCCTTCTTC

CTCTATAGCAAGCTCACCGTGGACAAGAGCAGGTGGCAGCAGGGGAACGTCTTCTCATGCTCCGTGATGCATGAG

GCTCTGCACAACCACTACACGCAGAAGAGCCTCTCCCTGTCTCCGGGT
```

324C7 CHIMERIC HEAVY CHAIN VARIABLE HEAVY CHAIN NUCLEOTIDE
SEQUENCE
                                                        SEQ ID NO: 22
```
CAGTCGGTGGAGGAGTCCGGGGGTCGCCTGGTCACGCCTGGGACACCCCTGACACTCACCTGCACAGTCTCTGGA

TTCTCCCTCAGTGGCGCTGGAGTGAGCTGGGTCCGCCAGGCTCCAGGGAAGGGGCTGGAGTGGATCGGATACATT

GATAGTGGTGCTACCACATACTACGCGAGCTGGGCAAAAGGCCGATTCACCATCTCCAAAGCCTCGACCACGGTG

GATCTGAAAATCGCCAGTCCGACAACCGAGGACACGGCCACCTATTTCTGTGCCAGAGGATACTACGGCATGGAC

CCCTGGGGCCAAGGCACCCTGGTCACCGTCTCGAGC
```

324C7 CHIMERIC HEAVY CHAIN FULL-LENGTH AMINO ACID SEQUENCE.
HUMAN GAMMA-1 CONSTANT DOMAIN IS UNDERLINED
                                                        SEQ ID NO: 23
QSVEESGGRLVTPGTPLTLTCTVSGFSLSGAGVSWVRQAPGKGLEWIGYIDSGATTYYASWAKGRFTISKASTTV

DLKIASPTTEDTATYFCARGYYGMDPWGQGTLVTVSS<u>ASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCP

APEAAGAPSVFLFPPKPKDTLMISRTPEVTCVVVDVSHEDPEVKFNWYVDGVEVHNAKTKPREEQYNSTYRVVSV

LTVLHQDWLNGKEYKCAVSNKALPAPIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHEALHNHYTQKSLSLSPG</u>

324C7 CHIMERIC HEAVY CHAIN VARIABLE HEAVY CHAIN AMINO ACID
SEQUENCE. COMPLIMENTARITY DETERMINING REGIONS ARE UNDERLINED
                                                        SEQ ID NO: 24
QSVEESGGRLVTPGTPLTLTCTVSGFSLS<u>GAGVS</u>WVRQAPGKGLEWIG<u>YIDSGATTYYASWAKG</u>RFTISKASTTV

DLKIASPTTEDTATYFCAR<u>GYYGMDP</u>WGQGTLVTVSS

323D10 CHIMERIC LIGHT CHAIN FULL-LENGTH NUCLEOTIDE SEQUENCE
                                                        SEQ ID NO: 25
```
GCCATCGATTTGACCCAGACTCCAGCCTCCGTGGAGGCAGCTGTGGGAGGCACAATCACCATCAATTGCCAAGCC

AGTGAGAGCATTAGCAGTTGGTTAGCCTGGTATCAGCAGAAACCAGGGCAGCGTCCCAAGCTCCTGATCTACGAA

ACATCCAAACTGGCATCTGGGGTCCCACCGCGGTTCAGCGGCAGTGGATCTGGGACACAGTTCACTCTCACCATC

AGCGGCGTGCAGTGTGACGATGCTGCCACTTACTACTGTCAAAGTTATTATCGTATTAATAATATTGGTTACGAT

AATGCTTTCGGCGGAGGCACCGAGGTGGAGTTCAAACGTACGGTGGCTGCACCATCTGTCTTCATCTTCCCGCCA

TCTGATGAGCAGTTGAAATCTGGAACTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAGTGTCACAGAGCAGGACAGCAAGGAC

AGCACCTACAGCCTCAGCAGCACCCTGACGCTGAGCAAAGCAGACTACGAGAAACACAAAGTCTACGCCTGCGAA

GTCACCCATCAGGGCCTGAGCTCGCCCGTCACAAAGAGCTTCAACAGGGGAGAGTGT
```

323D10 CHIMERIC LIGHT CHAIN VARIABLE LIGHT CHAIN NUCLEOTIDE
SEQUENCE
                                                        SEQ ID NO: 26
```
GCCATCGATTTGACCCAGACTCCAGCCTCCGTGGAGGCAGCTGTGGGAGGCACAATCACCATCAATTGCCAAGCC

AGTGAGAGCATTAGCAGTTGGTTAGCCTGGTATCAGCAGAAACCAGGGCAGCGTCCCAAGCTCCTGATCTACGAA

ACATCCAAACTGGCATCTGGGGTCCCACCGCGGTTCAGCGGCAGTGGATCTGGGACACAGTTCACTCTCACCATC
```

AGCGGCGTGCAGTGTGACGATGCTGCCACTTACTACTGTCAAAGTTATTATCGTATTAATAATATTGGTTACGAT

AATGCTTTCGGCGGAGGCACCGAGGTGGAGTTCAAA

323D10 CHIMERIC LIGHT CHAIN FULL-LENGTH AMINO ACID SEQUENCE.
HUMAN KAPPA CONSTANT DOMAIN IS UNDERLINED

SEQ ID NO: 27

AIDLTQTPASVEAAVGGTITINCQASESISSWLAWYQQKPGQRPKLLIYETSKLASGVPPRFSGSGSGTQFTLTI

SGVQCDDAATYYCQSYYRINNIGYDNAFGGGTEVEFK<u>RTVAAPSVFIFPPSDEQLKSGTASVVCLLNNFYPREAK</u>

<u>VQWKVDNALQSGNSQESVTEQDSKDSTYSLSSTLTLSKADYEKHKVYACEVTHQGLSSPVTKSFNRGEC</u>

323D10 CHIMERIC LIGHT CHAIN VARIABLE LIGHT CHAIN AMINO ACID
SEQUENCE. COMPIMENTARITY DETERMINING REGIONS ARE UNDERLINED

SEQ ID NO: 28

AIDLTQTPASVEAAVGGTITINC<u>QASESISSWLA</u>WYQQKPGQRPKLLIY<u>ETSKLAS</u>GVPPRFSGSGSGTQFTLTI

SGVQCDDAATYYC<u>QSYYRINNIGYDNA</u>FGGGTEVEFK

323D10 CHIMERIC HEAVY CHAIN FULL-LENGTH NUCLEOTIDE SEQUENCE

SEQ ID NO: 29

CAGTCGGTGGAGGAGTCCGGGGGTCGCCTGGTCACGCCTGGGACACCCCTGACACTCACCTGCACCGTCTCTGGA

TTCTCCCTCAGTAGGAATGCAATGAACTGGGTCCGCCAGGCTCCAGGGAAGGGGCTGGAATACATCGGATACATT

AGCACTAGTGGTACCACATTCTACGCGAACTGGGTGAAAGGCCGATTCACCATCTCCAAAACCTCGACCACGGTG

GATCTGAAAATGACCAGTCTGACAACCGAGGACACGGCCACCTATTTCTGTGCCAGAGACTATAACTACGCCATG

GACATCTGGGGCCAAGGCACCCTGGTCACCGTCTCGAGCGCTAGCACCAAGGGCCCATCGGTCTTCCCCCTGGCA

CCCTCCTCCAAGAGCACCTCTGGGGGCACAGCGGCCCTGGGCTGCCTGGTCAAGGACTACTTCCCCGAACCGGTG

ACGGTGTCGTGGAACTCAGGCGCCCTGACCAGCGGCGTGCACACCTTCCCGGCTGTCCTACAGTCCTCAGGACTC

TACTCCCTCAGCAGCGTGGTGACCGTGCCCTCCAGCAGCTTGGGCACCCAGACCTACATCTGCAACGTGAATCAC

AAGCCCAGCAACACCAAGGTGGACAAGAGAGTTGAGCCCAAATCTTGTGACAAAACTCACACATGCCCACCGTGC

CCAGCACCTGAAGCCGCGGGGGCACCGTCAGTCTTCCTCTTCCCCCCAAAACCCAAGGACACCCTCATGATCTCC

CGGACCCCTGAGGTCACATGCGTGGTGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTACAACAGCACGTACCGTGTGGTCAGC

GTCCTCACCGTCCTGCACCAGGACTGGCTGAATGGCAAGGAGTACAAGTGCGCGGTCTCCAACAAAGCCCTCCCA

GCCCCCATCGAGAAAACCATCTCCAAAGCCAAAGGGCAGCCCCGAGAACCACAGGTGTACACCCTGCCCCCATCC

CGGGATGAGCTGACCAAGAACCAGGTCAGCCTGACCTGCCTGGTCAAAGGCTTCTATCCCAGCGACATCGCCGTG

GAGTGGGAGAGCAATGGGCAGCCGGAGAACAACTACAAGACCACGCCTCCCGTGCTGGACTCCGACGGCTCCTTC

TTCCTCTATAGCAAGCTCACCGTGGACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGGT

323D10 CHIMERIC HEAVY CHAIN VARIABLE HEAVY CHAIN NUCLEOTIDE
SEQUENCE

SEQ ID NO: 30

CAGTCGGTGGAGGAGTCCGGGGGTCGCCTGGTCACGCCTGGGACACCCCTGACACTCACCTGCACCGTCTCTGGA

TTCTCCCTCAGTAGGAATGCAATGAACTGGGTCCGCCAGGCTCCAGGGAAGGGGCTGGAATACATCGGATACATT

AGCACTAGTGGTACCACATTCTACGCGAACTGGGTGAAAGGCCGATTCACCATCTCCAAAACCTCGACCACGGTG

GATCTGAAAATGACCAGTCTGACAACCGAGGACACGGCCACCTATTTCTGTGCCAGAGACTATAACTACGCCATG

GACATCTGGGGCCAAGGCACCCTGGTCACCGTCTCGAGC

323D10 CHIMERIC HEAVY CHAIN FULL-LENGTH AMINO ACID SEQUENCE.
HUMAN GAMMA-1 CONSTANT DOMAIN IS UNDERLINED

SEQ ID NO: 31

QSVEESGGRLVTPGTPLTLTCTVSGFSLSRNAMNWVRQAPGKGLEYIGYISTSGTTFYANWVKGRFTISKTSTTV

DLKMTSLTTEDTATYFCARDYNYAMDIWGQGTLVTVSS<u>ASTKGPSVFPLAPSSKSTSGGTAALGCLVKDYFPEPV</u>

<u>TVSWNSGALTSGVHTFPAVLQSSGLYSLSSVVTVPSSSLGTQTYICNVNHKPSNTKVDKRVEPKSCDKTHTCPPC</u>

```
                                     -continued
PAPEAAGAPSVFLFPPKPKDTLMISRTPEVTCVVVDVSHEDPEVKFNWYVDGVEVHNAKTKPREEQYNSTYRVVS

VLTVLHQDWLNGKEYKCAVSNKALPAPIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMHEALHNHYTQKSLSLSPG

323D10 CHIMERIC HEAVY CHAIN VARIABLE HEAVY CHAIN AMINO ACID
SEQUENCE. COMPLIMENTARITY DETERMINING REGIONS ARE UNDERLINED
                                                        SEQ ID NO: 32
QSVEESGGRLVTPGTPLTLTCTVSGFSLSRNAMNWVRQAPGKGLEYIGYISTSGTTFYANWVKGRFTISKTSTTV

DLKMTSLTTEDTATYFCARDYNYAMDIWGQGTLVTVSS

324E2 CHIMERIC LIGHT CHAIN FULL-LENGTH NUCLEOTIDE SEQUENCE
                                                        SEQ ID NO: 33
GCTCAAGTGCTGACCCAGACTCCATCCTCCGTGTCTGCAGCTGTGGGAGGCACAGTCACCATCAATTGCCAGTCC

AGTCAGAGTGTTAATAACAACGACTTAGCCTGGTTTCAGCAGAAACCAGGGCAGCCTCCCAAGCGCCTGATCTAC

TGGGCATCCAAACTGGCATCTGGGGTCCCATCGCGGTTCAAAGGCAGTGGATCTGGGACACAGTTCATTCTCACC

ATCAGCGACCTGGAGTGTGACGATGCTGCCACTTACTACTGTGCAGGCGGTTATAGTGGTAATATTTATGGTTTC

GGCGGAGGCACCGAGGTGGAGGTCAAACGTACGGTGGCTGCACCATCTGTCTTCATCTTCCCGCCATCTGATGAG

CAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTACGCCTGCGAAGTCACCCAT

CAGGGCCTGAGCTCGCCCGTCACAAAGAGCTTCAACAGGGGAGAGTGT

324E2 CHIMERIC LIGHT CHAIN VARIABLE LIGHT CHAIN NUCLEOTIDE
SEQUENCE
                                                        SEQ ID NO: 34
GCTCAAGTGCTGACCCAGACTCCATCCTCCGTGTCTGCAGCTGTGGGAGGCACAGTCACCATCAATTGCCAGTCC

AGTCAGAGTGTTAATAACAACGACTTAGCCTGGTTTCAGCAGAAACCAGGGCAGCCTCCCAAGCGCCTGATCTAC

TGGGCATCCAAACTGGCATCTGGGGTCCCATCGCGGTTCAAAGGCAGTGGATCTGGGACACAGTTCATTCTCACC

ATCAGCGACCTGGAGTGTGACGATGCTGCCACTTACTACTGTGCAGGCGGTTATAGTGGTAATATTTATGGTTTC

GGCGGAGGCACCGAGGTGGAGGTCAAA

324E2 CHIMERIC LIGHT CHAIN FULL-LENGTH AMINO ACID SEQUENCE.
HUMAN KAPPA CONSTANT DOMAIN IS UNDERLINED
                                                        SEQ ID NO: 35
AQVLTQTPSSVSAAVGGTVTINCQSSQSVNNNDLAWFQQKPGQPPKRLIYWASKLASGVPSRFKGSGSGTQFILT

ISDLECDDAATYYCAGGYSGNIYGFGGGTEVEVKRTVAAPSVFIFPPSDEQLKSGTASVVCLLNNFYPREAKVQW

KVDNALQSGNSQESVTEQDSKDSTYSLSSTLTLSKADYEKHKVYACEVTHQGLSSPVTKSFNRGEC

324E2 CHIMERIC LIGHT CHAIN VARIABLE LIGHT CHAIN AMINO ACID
SEQUENCE. COMPIMENTARITY DETERMINING REGIONS ARE UNDERLINED
                                                        SEQ ID NO: 36
AQVLTQTPSSVSAAVGGTVTINCQSSQSVNNNDLAWFQQKPGQPPKRLIYWASKLASGVPSRFKGSGSGTQFILT

ISDLECDDAATYYCAGGYSGNIYGFGGGTEVEVK

324E2 CHIMERIC HEAVY CHAIN FULL-LENGTH NUCLEOTIDE SEQUENCE
                                                        SEQ ID NO: 37
CAGTCGGTGGAGGAGTCCGGGGGTCGCCTGGTCACGCCTGGGACACCCCTGACACTCACCTGCACCGTCTCTGGA

TTCTCCCTCAGTAACAATGCAATAACCTGGGTCCGCCAGGCTCCAGGGAAGGGGCTGGAATACATCGGAATCATT

AGTAGTAGTGGTACCACATACTACGCGAGCTGGGCGAAAGGCCGATTCACCATCTCCAAAACCTCGTCGACCACG

GTGGATCTGAAAATGACCAGTCTGACAACCGAGGACACGGCCACCTATTTCTGTGCCGGAGCATTTAGCGTCTGG

GGCCCGGGCACCCTCGTCACCGTCTCGAGCGCTAGCACCAAGGGCCCATCGGTCTTCCCCCTGGCACCCTCCTCC

AAGAGCACCTCTGGGGGCACAGCGGCCCTGGGCTGCCTGGTCAAGGACTACTTCCCCGAACCGGTGACGGTGTCG

TGGAACTCAGGCGCCCTGACCAGCGGCGTGCACACCTTCCCGGCTGTCCTACAGTCCTCAGGACTCTACTCCCTC

AGCAGCGTGGTGACCGTGCCCTCCAGCAGCTTGGGCACCCAGACCTACATCTGCAACGTGAATCACAAGCCCAGC

AACACCAAGGTGGACAAGAGAGTTGAGCCCAAATCTTGTGACAAAACTCACACATGCCCACCGTGCCCAGCACCT
```

-continued

GAAGCCGCGGGGGCACCGTCAGTCTTCCTCTTCCCCCCAAAACCCAAGGACACCCTCATGATCTCCCGGACCCCT

GAGGTCACATGCGTGGTGGTGGACGTGAGCCACGAAGACCCTGAGGTCAAGTTCAACTGGTACGTGGACGGCGTG

GAGGTGCATAATGCCAAGACAAAGCCGCGGGAGGAGCAGTACAACAGCACGTACCGTGTGGTCAGCGTCCTCACC

GTCCTGCACCAGGACTGGCTGAATGGCAAGGAGTACAAGTGCGCGGTCTCCAACAAAGCCCTCCCAGCCCCCATC

GAGAAAACCATCTCCAAAGCCAAAGGGCAGCCCCGAGAACCACAGGTGTACACCCTGCCCCCATCCCGGGATGAG

CTGACCAAGAACCAGGTCAGCCTGACCTGCCTGGTCAAAGGCTTCTATCCCAGCGACATCGCCGTGGAGTGGGAG

AGCAATGGGCAGCCGGAGAACAACTACAAGACCACGCCTCCCGTGCTGGACTCCGACGGCTCCTTCTTCCTCTAT

AGCAAGCTCACCGTGGACAAGAGCAGGTGGCAGCAGGGGAACGTCTTCTCATGCTCCGTGATGCATGAGGCTCTG

CACAACCACTACACGCAGAAGAGCCTCTCCCTGTCTCCGGGT

324E2 CHIMERIC HEAVY CHAIN VARIABLE HEAVY CHAIN NUCLEOTIDE
SEQUENCE
SEQ ID NO: 38
CAGTCGGTGGAGGAGTCCGGGGGTCGCCTGGTCACGCCTGGGACACCCCTGACACTCACCTGCACCGTCTCTGGA

TTCTCCCTCAGTAACAATGCAATAACCTGGGTCCGCCAGGCTCCAGGGAAGGGGCTGGAATACATCGGAATCATT

AGTAGTAGTGGTACCACATACTACGCGAGCTGGGCGAAAGGCCGATTCACCATCTCCAAAACCTCGTCGACCACG

GTGGATCTGAAAATGACCAGTCTGACAACCGAGGACACGGCCACCTATTTCTGTGCCGGAGCATTTAGCGTCTGG

GGCCCGGGCACCCTCGTCACCGTCTCGAGC

324E2 CHIMERIC HEAVY CHAIN FULL-LENGTH AMINO ACID SEQUENCE.
HUMAN GAMMA-1 CONSTANT DOMAIN IS UNDERLINED
SEQ ID NO: 39
QSVEESGGRLVTPGTPLTLTCTVSGFSLSNNAITWVRQAPGKGLEYIGIISSSGTTYYASWAKGRFTISKTSSTT

VDLKMTSLTTEDTATYFCAGAFSVWGPGTLVTVSS<u>ASTKGPSVFPLAPSSKSTSGGTAALGCLVKDYFPEPVTVS</u>

<u>WNSGALTSGVHTFPAVLQSSGLYSLSSVVTVPSSSLGTQTYICNVNHKPSNTKVDKRVEPKSCDKTHTCPPCPAP</u>

<u>EAAGAPSVFLFPPKPKDTLMISRTPEVTCVVVDVSHEDPEVKFNWYVDGVEVHNAKTKPREEQYNSTYRVVSVLT</u>

<u>VLHQDWLNGKEYKCAVSNKALPAPIEKTISKAKGQPREPQVYTLPPSRDELTKNQVSLTCLVKGFYPSDIAVEWE</u>

<u>SNGQPENNYKTTPPVLDSDGSFFLYSKLTVDKSRWQQGNVFSCSVMHEALHNHYTQKSLSLSPG</u>

324E2 CHIMERIC HEAVY CHAIN VARIABLE HEAVY CHAIN AMINO ACID
SEQUENCE. COMPLIMENTARITY DETERMINING REGIONS ARE UNDERLINED
SEQ ID NO: 40
QSVEESGGRLVTPGTPLTLTCTVSGFSLS<u>NNAIT</u>WVRQAPGKGLEYIGI<u>ISSSGTTYYASWAKG</u>RFTISKTSSTT

VDLKMTSLTTEDTATYFCAG<u>AFSV</u>WGPGTLVTVSS

324C6 CHIMERIC LIGHT CHAIN FULL-LENGTH NUCLEOTIDE SEQUENCE
SEQ ID NO: 41
GATGTTGTGATGACCCAGACTCCAGCCTCCGTGGAGGCAGCTGTGGGAGGCACAGTCACCATCAAGTGCCAGGCC

AGTCAGAGCATTGATAGTTGGTTATCCTGGTATCAACAGAAACCAGGGCAGCCTCCCAAGCTCCTGATCTACCAG

GCATCCACTCTGGCATCTGGGGTCTCATCGCGGTTCAAAGGCAGTGGATCTGGGACAGAGTTCACTCTCACCATC

AGCGACCTGGAGTGTGCCGATGCTGCCACTTACTACTGTCAATGCGCTTATGGTGTTAGTGGTACTAGTAGTTAT

TTATATACTTTCGGCGGAGGCACCGAGGTGGAGGTCAAACGTACGGTGGCTGCACCATCTGTCTTCATCTTCCCG

CCATCTGATGAGCAGTTGAAATCTGGAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGAGAGTGTCACAGAGCAGGACAGCAAG

GACAGCACCTACAGCCTCAGCAGCACCCTGACGCTGAGCAAAGCAGACTACGAGAAACACAAAGTCTACGCCTGC

GAAGTCACCCATCAGGGCCTGAGCTCGCCCGTCACAAAGAGCTTCAACAGGGGAGAGTGT

324C6 CHIMERIC LIGHT CHAIN VARIABLE LIGHT CHAIN NUCLEOTIDE
SEQUENCE
SEQ ID NO: 42
GATGTTGTGATGACCCAGACTCCAGCCTCCGTGGAGGCAGCTGTGGGAGGCACAGTCACCATCAAGTGCCAGGCC

AGTCAGAGCATTGATAGTTGGTTATCCTGGTATCAACAGAAACCAGGGCAGCCTCCCAAGCTCCTGATCTACCAG

-continued

```
GCATCCACTCTGGCATCTGGGGTCTCATCGCGGTTCAAAGGCAGTGGATCTGGGACAGAGTTCACTCTCACCATC

AGCGACCTGGAGTGTGCCGATGCTGCCACTTACTACTGTCAATGCGCTTATGGTGTTAGTGGTACTAGTAGTTAT

TTATATACTTTCGGCGGAGGCACCGAGGTGGAGGTCAAA
```

324C6 CHIMERIC LIGHT CHAIN FULL-LENGTH AMINO ACID SEQUENCE.
HUMAN KAPPA CONSTANT DOMAIN IS UNDERLINED

SEQ ID NO: 43

DVVMTQTPASVEAAVGGTVTIKCQASQSIDSWLSWYQQKPGQPPKLLIYQASTLASGVSSRFKGSGSGTEFTLTI

SDLECADAATYYCQCAYGVSGTSSYLYTFGGGTEVEVK<u>RTVAAPSVFIFPPSDEQLKSGTASVVCLLNNFYPREA</u>

<u>KVQWKVDNALQSGNSQESVTEQDSKDSTYSLSSTLTLSKADYEKHKVYACEVTHQGLSSPVTKSFNRGEC</u>

324C6 CHIMERIC LIGHT CHAIN VARIABLE LIGHT CHAIN AMINO ACID
SEQUENCE. COMPIMENTARITY DETERMINING REGIONS ARE UNDERLINED

SEQ ID NO: 44

DVVMTQTPASVEAAVGGTVTIKC<u>QASQSIDSWLS</u>WYQQKPGQPPKLLIY<u>QASTLAS</u>GVSSRFKGSGSGTEFTLTI

SDLECADAATYYC<u>QCAYGVSGTSSYLYT</u>FGGGTEVEVK

324C6 CHIMERIC HEAVY CHAIN FULL-LENGTH NUCLEOTIDE SEQUENCE

SEQ ID NO: 45

```
CAGTCGCTGGAGGAGTCCGGGGGTCGCCTGGTCACGCCTGGGACACCCCTGACACTCACCTGCACAGCCTCTGGA

TTCTCCCTCAGTAGGTACTACATGACCTGGGTCCGCCAGGCTCCAGGGAAGGGGCTGGAGTGGATTGGAACCATT

TATACTAGTGGTAGTACATGGTACGCGAGCTGGACAAAAGGCCGATTCACCATCTCCAAAACCTCGACCACGGTG

GATCTGAAAATCACTAGTCCGACAACCGAGGACACGGCCACCTATTTCTGTGCCAGATCCTATTATGGCGGTGAT

AAGACTGGTTTAGGCATCTGGGGCCCAGGCACCCTCGTCACCGTCTCGAGCGCTAGCACCAAGGGCCCATCGGTC

TTCCCCCTGGCACCCTCCTCCAAGAGCACCTCTGGGGGCACAGCGGCCCTGGGCTGCCTGGTCAAGGACTACTTC

CCCGAACCGGTGACGGTGTCGTGGAACTCAGGCGCCCTGACCAGCGGCGTGCACACCTTCCCGGCTGTCCTACAG

TCCTCAGGACTCTACTCCCTCAGCAGCGTGGTGACCGTGCCCTCCAGCAGCTTGGGCACCCAGACCTACATCTGC

AACGTGAATCACAAGCCCAGCAACACCAAGGTGGACAAGAGAGTTGAGCCCAAATCTTGTGACAAAACTCACACA

TGCCCACCGTGCCCAGCACCTGAAGCCGCGGGGGCACCGTCAGTCTTCCTCTTCCCCCCAAAACCCAAGGACACC

CTCATGATCTCCCGGACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAGGAGTACAAGTGCGCGGTCTCCAAC

AAAGCCCTCCCAGCCCCCATCGAGAAAACCATCTCCAAAGCCAAAGGGCAGCCCCGAGAACCACAGGTGTACACC

CTGCCCCCATCCCGGGATGAGCTGACCAAGAACCAGGTCAGCCTGACCTGCCTGGTCAAAGGCTTCTATCCCAGC

GACATCGCCGTGGAGTGGGAGAGCAATGGGCAGCCGGAGAACAACTACAAGACCACGCCTCCCGTGCTGGACTCC

GACGGCTCCTTCTTCCTCTATAGCAAGCTCACCGTGGACAAGAGCAGGTGGCAGCAGGGGAACGTCTTCTCATGC

TCCGTGATGCATGAGGCTCTGCACAACCACTACACGCAGAAGAGCCTCTCCCTGTCTCCGGGT
```

324C6 CHIMERIC HEAVY CHAIN VARIABLE HEAVY CHAIN NUCLEOTIDE
SEQUENCE

SEQ ID NO: 46

```
CAGTCGCTGGAGGAGTCCGGGGGTCGCCTGGTCACGCCTGGGACACCCCTGACACTCACCTGCACAGCCTCTGGA

TTCTCCCTCAGTAGGTACTACATGACCTGGGTCCGCCAGGCTCCAGGGAAGGGGCTGGAGTGGATTGGAACCATT

TATACTAGTGGTAGTACATGGTACGCGAGCTGGACAAAAGGCCGATTCACCATCTCCAAAACCTCGACCACGGTG

GATCTGAAAATCACTAGTCCGACAACCGAGGACACGGCCACCTATTTCTGTGCCAGATCCTATTATGGCGGTGAT

AAGACTGGTTTAGGCATCTGGGGCCCAGGCACCCTCGTCACCGTCTCGAGC
```

324C6 CHIMERIC HEAVY CHAIN FULL-LENGTH AMINO ACID SEQUENCE.
HUMAN GAMMA-1 CONSTANT DOMAIN IS UNDERLINED

SEQ ID NO: 47

QSLEESGGRLVTPGTPLTLTCTASGFSLSRYYMTWVRQAPGKGLEWIGTIYTSGSTWYASWTKGRFTISKTSTTV

DLKITSPTTEDTATYFCARSYYGGDKTGLGIWGPGTLVTVSS<u>ASTKGPSVFPLAPSSKSTSGGTAALGCLVKDYF</u>

<u>PEPVTVSWNSGALTSGVHTFPAVLQSSGLYSLSSVVTVPSSSLGTQTYICNVNHKPSNTKVDKRVEPKSCDKTHT</u>

CPPCPAPEAAGAPSVFLFPPKPKDTLMISRTPEVTCVVVDVSHEDPEVKFNWYVDGVEVHNAKTKPREEQYNSTY

RVVSVLTVLHQDWLNGKEYKCAVSNKALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSCSVMHEALHNHYTQKSLSLSPG

324C6 CHIMERIC HEAVY CHAIN VARIABLE HEAVY CHAIN AMINO ACID
SEQUENCE. COMPLIMENTARITY DETERMINING REGIONS ARE UNDERLINED
SEQ ID NO: 48
QSLEESGGRLVTPGTPLTLTCTASGFSLSRYYMTWVRQAPGKGLEWIGTIYTSGSTWYASWTKGRFTISKTSTTV

DLKITSPTTEDTATYFCARSYYGGDKTGLGIWGPGTLVTVSS

338H4 CHIMERIC LIGHT CHAIN FULL-LENGTH NUCLEOTIDE SEQUENCE
SEQ ID NO: 49
GACATTGTGATGACCCAGACTCCAGCCTCGGTGTCTGCAGCTGTGGGAGGCACAGTCACCATCAATTGCCAGGCC

AGTCAGAACATTTACAGCTACTTATCCTGGTATCAGCAGAAACCAGGGCAGCCTCCCAAGCGCCTGATCTATCTG

GCATCTACTCTGGCATCTGGGGTCCCATCGCGGTTCAAAAGCAGTGGATCTGGGACAGAGTACACTCTCACCATC

AGCGACCTGGAGTGTGACGATGCTGCCACTTACTACTGTCAAAGCAATTATAACGGTAATTATGGTTTCGGCGGA

GGGACCGAGGTGGAGGTCAAACGTACGGTGGCTGCACCATCTGTCTTCATCTTCCCGCCATCTGATGAGCAGTTG

AAATCTGGAACTGCCTCTGTTGTGTGCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGACAGCAAGGACAGCACCTACAGCCTC

AGCAGCACCCTGACGCTGAGCAAAGCAGACTACGAGAAACACAAAGTCTACGCCTGCGAAGTCACCCATCAGGGC

CTGAGCTCGCCCGTCACAAAGAGCTTCAACAGGGGAGAGTGT

338H4 CHIMERIC LIGHT CHAIN VARIABLE LIGHT CHAIN NUCLEOTIDE
SEQUENCE
SEQ ID NO: 50
GACATTGTGATGACCCAGACTCCAGCCTCGGTGTCTGCAGCTGTGGGAGGCACAGTCACCATCAATTGCCAGGCC

AGTCAGAACATTTACAGCTACTTATCCTGGTATCAGCAGAAACCAGGGCAGCCTCCCAAGCGCCTGATCTATCTG

GCATCTACTCTGGCATCTGGGGTCCCATCGCGGTTCAAAAGCAGTGGATCTGGGACAGAGTACACTCTCACCATC

AGCGACCTGGAGTGTGACGATGCTGCCACTTACTACTGTCAAAGCAATTATAACGGTAATTATGGTTTCGGCGGA

GGGACCGAGGTGGAGGTCAAA

338H4 CHIMERIC LIGHT CHAIN FULL-LENGTH AMINO ACID SEQUENCE.
HUMAN KAPPA CONSTANT DOMAIN IS UNDERLINED
SEQ ID NO: 51
DIVMTQTPASVSAAVGGTVTINCQASQNIYSYLSWYQQKPGQPPKRLIYLASTLASGVPSRFKSSGSGTEYTLTI

SDLECDDAATYYCQSNYNGNYGFGGGTEVEVKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC

338H4 CHIMERIC LIGHT CHAIN VARIABLE LIGHT CHAIN AMINO ACID
SEQUENCE. COMPLIMENTARITY DETERMINING REGIONS ARE UNDERLINED
SEQ ID NO: 52
DIVMTQTPASVSAAVGGTVTINCQASQNIYSYLSWYQQKPGQPPKRLIYLASTLASGVPSRFKSSGSGTEYTLTI

SDLECDDAATYYCQSNYNGNYGFGGGTEVEVK

338H4 CHIMERIC HEAVY CHAIN FULL-LENGTH NUCLEOTIDE SEQUENCE
SEQ ID NO: 53
CAGTCGGTGGAGGAGTCCGGGGGTCGCCTGGTCACGCCTGGGACACCCCTGACACTCACCTGCACCGTCTCTGGA

TTCTCCCTCAGTAGCTATGCAATGAGCTGGGTCCGCCAGGCTCCAGGGAGGGGGCTGGAATGGATCGGAATCATT

TATGCTAGTGGTAGCACATACTACGCGAGCTGGGCGAAAGGCCGATTCACCATCTCCAAAACCTCGACCACGGTG

GATCTGAAAATCACCAGTCCGACAACCGAGGACACGGCCACCTATTTCTGTGCCAGAATTTATGACGGCATGGAC

CTCTGGGGCCCAGGGACCCTCGTCACCGTCTCGAGCGCTAGCACCAAGGGCCCATCGGTCTTCCCCCTGGCACCC

TCCTCCAAGAGCACCTCTGGGGGCACAGCGGCCCTGGGCTGCCTGGTCAAGGACTACTTCCCCGAACCGGTGACG

GTGTCGTGGAACTCAGGCGCCCTGACCAGCGGCGTGCACACCTTCCCGGCTGTCCTACAGTCCTCAGGACTCTAC

TCCCTCAGCAGCGTGGTGACCGTGCCCTCCAGCAGCTTGGGCACCCAGACCTACATCTGCAACGTGAATCACAAG

```
CCCAGCAACACCAAGGTGGACAAGAGAGTTGAGCCCAAATCTTGTGACAAAACTCACACATGCCCACCGTGCCCA

GCACCTGAAGCCGCGGGGGCACCGTCAGTCTTCCTCTTCCCCCCAAAACCCAAGGACACCCTCATGATCTCCCGG

ACCCCTGAGGTCACATGCGTGGTGGTGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAACAGCACGTACCGTGTGGTCAGCGTC

CTCACCGTCCTGCACCAGGACTGGCTGAATGGCAAGGAGTACAAGTGCGCGGTCTCCAACAAAGCCCTCCCAGCC

CCCATCGAGAAAACCATCTCCAAAGCCAAAGGGCAGCCCCGAGAACCACAGGTGTACACCCTGCCCCCATCCCGG

GATGAGCTGACCAAGAACCAGGTCAGCCTGACCTGCCTGGTCAAAGGCTTCTATCCCAGCGACATCGCCGTGGAG

TGGGAGAGCAATGGGCAGCCGGAGAACAACTACAAGACCACGCCTCCCGTGCTGGACTCCGACGGCTCCTTCTTC

CTCTATAGCAAGCTCACCGTGGACAAGAGCAGGTGGCAGCAGGGGAACGTCTTCTCATGCTCCGTGATGCATGAG

GCTCTGCACAACCACTACACGCAGAAGAGCCTCTCCCTGTCTCCGGGT
```

338H4 CHIMERIC HEAVY CHAIN VARIABLE HEAVY CHAIN NUCLEOTIDE SEQUENCE
SEQ ID NO: 54
```
CAGTCGGTGGAGGAGTCCGGGGGTCGCCTGGTCACGCCTGGGACACCCCTGACACTCACCTGCACCGTCTCTGGA

TTCTCCCTCAGTAGCTATGCAATGAGCTGGGTCCGCCAGGCTCCAGGGAGGGGGCTGGAATGGATCGGAATCATT

TATGCTAGTGGTAGCACATACTACGCGAGCTGGGCGAAAGGCCGATTCACCATCTCCAAAACCTCGACCACGGTG

GATCTGAAAATCACCAGTCCGACAACCGAGGACACGGCCACCTATTTCTGTGCCAGAATTTATGACGGCATGGAC

CTCTGGGGCCCAGGGACCCTCGTCACCGTCTCGAGC
```

338H4 CHIMERIC HEAVY CHAIN FULL-LENGTH AMINO ACID SEQUENCE.
HUMAN GAMMA-1 CONSTANT DOMAIN IS UNDERLINED
SEQ ID NO: 55
QSVEESGGRLVTPGTPLTLTCTVSGFSLSSYAMSWVRQAPGRGLEWIGIIYASGSTYYASWAKGRFTISKTSTTV

DLKITSPTTEDTATYFCARIYDGMDLWGPGTLVTVSS<u>ASTKGPSVFPLAPSSKSTSGGTAALGCLVKDYFPEPVT</u>

<u>VSWNSGALTSGVHTFPAVLQSSGLYSLSSVVTVPSSSLGTQTYICNVNHKPSNTKVDKRVEPKSCDKTHTCPPCP</u>

<u>APEAAGAPSVFLFPPKPKDTLMISRTPEVTCVVVDVSHEDPEVKFNWYVDGVEVHNAKTKPREEQYNSTYRVVSV</u>

<u>LTVLHQDWLNGKEYKCAVSNKALPAPIEKTISKAKGQPREPQVYTLPPSRDELTKNQVSLTCLVKGFYPSDIAVE</u>

<u>WESNGQPENNYKTTPPVLDSDGSFFLYSKLTVDKSRWQQGNVFSCSVMHEALHNHYTQKSLSLSPG</u>

338H4 CHIMERIC HEAVY CHAIN VARIABLE HEAVY CHAIN AMINO ACID
SEQUENCE. COMPLIMENTARITY DETERMINING REGIONS ARE UNDERLINED
SEQ ID NO: 56
QSVEESGGRLVTPGTPLTLTCTVSGFSLS<u>SYAMS</u>WVRQAPGRGLEWIGI<u>IYASGSTYYASWAKG</u>RFTISKTSTTV

DLKITSPTTEDTATYFCAR<u>IYDGMDL</u>WGPGTLVTVSS

330F11 CHIMERIC LIGHT CHAIN FULL-LENGTH NUCLEOTIDE SEQUENCE
SEQ ID NO: 57
```
GATGTTGTGATGACCCAGACTCCAGCCTCCGTGGAGGCAGCTGTGGGAGGCACAGTCACCATCAAGTGCCAGGCC

AGTCAGAGCATTAATAACTACTTAGCCTGGTATCAGCAGAAACCAGGGCAGCCTCCCAAGCTCCTGATCTACAGG

GCATCCACTCTGGAATCTGGGGTCCCATCGCGGTTCAAAGGCAGTGGATCTGGGACACAGTTCACTCTCACCATC

AGCGACCTGGAGTGTGCCGATGCTGCCACTTACTATTGTCAAAGCTATAATGGTGTTGGTAGGACTGCTTTCGGC

GGAGGGACCGAGGTGGAGTTCAAACGTACGGTGGCTGCACCATCTGTCTTCATCTTCCCGCCATCTGATGAGCAG

TTGAAATCTGGAACTGCCTCTGTTGTGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCAGGACAGCAAGGACAGCACCTACAGC

CTCAGCAGCACCCTGACGCTGAGCAAAGCAGACTACGAGAAACACAAAGTCTACGCCTGCGAAGTCACCCATCAG

GGCCTGAGCTCGCCCGTCACAAAGAGCTTCAACAGGGGAGAGTGT
```

330F11 CHIMERIC LIGHT CHAIN VARIABLE LIGHT CHAIN NUCLEOTIDE
SEQUENCE
SEQ ID NO: 58
```
GATGTTGTGATGACCCAGACTCCAGCCTCCGTGGAGGCAGCTGTGGGAGGCACAGTCACCATCAAGTGCCAGGCC

AGTCAGAGCATTAATAACTACTTAGCCTGGTATCAGCAGAAACCAGGGCAGCCTCCCAAGCTCCTGATCTACAGG
```

```
GCATCCACTCTGGAATCTGGGGTCCCATCGCGGTTCAAAGGCAGTGGATCTGGGACACAGTTCACTCTCACCATC

AGCGACCTGGAGTGTGCCGATGCTGCCACTTACTATTGTCAAAGCTATAATGGTGTTGGTAGGACTGCTTTCGGC

GGAGGGACCGAGGTGGAGTTCAAA
```

330F11 CHIMERIC LIGHT CHAIN FULL-LENGTH AMINO ACID SEQUENCE.
HUMAN KAPPA CONSTANT DOMAIN IS UNDERLINED
SEQ ID NO: 59

DVVMTQTPASVEAAVGGTVTIKCQASQSINNYLAWYQQKPGQPPKLLIYRASTLESGVPSRFKGSGSGTQFTLTI

SDLECADAATYYCQSYNGVGRTAFGGGTEVEFK<u>RTVAAPSVFIFPPSDEQLKSGTASVVCLLNNFYPREAKVQWK</u>

<u>VDNALQSGNSQESVTEQDSKDSTYSLSSTLTLSKADYEKHKVYACEVTHQGLSSPVTKSFNRGEC</u>

330F11 CHIMERIC LIGHT CHAIN VARIABLE LIGHT CHAIN AMINO ACID
SEQUENCE. COMPIMENTARITY DETERMINING REGIONS ARE UNDERLINED
SEQ ID NO: 60

DVVMTQTPASVEAAVGGTVTIKC<u>QASQSINNYLA</u>WYQQKPGQPPKLLIY<u>RASTLES</u>GVPSRFKGSGSGTQFTLTI

SDLECADAATYYC<u>QSYNGVGRTA</u>FGGGTEVEFK

330F11 CHIMERIC HEAVY CHAIN FULL-LENGTH NUCLEOTIDE SEQUENCE
SEQ ID NO: 61

```
CAGTCGGTGGAGGAGTCCGGGGGTCGCCTGGTCACGCCTGGGACACCCCTGACACTCACCTGCACAGTCTCTGGA

TTCTCCCTCAATAACTACTGGATGAGCTGGGTCCGCCAGGCTCCAGGGGAGGGGCTGGAATGGATCGGAACCATT

AGTAGTGGTGCGTATACATGGTTCGCCACCTGGGCGACAGGCCGATTCACCATCTCCAAAACCTCGACCACGGTG

GATCTGAGCATCACCAGTCCGACAACCGAGGACACGGCCACCTATTTCTGTGCCAGATATTCTTCTACTACTGAT

TGGACCTACTTTAACATCTGGGGCCCGGGCACCCTGGTCACCGTCTCGAGCGCTAGCACCAAGGGCCCATCGGTC

TTCCCCCTGGCACCCTCCTCCAAGAGCACCTCTGGGGGCACAGCGGCCCTGGGCTGCCTGGTCAAGGACTACTTC

CCCGAACCGGTGACGGTGTCGTGGAACTCAGGCGCCCTGACCAGCGGCGTGCACACCTTCCCGGCTGTCCTACAG

TCCTCAGGACTCTACTCCCTCAGCAGCGTGGTGACCGTGCCCTCCAGCAGCTTGGGCACCCAGACCTACATCTGC

AACGTGAATCACAAGCCCAGCAACACCAAGGTGGACAAGAGAGTTGAGCCCAAATCTTGTGACAAAACTCACACA

TGCCCACCGTGCCCAGCACCTGAAGCCGCGGGGGCACCGTCAGTCTTCCTCTTCCCCCCAAAACCCAAGGACACC

CTCATGATCTCCCGGACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAGGAGTACAAGTGCGCGGTCTCCAAC

AAAGCCCTCCCAGCCCCCATCGAGAAAACCATCTCCAAAGCCAAAGGGCAGCCCCGAGAACCACAGGTGTACACC

CTGCCCCCATCCCGGGATGAGCTGACCAAGAACCAGGTCAGCCTGACCTGCCTGGTCAAAGGCTTCTATCCCAGC

GACATCGCCGTGGAGTGGGAGAGCAATGGGCAGCCGGAGAACAACTACAAGACCACGCCTCCCGTGCTGGACTCC

GACGGCTCCTTCTTCCTCTATAGCAAGCTCACCGTGGACAAGAGCAGGTGGCAGCAGGGGAACGTCTTCTCATGC

TCCGTGATGCATGAGGCTCTGCACAACCACTACACGCAGAAGAGCCTCTCCCTGTCTCCGGGT
```

330F11 CHIMERIC HEAVY CHAIN VARIABLE HEAVY CHAIN NUCLEOTIDE SEQUENCE
SEQ ID NO: 62

```
CAGTCGGTGGAGGAGTCCGGGGGTCGCCTGGTCACGCCTGGGACACCCCTGACACTCACCTGCACAGTCTCTGGA

TTCTCCCTCAATAACTACTGGATGAGCTGGGTCCGCCAGGCTCCAGGGGAGGGGCTGGAATGGATCGGAACCATT

AGTAGTGGTGCGTATACATGGTTCGCCACCTGGGCGACAGGCCGATTCACCATCTCCAAAACCTCGACCACGGTG

GATCTGAGCATCACCAGTCCGACAACCGAGGACACGGCCACCTATTTCTGTGCCAGATATTCTTCTACTACTGAT

TGGACCTACTTTAACATCTGGGGCCCGGGCACCCTGGTCACCGTCTCGAGC
```

330F11 CHIMERIC HEAVY CHAIN FULL-LENGTH AMINO ACID SEQUENCE.
HUMAN GAMMA-1 CONSTANT DOMAIN IS UNDERLINED
SEQ ID NO: 63

QSVEESGGRLVTPGTPLTLTCTVSGFSLNNYWMSWVRQAPGEGLEWIGTISSGAYTWFATWATGRFTISKTSTTV

DLSITSPTTEDTATYFCARYSSTTDWTYFNIWGPGTLVTVSS<u>ASTKGPSVFPLAPSSKSTSGGTAALGCLVKDYF</u>

<u>PEPVTVSWNSGALTSGVHTFPAVLQSSGLYSLSSVVTVPSSSLGTQTYICNVNHKPSNTKVDKRVEPKSCDKTHT</u>

-continued

CPPCPAPEAAGAPSVFLFPPKPKDTLMISRTPEVTCVVVDVSHEDPEVKFNWYVDGVEVHNAKTKPREEQYNSTY

RVVSVLTVLHQDWLNGKEYKCAVSNKALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSCSVMHEALHNHYTQKSLSLSPG

330F11 CHIMERIC HEAVY CHAIN VARIABLE HEAVY CHAIN AMINO ACID
SEQUENCE. COMPLIMENTARITY DETERMINING REGIONS ARE UNDERLINED
SEQ ID NO: 64
QSVEESGGRLVTPGTPLTLTCTVSGFSLN<u>NYWMS</u>WVRQAPGEGLEWIG<u>TISSGAYTWFATWATG</u>RFTISKTSTTV

DLSITSPTTEDTATYFCAR<u>YSSTTDWTYFNI</u>WGPGTLVTVSS

226E12 HUMANIZED LIGHT CHAIN FULL-LENGTH NUCLEOTIDE SEQUENCE
SEQ ID NO: 65
GACATCCAGATGACCCAGTCTCCATCCTCCCTGTCTGCATCTGTAGGAGACAGAGTCACCATCACTTGCCAGGCC

AGTCAGAGAATTTACAGCTACTTAGCCTGGTATCAGCAGAAACCAGGGAAAGTTCCTAAGCTCCTGATCTATAGG

GCATCCACTCTGGCATCTGGGGTCCCATCTCGGTTCAGTGGCAGTGGATCTGGGACAGATTTCACTCTCACCATC

AGCAGCCTGCAGCCTGAAGATGTTGCAACTTATTACTGTCAACAGGGTGCTAGTATGGTTGATGTTGAGAATATG

TTCGGCGGAGGGACCAAGGTGGAGATCAAACGTACGGTGGCTGCACCATCTGTCTTCATCTTCCCGCCATCTGAT

GAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCACC

TACAGCCTCAGCAGCACCCTGACGCTGAGCAAAGCAGACTACGAGAAACACAAAGTCTACGCCTGCGAAGTCACC

CATCAGGGCCTGAGCTCGCCCGTCACAAAGAGCTTCAACAGGGGAGAGTGT

226E12 HUMANIZED LIGHT CHAIN VARIABLE LIGHT CHAIN NUCLEOTIDE
SEQUENCE
SEQ ID NO: 66
GACATCCAGATGACCCAGTCTCCATCCTCCCTGTCTGCATCTGTAGGAGACAGAGTCACCATCACTTGCCAGGCC

AGTCAGAGAATTTACAGCTACTTAGCCTGGTATCAGCAGAAACCAGGGAAAGTTCCTAAGCTCCTGATCTATAGG

GCATCCACTCTGGCATCTGGGGTCCCATCTCGGTTCAGTGGCAGTGGATCTGGGACAGATTTCACTCTCACCATC

AGCAGCCTGCAGCCTGAAGATGTTGCAACTTATTACTGTCAACAGGGTGCTAGTATGGTTGATGTTGAGAATATG

TTCGGCGGAGGGACCAAGGTGGAGATCAAA

226E12 HUMANIZED LIGHT CHAIN FULL-LENGTH AMINO ACID SEQUENCE.
HUMAN KAPPA CONSTANT DOMAIN IS UNDERLINED
SEQ ID NO: 67
DIQMTQSPSSLSASVGDRVTITCQASQRIYSYLAWYQQKPGKVPKLLIYRASTLASGVPSRFSGSGSGTDFTLTI

SSLQPEDVATYYCQQGASMVDVENMFGGGTKVEIK<u>RTVAAPSVFIFPPSDEQLKSGTASVVCLLNNFYPREAKVQ</u>

<u>WKVDNALQSGNSQESVTEQDSKDSTYSLSSTLTLSKADYEKHKVYACEVTHQGLSSPVTKSFNRGEC</u>

226E12 HUMANIZED LIGHT CHAIN VARIABLE LIGHT CHAIN AMINO ACID
SEQUENCE. COMPIMENTARITY DETERMINING REGIONS ARE UNDERLINED
SEQ ID NO: 68
DIQMTQSPSSLSASVGDRVTITC<u>QASQRIYSYLA</u>WYQQKPGKVPKLLIY<u>RASTLAS</u>GVPSRFSGSGSGTDFTLTI

SSLQPEDVATYYC<u>QQGASMVDVENMF</u>GGGTKVEIK

226E12 HUMANIZED HEAVY CHAIN FULL-LENGTH NUCLEOTIDE SEQUENCE
SEQ ID NO: 69
GAGGTGCAGCTGTTGGAGTCTGGGGGAGGCTTGGTACAGCCTGGGGGGTCCCTGAGACTCTCCTGTGCAGCCTCT

GGATTCTCCCTCAGTAACTACTACATGAGCTGGGTCCGCCAGGCTCCAGGGAAGGGGCTGGAGTGGATCGGAGCC

ATTAATGCTGACAGTGATAATACATGGTACCCGAGCTGGGTGAAAGGCCGGTTCACCATCTCCAGAGACAATTCC

AAGAACACGCTGTATCTGCAAATGAACAGCCTGAGAGCCGAGGACACGGCCGTATATTACTGTGCGAGAAGTGTG

AGTAATAATTTCGCCGAATATAACATCTGGGGCCAGGGAACCCTGGTCACCGTCTCGAGCGCTAGCACCAAGGGC

CCATCGGTCTTCCCCCTGGCACCCTCCTCCAAGAGCACCTCTGGGGGCACAGCGGCCCTGGGCTGCCTGGTCAAG

GACTACTTCCCCGAACCGGTGACGGTGTCGTGGAACTCAGGCGCCCTGACCAGCGGCGTGCACACCTTCCCGGCT

GTCCTACAGTCCTCAGGACTCTACTCCCTCAGCAGCGTGGTGACCGTGCCCTCCAGCAGCTTGGGCACCCAGACC

TACATCTGCAACGTGAATCACAAGCCCAGCAACACCAAGGTGGACAAGAGAGTTGAGCCCAAATCTTGTGACAAA

-continued

ACTCACACATGCCCACCGTGCCCAGCACCTGAAGCCGCGGGGGCACCGTCAGTCTTCCTCTTCCCCCCAAAACCC

AAGGACACCCTCATGATCTCCCGGACCCCTGAGGTCACATGCGTGGTGGTGGACGTGAGCCACGAAGACCCTGAG

GTCAAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGCGCG

GTCTCCAACAAAGCCCTCCCAGCCCCCATCGAGAAAACCATCTCCAAAGCCAAAGGGCAGCCCCGAGAACCACAG

GTGTACACCCTGCCCCCATCCCGGGATGAGCTGACCAAGAACCAGGTCAGCCTGACCTGCCTGGTCAAAGGCTTC

TATCCCAGCGACATCGCCGTGGAGTGGGAGAGCAATGGGCAGCCGGAGAACAACTACAAGACCACGCCTCCCGTG

CTGGACTCCGACGGCTCCTTCTTCCTCTATAGCAAGCTCACCGTGGACAAGAGCAGGTGGCAGCAGGGGAACGTC

TTCTCATGCTCCGTGATGCATGAGGCTCTGCACAACCACTACACGCAGAAGAGCCTCTCCCTGTCTCCGGGT

226E12 HUMANIZED HEAVY CHAIN VARIABLE HEAVY CHAIN NUCLEOTIDE
SEQUENCE
                                                    SEQ ID NO: 70
GAGGTGCAGCTGTTGGAGTCTGGGGGAGGCTTGGTACAGCCTGGGGGGTCCCTGAGACTCTCCTGTGCAGCCTCT

GGATTCTCCCTCAGTAACTACTACATGAGCTGGGTCCGCCAGGCTCCAGGGAAGGGGCTGGAGTGGATCGGAGCC

ATTAATGCTGACAGTGATAATACATGGTACCCGAGCTGGGTGAAAGGCCGGTTCACCATCTCCAGAGACAATTCC

AAGAACACGCTGTATCTGCAAATGAACAGCCTGAGAGCCGAGGACACGGCCGTATATTACTGTGCGAGAAGTGTG

AGTAATAATTTCGCCGAATATAACATCTGGGGCCAGGGAACCCTGGTCACCGTCTCGAGC

226E12 HUMANIZED HEAVY CHAIN FULL-LENGTH AMINO ACID SEQUENCE.
HUMAN GAMMA-1 CONSTANT DOMAIN IS UNDERLINED
                                                    SEQ ID NO: 71
EVQLLESGGGLVQPGGSLRLSCAASGFSLSNYYMSWVRQAPGKGLEWIGAINADSDNTWYPSWVKGRFTISRDNS

KNTLYLQMNSLRAEDTAVYYCARSVSNNFAEYNIWGQGTLVTVSS<u>ASTKGPSVFPLAPSSKSTSGGTAALGCLVK</u>

<u>DYFPEPVTVSWNSGALTSGVHTFPAVLQSSGLYSLSSVVTVPSSSLGTQTYICNVNHKPSNTKVDKRVEPKSCDK</u>

<u>THTCPPCPAPEAAGAPSVFLFPPKPKDTLMISRTPEVTCVVVDVSHEDPEVKFNWYVDGVEVHNAKTKPREEQYN</u>

<u>STYRVVSVLTVLHQDWLNGKEYKCAVSNKALPAPIEKTISKAKGQPREPQVYTLPPSRDELTKNQVSLTCLVKGF</u>

<u>YPSDIAVEWESNGQPENNYKTTPPVLDSDGSFFLYSKLTVDKSRWQQGNVFSCSVMHEALHNHYTQKSLSLSPG</u>

226E12 HUMANIZED HEAVY CHAIN VARIABLE HEAVY CHAIN AMINO ACID
SEQUENCE. COMPLIMENTARITY DETERMINING REGIONS ARE UNDERLINED
                                                    SEQ ID NO: 72
EVQLLESGGGLVQPGGSLRLSCAASGFSLS<u>NYYMS</u>WVRQAPGKGLEWIG<u>AINADSDNTWYPSWVKG</u>RFTISRDNS

KNTLYLQMNSLRAEDTAVYYCAR<u>SVSNNFAEYNI</u>WGQGTLVTVSS

323H7 HUMANIZED LIGHT CHAIN FULL-LENGTH NUCLEOTIDE SEQUENCE
                                                    SEQ ID NO: 73
GACATCCAGATGACCCAGTCTCCATCCTCCCTGTCTGCATCTGTAGGAGACAGAGTCACCATCACTTGCCAGTCC

AGTCAGAGTGTTTATAACAACAACGACTTAGCCTGGTATCAGCAGAAACCAGGGAAAGTTCCTAAGCTCCTGATC

TATTATGCATCCACTCTGGCATCTGGGGTCCCATCTCGGTTCAGTGGCAGTGGATCTGGGACAGATTTCACTCTC

ACCATCAGCAGCCTGCAGCCTGAAGATGTTGCAACTTATTACTGTCAGGCGGTTATGATACGGATGGTCTTGAT

ACGTTTGCTTTCGGCGGAGGGACCAAGGTGGAGATCAAACGTACGGTGGCTGCACCATCTGTCTTCATCTTCCCG

CCATCTGATGAGCAGTTGAAATCTGGAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGAGAGTGTCACAGAGCAGGACAGCAAG

GACAGCACCTACAGCCTCAGCAGCACCCTGACGCTGAGCAAAGCAGACTACGAGAAACACAAAGTCTACGCCTGC

GAAGTCACCCATCAGGGCCTGAGCTCGCCCGTCACAAAGAGCTTCAACAGGGGAGAGTGT

323H7 HUMANIZED LIGHT CHAIN VARIABLE LIGHT CHAIN NUCLEOTIDE
SEQUENCE
                                                    SEQ ID NO: 74
GACATCCAGATGACCCAGTCTCCATCCTCCCTGTCTGCATCTGTAGGAGACAGAGTCACCATCACTTGCCAGTCC

AGTCAGAGTGTTTATAACAACAACGACTTAGCCTGGTATCAGCAGAAACCAGGGAAAGTTCCTAAGCTCCTGATC

-continued

TATTATGCATCCACTCTGGCATCTGGGGTCCCATCTCGGTTCAGTGGCAGTGGATCTGGGACAGATTTCACTCTC

ACCATCAGCAGCCTGCAGCCTGAAGATGTTGCAACTTATTACTGTGCAGGCGGTTATGATACGGATGGTCTTGAT

ACGTTTGCTTTCGGCGGAGGGACCAAGGTGGAGATCAAA

323H7 HUMANIZED LIGHT CHAIN FULL-LENGTH AMINO ACID SEQUENCE.
HUMAN KAPPA CONSTANT DOMAIN IS UNDERLINED
SEQ ID NO: 75
DIQMTQSPSSLSASVGDRVTITCQSSQSVYNNNDLAWYQQKPGKVPKLLIYYASTLASGVPSRFSGSGSGTDFTL

TISSLQPEDVATYYCAGGYDTDGLDTFAFGGGTKVEIK<u>RTVAAPSVFIFPPSDEQLKSGTASVVCLLNNFYPREA</u>

<u>KVQWKVDNALQSGNSQESVTEQDSKDSTYSLSSTLTLSKADYEKHKVYACEVTHQGLSSPVTKSFNRGEC</u>

323H7 HUMANIZED LIGHT CHAIN VARIABLE LIGHT CHAIN AMINO ACID
SEQUENCE. COMPIMENTARITY DETERMINING REGIONS ARE UNDERLINED
SEQ ID NO: 76
DIQMTQSPSSLSASVGDRVTITC<u>QSSQSVYNNNDLA</u>WYQQKPGKVPKLLIY<u>YASTLAS</u>GVPSRFSGSGSGTDFTL

TISSLQPEDVATYYCAGG<u>YDTDGLDTFAF</u>GGGTKVEIK

323H7 HUMANIZED HEAVY CHAIN FULL-LENGTH NUCLEOTIDE SEQUENCE
SEQ ID NO: 77
GAGGTGCAGCTGTTGGAGTCTGGGGGAGGCTTGGTACAGCCTGGGGGTCCCTGAGACTCTCCTGTGCAGCCTCT

GGATTCACCATCAGTCGCTACCACATGACTTGGGTCCGCCAGGCTCCAGGGAAGGGGCTGGAGTGGATCGGACAT

ATTTATGTTAATAATGATGACACAGACTACGCGAGCTCCGCGAAAGGCCGGTTCACCATCTCCAGAGACAATTCC

AAGAACACGCTGTATCTGCAAATGAACAGCCTGAGAGCCGAGGACACGGCCACCTATTTCTGTGCGAGATTGGAT

GTTGGTGGTGGTGGTGCTTATATTGGGGACATCTGGGGCCAGGGAACCCTGGTCACCGTCTCGAGCGCTAGCACC

AAGGGCCCATCGGTCTTCCCCCTGGCACCCTCCTCCAAGAGCACCTCTGGGGGCACAGCGGCCCTGGGCTGCCTG

GTCAAGGACTACTTCCCCGAACCGGTGACGGTGTCGTGGAACTCAGGCGCCCTGACCAGCGGCGTGCACACCTTC

CCGGCTGTCCTACAGTCCTCAGGACTCTACTCCCTCAGCAGCGTGGTGACCGTGCCCTCCAGCAGCTTGGGCACC

CAGACCTACATCTGCAACGTGAATCACAAGCCCAGCAACACCAAGGTGGACAAGAGAGTTGAGCCCAAATCTTGT

GACAAAACTCACACATGCCCACCGTGCCCAGCACCTGAAGCCGCGGGGGCACCGTCAGTCTTCCTCTTCCCCCCA

AAACCCAAGGACACCCTCATGATCTCCCGGACCCCTGAGGTCACATGCGTGGTGGTGGACGTGAGCCACGAAGAC

CCTGAGGTCAAGTTCAACTGGTACGTGGACGGCGTGGAGGTGCATAATGCCAAGACAAAGCCGCGGGAGGAGCAG

TACAACAGCACGTACCGTGTGGTCAGCGTCCTCACCGTCCTGCACCAGGACTGGCTGAATGGCAAGGAGTACAAG

TGCGCGGTCTCCAACAAAGCCCTCCCAGCCCCCATCGAGAAAACCATCTCCAAAGCCAAAGGGCAGCCCCGAGAA

CCACAGGTGTACACCCTGCCCCCATCCCGGGATGAGCTGACCAAGAACCAGGTCAGCCTGACCTGCCTGGTCAAA

GGCTTCTATCCCAGCGACATCGCCGTGGAGTGGGAGAGCAATGGGCAGCCGGAGAACAACTACAAGACCACGCCT

CCCGTGCTGGACTCCGACGGCTCCTTCTTCCTCTATAGCAAGCTCACCGTGGACAAGAGCAGGTGGCAGCAGGGG

AACGTCTTCTCATGCTCCGTGATGCATGAGGCTCTGCACAACCACTACACGCAGAAGAGCCTCTCCCTGTCTCCG

GGT

323H7 HUMANIZED HEAVY CHAIN VARIABLE HEAVY CHAIN NUCLEOTIDE
SEQUENCE
SEQ ID NO: 78
GAGGTGCAGCTGTTGGAGTCTGGGGGAGGCTTGGTACAGCCTGGGGGTCCCTGAGACTCTCCTGTGCAGCCTCT

GGATTCACCATCAGTCGCTACCACATGACTTGGGTCCGCCAGGCTCCAGGGAAGGGGCTGGAGTGGATCGGACAT

ATTTATGTTAATAATGATGACACAGACTACGCGAGCTCCGCGAAAGGCCGGTTCACCATCTCCAGAGACAATTCC

AAGAACACGCTGTATCTGCAAATGAACAGCCTGAGAGCCGAGGACACGGCCACCTATTTCTGTGCGAGATTGGAT

GTTGGTGGTGGTGGTGCTTATATTGGGGACATCTGGGGCCAGGGAACCCTGGTCACCGTCTCGAGC

323H7 HUMANIZED HEAVY CHAIN FULL-LENGTH AMINO ACID SEQUENCE.
HUMAN GAMMA-1 CONSTANT DOMAIN IS UNDERLINED
SEQ ID NO: 79
EVQLLESGGGLVQPGGSLRLSCAASGFTISRYHMTWVRQAPGKGLEWIGHIYVNNDDTDYASSAKGRFTISRDNS

KNTLYLQMNSLRAEDTATYFCARLDVGGGGAYIGDIWGQGTLVTVSS<u>ASTKGPSVFPLAPSSKSTSGGTAALGCL</u>

-continued

<u>VKDYFPEPVTVSWNSGALTSGVHTFPAVLQSSGLYSLSSVVTVPSSSLGTQTYICNVNHKPSNTKVDKRVEPKSC</u>

<u>DKTHTCPPCPAPEAAGAPSVFLFPPKPKDTLMISRTPEVTCVVVDVSHEDPEVKFNWYVDGVEVHNAKTKPREEQ</u>

<u>YNSTYRVVSVLTVLHQDWLNGKEYKCAVSNKALPAPIEKTISKAKGQPREPQVYTLPPSRDELTKNQVSLTCLVK</u>

<u>GFYPSDIAVEWESNGQPENNYKTTPPVLDSDGSFFLYSKLTVDKSRWQQGNVFSCSVMHEALHNHYTQKSLSLSP</u>

<u>G</u>

323H7 HUMANIZED HEAVY CHAIN VARIABLE HEAVY CHAIN AMINO ACID
SEQUENCE. COMPLIMENTARITY DETERMINING REGIONS ARE UNDERLINED
SEQ ID NO: 80
EVQLLESGGGLVQPGGSLRLSCAASGFTIS<u>RYHMT</u>WVRQAPGKGLEWIG<u>HIYVNNDDTDYASSAKG</u>RFTISRDNS

KNTLYLQMNSLRAEDTATYFCAR<u>LDVGGGGAYIGDI</u>WGQGTLVTVSS

324C7 HUMANIZED LIGHT CHAIN FULL-LENGTH NUCLEOTIDE SEQUENCE
SEQ ID NO: 81
GACATCCAGATGACCCAGTCTCCATCTTCCGTGTCTGCATCTGTAGGAGACAGAGTCACCATCACTTGTCAGGCC

AGTCAGAACATTGGTAGTGATTTAGCCTGGTATCAGCAGAAACCAGGGAAAGCCCCTAAGCTCCTGATCTATACT

ACATCCAATCTGGCATCTGGGGTCCCATCAAGGTTCAGCGGCAGTGGATCTGGGACAGATTTCACTCTCACCATC

AGCAGCCTGCAGCCTGAAGATTTTGCAACTTACTATTGTCAAGGCGGTTATTTTAGTGGTCGTAATATTTATGGG

AATGCTTTCGGCGGAGGGACCAAGGTGGAGATCAAACGTACGGTGGCTGCACCATCTGTCTTCATCTTCCCGCCA

TCTGATGAGCAGTTGAAATCTGGAACTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAGTGTCACAGAGCAGGACAGCAAGGAC

AGCACCTACAGCCTCAGCAGCACCCTGACGCTGAGCAAAGCAGACTACGAGAAACACAAAGTCTACGCCTGCGAA

GTCACCCATCAGGGCCTGAGCTCGCCCGTCACAAAGAGCTTCAACAGGGGAGAGTGT

324C7 HUMANIZED LIGHT CHAIN VARIABLE LIGHT CHAIN NUCLEOTIDE
SEQUENCE
SEQ ID NO: 82
GACATCCAGATGACCCAGTCTCCATCTTCCGTGTCTGCATCTGTAGGAGACAGAGTCACCATCACTTGTCAGGCC

AGTCAGAACATTGGTAGTGATTTAGCCTGGTATCAGCAGAAACCAGGGAAAGCCCCTAAGCTCCTGATCTATACT

ACATCCAATCTGGCATCTGGGGTCCCATCAAGGTTCAGCGGCAGTGGATCTGGGACAGATTTCACTCTCACCATC

AGCAGCCTGCAGCCTGAAGATTTTGCAACTTACTATTGTCAAGGCGGTTATTTTAGTGGTCGTAATATTTATGGG

AATGCTTTCGGCGGAGGGACCAAGGTGGAGATCAAA

324C7 HUMANIZED LIGHT CHAIN FULL-LENGTH AMINO ACID SEQUENCE.
HUMAN KAPPA CONSTANT DOMAIN IS UNDERLINED
SEQ ID NO: 83
DIQMTQSPSSVSASVGDRVTITCQASQNIGSDLAWYQQKPGKAPKLLIYTTSNLASGVPSRFSGSGSGTDFTLTI

SSLQPEDFATYYCQGGYFSGRNIYGNAFGGGTKVEIK<u>RTVAAPSVFIFPPSDEQLKSGTASVVCLLNNFYPREAK</u>

<u>VQWKVDNALQSGNSQESVTEQDSKDSTYSLSSTLTLSKADYEKHKVYACEVTHQGLSSPVTKSFNRGEC</u>

324C7 HUMANIZED LIGHT CHAIN VARIABLE LIGHT CHAIN AMINO ACID
SEQUENCE. COMPLIMENTARITY DETERMINING REGIONS ARE UNDERLINED
SEQ ID NO: 84
DIQMTQSPSSVSASVGDRVTITC<u>QASQNIGSDLA</u>WYQQKPGKAPKLLIY<u>TTSNLAS</u>GVPSRFSGSGSGTDFTLTI

SSLQPEDFATYYC<u>QGGYFSGRNIYGNA</u>FGGGTKVEIK

324C7 HUMANIZED HEAVY CHAIN FULL-LENGTH NUCLEOTIDE SEQUENCE -
VARIANT 1
SEQ ID NO: 85
GAGGTGCAGCTGGTGGAGTCTGGGGGAGGCTTGGTCCAGCCTGGGGGGTCCCTGAGACTCTCCTGTGCAGCCTCT

GGATTCTCCCTCAGTGGCGCTGGAGTGAGCTGGGTCCGCCAGGCTCCAGGGAAGGGGCTGGAGTGGATCGGGTAC

ATTGATAGTGGTGCTACCACATACTACGCGAGCAGTGCAAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGATACTAC

GGCATGGACCCCTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

-continued

```
CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTG

AATCACAAGCCCAGCAACACCAAGGTGGACAAGAGAGTTGAGCCCAAATCTTGTGACAAAACTCACACATGCCCA

CCGTGCCCAGCACCTGAAGCCGCGGGGGCACCGTCAGTCTTCCTCTTCCCCCCAAAACCCAAGGACACCCTCATG

ATCTCCCGGACCCCTGAGGTCACATGCGTGGTGGTGGACGTGAGCCACGAAGACCCTGAGGTCAAGTTCAACTGG

TACGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGGC

TCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT
```

324C7 HUMANIZED HEAVY CHAIN VARIABLE HEAVY CHAIN NUCLEOTIDE
SEQUENCE - VARIANT 1

SEQ ID NO: 86

```
GAGGTGCAGCTGGTGGAGTCTGGGGGAGGCTTGGTCCAGCCTGGGGGGTCCCTGAGACTCTCCTGTGCAGCCTCT

GGATTCTCCCTCAGTGGCGCTGGAGTGAGCTGGGTCCGCCAGGCTCCAGGGAAGGGGCTGGAGTGGATCGGGTAC

ATTGATAGTGGTGCTACCACATACTACGCGAGCAGTGCAAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGATACTAC

GGCATGGACCCCTGGGGCCAGGGAACCCTGGTCACCGTCTCGAGC
```

324C7 HUMANIZED HEAVY CHAIN FULL-LENGTH AMINO ACID SEQUENCE -
VARIANT 1. HUMAN GAMMA-1 CONSTANT DOMAIN IS UNDERLINED

SEQ ID NO: 87

EVQLVESGGGLVQPGGSLRLSCAASGFSLSGAGVSWVRQAPGKGLEWIGYIDSGATTYYASSAKGRFTISRDNSK

NTLYLQMNSLRAEDTAVYYCARGYYGMDPWGQGTLVTVSS<u>ASTKGPSVFPLAPSSKSTSGGTAALGCLVKDYFPE</u>

<u>PVTVSWNSGALTSGVHTFPAVLQSSGLYSLSSVVTVPSSSLGTQTYICNVNHKPSNTKVDKRVEPKSCDKTHTCP</u>

<u>PCPAPEAAGAPSVFLFPPKPKDTLMISRTPEVTCVVVDVSHEDPEVKFNWYVDGVEVHNAKTKPREEQYNSTYRV</u>

<u>VSVLTVLHQDWLNGKEYKCAVSNKALPAPIEKTISKAKGQPREPQVYTLPPSRDELTKNQVSLTCLVKGFYPSDI</u>

<u>AVEWESNGQPENNYKTTPPVLDSDGSFFLYSKLTVDKSRWQQGNVFSCSVMHEALHNHYTQKSLSLSPG</u>

324C7 HUMANIZED HEAVY CHAIN VARIABLE HEAVY CHAIN AMINO ACID
SEQUENCE - VARIANT 1. COMPLIMENTARITY DETERMINING REGIONS
ARE UNDERLINED

SEQ ID NO: 88

EVQLVESGGGLVQPGGSLRLSCAASGFSLS<u>GAGVS</u>WVRQAPGKGLEWIGY<u>IDSGATTYYASSAK</u>GRFTISRDNSK

NTLYLQMNSLRAEDTAVYYCAR<u>GYYGMDP</u>WGQGTLVTVSS

324C7 HUMANIZED HEAVY CHAIN FULL-LENGTH NUCLEOTIDE SEQUENCE -
VARIANT 2

SEQ ID NO: 89

```
GAGGTGCAGCTGGTGGAGTCTGGGGGAGGCTTGGTCCAGCCTGGGGGGTCCCTGAGACTCTCCTGTACAGCCTCT

GGATTCTCCCTCAGTGGCGCTGGAGTGAGCTGGGTCCGCCAGGCTCCAGGGAAGGGGCTGGAGTGGATCGGGTAC

ATTGATAGTGGTGCTACCACATACTACGCGAGCAGTGCAAAAGGCAGATTCACCATCTCCAAAGACAATGCCAAG

AACACGGTGGATCTTCAAATGAACAGCCTGAGAGCCGAGGACACGGCTGTGTATTACTGTGCGAGAGGATACTAC

GGCATGGACCCCTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTG

AATCACAAGCCCAGCAACACCAAGGTGGACAAGAGAGTTGAGCCCAAATCTTGTGACAAAACTCACACATGCCCA
```

-continued

CCGTGCCCAGCACCTGAAGCCGCGGGGGCACCGTCAGTCTTCCTCTTCCCCCCAAAACCCAAGGACACCCTCATG

ATCTCCCGGACCCCTGAGGTCACATGCGTGGTGGTGGACGTGAGCCACGAAGACCCTGAGGTCAAGTTCAACTGG

TACGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGGC

TCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

324C7 HUMANIZED HEAVY CHAIN VARIABLE HEAVY CHAIN NUCLEOTIDE
SEQUENCE - VARIANT 2
                                                          SEQ ID NO: 90
GAGGTGCAGCTGGTGGAGTCTGGGGGAGGCTTGGTCCAGCCTGGGGGGTCCCTGAGACTCTCCTGTACAGCCTCT

GGATTCTCCCTCAGTGGCGCTGGAGTGAGCTGGGTCCGCCAGGCTCCAGGGAAGGGGCTGGAGTGGATCGGGTAC

ATTGATAGTGGTGCTACCACATACTACGCGAGCAGTGCAAAAGGCAGATTCACCATCTCCAAAGACAATGCCAAG

AACACGGTGGATCTTCAAATGAACAGCCTGAGAGCCGAGGACACGGCTGTGTATTACTGTGCGAGAGGATACTAC

GGCATGGACCCCTGGGGCCAGGGAACCCTGGTCACCGTCTCGAGC

324C7 HUMANIZED HEAVY CHAIN FULL-LENGTH AMINO ACID SEQUENCE -
VARIANT 2. HUMAN GAMMA-1 CONSTANT DOMAIN IS UNDERLINED
                                                          SEQ ID NO: 91
EVQLVESGGGLVQPGGSLRLSCTASGFSLSGAGVSWVRQAPGKGLEWIGYIDSGATTYYASSAKGRFTISKDNAK

NTVDLQMNSLRAEDTAVYYCARGYYGMDPWGQGTLVTVSS<u>ASTKGPSVFPLAPSSKSTSGGTAALGCLVKDYFPE</u>

<u>PVTVSWNSGALTSGVHTFPAVLQSSGLYSLSSVVTVPSSSLGTQTYICNVNHKPSNTKVDKRVEPKSCDKTHTCP</u>

<u>PCPAPEAAGAPSVFLFPPKPKDTLMISRTPEVTCVVVDVSHEDPEVKFNWYVDGVEVHNAKTKPREEQYNSTYRV</u>

<u>VSVLTVLHQDWLNGKEYKCAVSNKALPAPIEKTISKAKGQPREPQVYTLPPSRDELTKNQVSLTCLVKGFYPSDI</u>

<u>AVEWESNGQPENNYKTTPPVLDSDGSFFLYSKLTVDKSRWQQGNVFSCSVMHEALHNHYTQKSLSLSPG</u>

324C7 HUMANIZED HEAVY CHAIN VARIABLE HEAVY CHAIN AMINO ACID
SEQUENCE - VARIANT 2. COMPLIMENTARITY DETERMINING REGIONS
ARE UNDERLINED
                                                          SEQ ID NO: 92
EVQLVESGGGLVQPGGSLRLSCTASGFSLS<u>GAGVS</u>WVRQAPGKGLEWIG<u>YIDSGATTYYASSAK</u>GRFTISKDNAK

NTVDLQMNSLRAEDTAVYYCAR<u>GYYGMDP</u>WGQGTLVTVSS

323D10 HUMANIZED LIGHT CHAIN FULL-LENGTH NUCLEOTIDE SEQUENCE
                                                          SEQ ID NO: 93
GCCATCGATTTGACCCAGTCTCCTTCCACCCTGTCTGCATCTGTAGGAGGCACAATCACCATCAATTGCCAAGCC

AGTGAGAGCATTAGCAGTTGGTTAGCCTGGTATCAGCAGAAACCAGGGAAAGCCCCTAAGCTCCTGATCTATGAA

ACATCCAAACTGGCATCTGGGGTCCCATCAAGGTTCAGCGGCAGTGGATCTGGGACAGAGTTCACTCTCACCATC

AGCAGCCTGCAGCCTGATGATTTTGCAACTTATTACTGCCAAAGTTATTATCGTATTAATAATATTGGTTACGAT

AATGCTTTCGGCGGAGGGACCAAGGTGGAGATCAAACGTACGGTGGCTGCACCATCTGTCTTCATCTTCCCGCCA

TCTGATGAGCAGTTGAAATCTGGAACTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAGTGTCACAGAGCAGGACAGCAAGGAC

AGCACCTACAGCCTCAGCAGCACCCTGACGCTGAGCAAAGCAGACTACGAGAAACACAAAGTCTACGCCTGCGAA

GTCACCCATCAGGGCCTGAGCTCGCCCGTCACAAAGAGCTTCAACAGGGGAGAGTGT

323D10 HUMANIZED LIGHT CHAIN VARIABLE LIGHT CHAIN NUCLEOTIDE
SEQUENCE
                                                          SEQ ID NO: 94
GCCATCGATTTGACCCAGTCTCCTTCCACCCTGTCTGCATCTGTAGGAGGCACAATCACCATCAATTGCCAAGCC

AGTGAGAGCATTAGCAGTTGGTTAGCCTGGTATCAGCAGAAACCAGGGAAAGCCCCTAAGCTCCTGATCTATGAA

-continued

```
ACATCCAAACTGGCATCTGGGGTCCCATCAAGGTTCAGCGGCAGTGGATCTGGGACAGAGTTCACTCTCACCATC

AGCAGCCTGCAGCCTGATGATTTTGCAACTTATTACTGCCAAAGTTATTATCGTATTAATAATATTGGTTACGAT

AATGCTTTCGGCGGAGGGACCAAGGTGGAGATCAAA
```

323D10 HUMANIZED LIGHT CHAIN FULL-LENGTH AMINO ACID SEQUENCE.
HUMAN KAPPA CONSTANT DOMAIN IS UNDERLINED
                                                    SEQ ID NO: 95
AIDLTQSPSTLSASVGGTITINCQASESISSWLAWYQQKPGKAPKLLIYETSKLASGVPSRFSGSGSGTEFTLTI

SSLQPDDFATYYCQSYYRINNIGYDNAFGGGTKVEIK<u>RTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSFNRGEC</u>

323D10 HUMANIZED LIGHT CHAIN VARIABLE LIGHT CHAIN AMINO ACID
SEQUENCE. COMPIMENTARITY DETERMINING REGIONS ARE UNDERLINED
                                                    SEQ ID NO: 96
AIDLTQSPSTLSASVGGTITINC<u>QASESISSWLA</u>WYQQKPGKAPKLLIY<u>ETSKLAS</u>GVPSRFSGSGSGTEFTLTI

SSLQPDDFATYYC<u>QSYYRINNIGYDNA</u>FGGGTKVEIK

323D10 HUMANIZED HEAVY CHAIN FULL-LENGTH NUCLEOTIDE SEQUENCE
                                                    SEQ ID NO: 97
```
GAGGTGCAGCTGGTGGAGTCTGGGGGAGGCTTGGTCCAGCCTGGGGGGTCCCTGAGACTCTCCTGTACCGCCTCT

GGATTCTCCCTCAGTAGGAATGCAATGAACTGGGTCCGCCAGGCTCCAGGGAAGGGGCTGGAGTACATCGGATAC

ATTAGCACTAGTGGTACCACATTCTACGCGAACAGCGTGAAAGGCAGATTCACCATCTCCAAAGACAATACCAAG

AACACGGTGGATCTTCAAATGAACAGCCTGAGAGCCGAGGACACGGCTGTGTATTACTGTGCGAGAGACTATAAC

TACGCCATGGACATCTGGGGCCAGGGAACCCTGGTCACCGTCTCGAGCGCTAGCACCAAGGGCCCATCGGTCTTC

CCCCTGGCACCCTCCTCCAAGAGCACCTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGCACACCTTCCCGGCTGTCCTACAGTCC

TCAGGACTCTACTCCCTCAGCAGCGTGGTGACCGTGCCCTCCAGCAGCTTGGGCACCCAGACCTACATCTGCAAC

GTGAATCACAAGCCCAGCAACACCAAGGTGGACAAGAGAGTTGAGCCCAAATCTTGTGACAAAACTCACACATGC

CCACCGTGCCCAGCACCTGAAGCCGCGGGGGCACCGTCAGTCTTCCTCTTCCCCCCAAAACCCAAGGACACCCTC

ATGATCTCCCGGACCCCTGAGGTCACATGCGTGGTGGTGGACGTGAGCCACGAAGACCCTGAGGTCAAGTTCAAC

TGGTACGTGGACGGCGTGGAGGTGCATAATGCCAAGACAAAGCCGCGGGAGGAGCAGTACAACAGCACGTACCGT

GTGGTCAGCGTCCTCACCGTCCTGCACCAGGACTGGCTGAATGGCAAGGAGTACAAGTGCGCGGTCTCCAACAAA

GCCCTCCCAGCCCCCATCGAGAAAACCATCTCCAAAGCCAAAGGGCAGCCCCGAGAACCACAGGTGTACACCCTG

CCCCCATCCCGGGATGAGCTGACCAAGAACCAGGTCAGCCTGACCTGCCTGGTCAAAGGCTTCTATCCCAGCGAC

ATCGCCGTGGAGTGGGAGAGCAATGGGCAGCCGGAGAACAACTACAAGACCACGCCTCCCGTGCTGGACTCCGAC

GGCTCCTTCTTCCTCTATAGCAAGCTCACCGTGGACAAGAGCAGGTGGCAGCAGGGGAACGTCTTCTCATGCTCC

GTGATGCATGAGGCTCTGCACAACCACTACACGCAGAAGAGCCTCTCCCTGTCTCCGGGT
```

323D10 HUMANIZED HEAVY CHAIN VARIABLE HEAVY CHAIN NUCLEOTIDE
SEQUENCE
                                                    SEQ ID NO: 98
```
GAGGTGCAGCTGGTGGAGTCTGGGGGAGGCTTGGTCCAGCCTGGGGGGTCCCTGAGACTCTCCTGTACCGCCTCT

GGATTCTCCCTCAGTAGGAATGCAATGAACTGGGTCCGCCAGGCTCCAGGGAAGGGGCTGGAGTACATCGGATAC

ATTAGCACTAGTGGTACCACATTCTACGCGAACAGCGTGAAAGGCAGATTCACCATCTCCAAAGACAATACCAAG

AACACGGTGGATCTTCAAATGAACAGCCTGAGAGCCGAGGACACGGCTGTGTATTACTGTGCGAGAGACTATAAC

TACGCCATGGACATCTGGGGCCAGGGAACCCTGGTCACCGTCTCGAGC
```

323D10 HUMANIZED HEAVY CHAIN FULL-LENGTH AMINO ACID SEQUENCE.
HUMAN GAMMA-1 CONSTANT DOMAIN IS UNDERLINED
                                                    SEQ ID NO: 99
EVQLVESGGGLVQPGGSLRLSCTASGFSLSRNAMNWVRQAPGKGLEYIGYISTSGTTFYANSVKGRFTISKDNTK

NTVDLQMNSLRAEDTAVYYCARDYNYAMDIWGQGTLVTVSS<u>ASTKGPSVFPLAPSSKSTSGGTAALGCLVKDYFP

EPVTVSWNSGALTSGVHTFPAVLQSSGLYSLSSVVTVPSSSLGTQTYICNVNHKPSNTKVDKRVEPKSCDKTHTC

PPCPAPEAAGAPSVFLFPPKPKDTLMISRTPEVTCVVVDVSHEDPEVKFNWYVDGVEVHNAKTKPREEQYNSTYR

VVSVLTVLHQDWLNGKEYKCAVSNKALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCSVMHEALHNHYTQKSLSLSPG

323D10 HUMANIZED HEAVY CHAIN VARIABLE HEAVY CHAIN AMINO ACID
SEQUENCE. COMPLIMENTARITY DETERMINING REGIONS ARE UNDERLINED

SEQ ID NO: 100

EVQLVESGGGLVQPGGSLRLSCTASGFSLS<u>RNAMN</u>WVRQAPGKGLEYIG<u>YISTSGTTFYANS</u>VKGRFTISKDNTK

NTVDLQMNSLRAEDTAVYYCAR<u>DYNYAMDI</u>WGQGTLVTVSS

324E2 HUMANIZED LIGHT CHAIN FULL-LENGTH NUCLEOTIDE SEQUENCE

SEQ ID NO: 101

GACATCCAGATGACCCAGTCTCCATCCTCCCTGTCTGCATCTGTAGGAGACAGAGTCACCATCACTTGCCAGTCC

AGTCAGAGTGTTAACAACAACGACTTAGCCTGGTATCAGCAGAAACCAGGGAAAGCCCCTAAGCGCCTGATCTAT

TGGGCATCCAAACTGGCATCTGGGGTCCCATCAAGGTTCAGCGGCAGTGGATCTGGGACAGAATTCACTCTCACA

ATCAGCAACCTGCAGCCTGAAGATTTTGCAACTTATTACTGTGCAGGCGGTTATAGTGGTAATATTTATGGTTTC

GGCGGAGGGACCAAGGTGGAGATCAAACGTACGGTGGCTGCACCATCTGTCTTCATCTTCCCGCCATCTGATGAG

CAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTACGCCTGCGAAGTCACCCAT

CAGGGGCCTGAGCTCGCCCGTCACAAAGAGCTTCAACAGGGGAGAGTGT

324E2 HUMANIZED LIGHT CHAIN VARIABLE LIGHT CHAIN NUCLEOTIDE
SEQUENCE

SEQ ID NO: 102

GACATCCAGATGACCCAGTCTCCATCCTCCCTGTCTGCATCTGTAGGAGACAGAGTCACCATCACTTGCCAGTCC

AGTCAGAGTGTTAACAACAACGACTTAGCCTGGTATCAGCAGAAACCAGGGAAAGCCCCTAAGCGCCTGATCTAT

TGGGCATCCAAACTGGCATCTGGGGTCCCATCAAGGTTCAGCGGCAGTGGATCTGGGACAGAATTCACTCTCACA

ATCAGCAACCTGCAGCCTGAAGATTTTGCAACTTATTACTGTGCAGGCGGTTATAGTGGTAATATTTATGGTTTC

GGCGGAGGGACCAAGGTGGAGATCAAA

324E2 HUMANIZED LIGHT CHAIN FULL-LENGTH AMINO ACID SEQUENCE.
HUMAN KAPPA CONSTANT DOMAIN IS UNDERLINED

SEQ ID NO: 103

DIQMTQSPSSLSASVGDRVTITCQSSQSVNNNDLAWYQQKPGKAPKRLIYWASKLASGVPSRFSGSGSGTEFTLT

ISNLQPEDFATYYCAGGYSGNIYGFGGGTKVEIK<u>RTVAAPSVFIFPPSDEQLKSGTASVVCLLNNFYPREAKVQW</u>

<u>KVDNALQSGNSQESVTEQDSKDSTYSLSSTLTLSKADYEKHKVYACEVTHQGLSSPVTKSFNRGEC</u>

324E2 HUMANIZED LIGHT CHAIN VARIABLE LIGHT CHAIN AMINO ACID
SEQUENCE. COMPIMENTARITY DETERMINING REGIONS ARE UNDERLINED

SEQ ID NO: 104

DIQMTQSPSSLSASVGDRVTITC<u>QSSQSVNNNDLA</u>WYQQKPGKAPKRLIY<u>WASKLAS</u>GVPSRFSGSGSGTEFTLT

ISNLQPEDFATYYC<u>AGGYSGNIYG</u>FGGGTKVE1K

324E2 HUMANIZED HEAVY CHAIN FULL-LENGTH NUCLEOTIDE SEQUENCE

SEQ ID NO: 105

CAGTCGGTGGAGGAGTCTGGGGGAGGCTTGGTCCAGCCTGGGGGGTCCCTGAGACTCTCCTGTACCGCCTCTGGA

TTCTCCCTCAGTAACAATGCAATAACCTGGGTCCGCCAGGCTCCAGGGAAGGGGCTGGAGTACATCGGAATCATT

AGTAGTAGTGGTACCACATACTACGCGAGCTCCGCGAAAGGCAGATTCACCATCTCCAAAGACACCTCCAAGAAC

ACGGTGGATCTTCAAATGAACAGCCTGAGAGCCGAGGACACGGCTGTGTATTACTGTGCGGGAGCATTTAGCGTC

TGGGGCCAGGGAACCCTGGTCACCGTCTCGAGCGCTAGCACCAAGGGCCCATCGGTCTTCCCCCTGGCACCCTCC

TCCAAGAGCACCTCTGGGGGCACAGCGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGTCCTACAGTCCTCAGGACTCTACTCC

CTCAGCAGCGTGGTGACCGTGCCCTCCAGCAGCTTGGGCACCCAGACCTACATCTGCAACGTGAATCACAAGCCC

AGCAACACCAAGGTGGACAAGAGAGTTGAGCCCAAATCTTGTGACAAAACTCACACATGCCCACCGTGCCCAGCA

CCTGAAGCCGCGGGGGCACCGTCAGTCTTCCTCTTCCCCCCAAAACCCAAGGACACCCTCATGATCTCCCGGACC

CCTGAGGTCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGTGTGGTCAGCGTCCTC

ACCGTCCTGCACCAGGACTGGCTGAATGGCAAGGAGTACAAGTGCGCGGTCTCCAACAAAGCCCTCCCAGCCCCC

ATCGAGAAAACCATCTCCAAAGCCAAAGGGCAGCCCCGAGAACCACAGGTGTACACCCTGCCCCCATCCCGGGAT

GAGCTGACCAAGAACCAGGTCAGCCTGACCTGCCTGGTCAAAGGCTTCTATCCCAGCGACATCGCCGTGGAGTGG

GAGAGCAATGGGCAGCCGGAGAACAACTACAAGACCACGCCTCCCGTGCTGGACTCCGACGGCTCCTTCTTCCTC

TATAGCAAGCTCACCGTGGACAAGAGCAGGTGGCAGCAGGGGAACGTCTTCTCATGCTCCGTGATGCATGAGGCT

CTGCACAACCACTACACGCAGAAGAGCCTCTCCCTGTCTCCGGGT

324E2 HUMANIZED HEAVY CHAIN VARIABLE HEAVY CHAIN NUCLEOTIDE
SEQUENCE
                                                         SEQ ID NO: 106
CAGTCGGTGGAGGAGTCTGGGGGAGGCTTGGTCCAGCCTGGGGGGTCCCTGAGACTCTCCTGTACCGCCTCTGGA

TTCTCCCTCAGTAACAATGCAATAACCTGGGTCCGCCAGGCTCCAGGGAAGGGGCTGGAGTACATCGGAATCATT

AGTAGTAGTGGTACCACATACTACGCGAGCTCCGCGAAAGGCAGATTCACCATCTCCAAAGACACCTCCAAGAAC

ACGGTGGATCTTCAAATGAACAGCCTGAGAGCCGAGGACACGGCTGTGTATTACTGTGCGGGAGCATTTAGCGTC

TGGGGCCAGGGAACCCTGGTCACCGTCTCGAGC

324E2 HUMANIZED HEAVY CHAIN FULL-LENGTH AMINO ACID SEQUENCE.
HUMAN GAMMA-1 CONSTANT DOMAIN IS UNDERLINED
                                                         SEQ ID NO: 107
QSVEESGGGLVQPGGSLRLSCTASGFSLSNNAITWVRQAPGKGLEYIGIISSSGTTYYASSAKGRFTISKDTSKN

TVDLQMNSLRAEDTAVYYCAGAFSVWGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKVDKRVEPKSCDKTHTCPPCPA

PEAAGAPSVFLFPPKPKDTLMISRTPEVTCVVVDVSHEDPEVKFNWYVDGVEVHNAKTKPREEQYNSTYRVVSVL

TVLHQDWLNGKEYKCAVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSPG

324E2 HUMANIZED HEAVY CHAIN VARIABLE HEAVY CHAIN AMINO ACID
SEQUENCE. COMPLIMENTARITY DETERMINING REGIONS ARE UNDERLINED
                                                         SEQ ID NO: 108
QSVEESGGGLVQPGGSLRLSCTASGFSLSNNAITWVRQAPGKGLEYIGIISSSGTTYYASSAKGRFTISKDTSKN

TVDLQMNSLRAEDTAVYYCAGAFSVWGQGTLVTVSS

324C6 HUMANIZED LIGHT CHAIN FULL-LENGTH NUCLEOTIDE SEQUENCE
                                                         SEQ ID NO: 109
GACATCCAGATGACCCAGTCTCCTTCCACCCTGTCTGCATCTGTAGGAGACAGAGTCACCATCACTTGCCAGGCC

AGTCAGAGCATTGATAGTTGGTTATCCTGGTATCAGCAGAAACCAGGGAAAGCCCCTAAGCTCCTGATCTATCAG

GCATCCACTCTGGCATCTGGGGTCCCATCAAGGTTCAGCGGCAGTGGATCTGGGACAGAGTTCACTCTCACCATC

AGCAGCCTGCAGCCTGATGATTTTGCAACTTATTACTGCCAATCTGCTTATGGTGTTAGTGGTACTAGTAGTTAT

TTATATACTTTCGGCGGAGGGACCAAGGTGGAGATCAAACGTACGGTGGCTGCACCATCTGTCTTCATCTTCCCG

CCATCTGATGAGCAGTTGAAATCTGGAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGAGAGTGTCACAGAGCAGGACAGCAAG

GACAGCACCTACAGCCTCAGCAGCACCCTGACGCTGAGCAAAGCAGACTACGAGAAACACAAAGTCTACGCCTGC

GAAGTCACCCATCAGGGCCTGAGCTCGCCCGTCACAAAGAGCTTCAACAGGGGAGAGTGT

324C6 HUMANIZED LIGHT CHAIN VARIABLE LIGHT CHAIN NUCLEOTIDE
SEQUENCE
SEQ ID NO: 110
GACATCCAGATGACCCAGTCTCCTTCCACCCTGTCTGCATCTGTAGGAGACAGAGTCACCATCACTTGCCAGGCC

AGTCAGAGCATTGATAGTTGGTTATCCTGGTATCAGCAGAAACCAGGGAAAGCCCCTAAGCTCCTGATCTATCAG

GCATCCACTCTGGCATCTGGGGTCCCATCAAGGTTCAGCGGCAGTGGATCTGGGACAGAGTTCACTCTCACCATC

AGCAGCCTGCAGCCTGATGATTTTGCAACTTATTACTGCCAATCTGCTTATGGTGTTAGTGGTACTAGTAGTTAT

TTATATACTTTCGGCGGAGGGACCAAGGTGGAGATCAAA

324C6 HUMANIZED LIGHT CHAIN FULL-LENGTH AMINO ACID SEQUENCE.
HUMAN KAPPA CONSTANT DOMAIN IS UNDERLINED
SEQ ID NO: 111
DIQMTQSPSTLSASVGDRVTITCQASQSIDSWLSWYQQKPGKAPKLLIYQASTLASGVPSRFSGSGSGTEFTLTI

SSLQPDDFATYYCQSAYGVSGTSSYLYTFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYACEVTHQGLSSPVTKSFNRGEC

324C6 HUMANIZED LIGHT CHAIN VARIABLE LIGHT CHAIN AMINO ACID
SEQUENCE. COMPIMENTARITY DETERMINING REGIONS ARE UNDERLINED
SEQ ID NO: 112
DIQMTQSPSTLSASVGDRVTITCQASQSIDSWLSWYQQKPGKAPKLLIYQASTLASGVPSRFSGSGSGTEFTLTI

SSLQPDDFATYYCQSAYGVSGTSSYLYTFGGGTKVE1K

324C6 HUMANIZED HEAVY CHAIN FULL-LENGTH NUCLEOTIDE SEQUENCE
SEQ ID NO: 113
CAGTCGCTGGTGGAGTCTGGGGGAGGCTTGGTCCAGCCTGGGGGGTCCCTGAGACTCTCCTGTACAGCCTCTGGA

TTCTCCCTCAGTAGGTACTACATGACCTGGGTCCGCCAGGCTCCAGGGAAGGGGCTGGAGTGGATCGGAACCATT

TATACTAGTGGTAGTACATGGTACGCGAGCTGGACAAAAGGCAGATTCACCATCTCCAAAGACAATACCAAGAAC

ACGGTGGATCTTCAAATGAACAGCCTGAGAGCCGAGGACACGGCTGTGTATTACTGTGCGAGATCCTATTATGGC

GGTGATAAGACTGGTTTAGGCATCTGGGGCCAGGGAACCCTGGTCACCGTCTCGAGCGCTAGCACCAAGGGCCCA

TCGGTCTTCCCCCTGGCACCCTCCTCCAAGAGCACCTCTGGGGGCACAGCGGCCCTGGGCTGCCTGGTCAAGGAC

TACTTCCCCGAACCGGTGACGGTGTCGTGGAACTCAGGCGCCCTGACCAGCGGCGTGCACACCTTCCCGGCTGTC

CTACAGTCCTCAGGACTCTACTCCCTCAGCAGCGTGGTGACCGTGCCCTCCAGCAGCTTGGGCACCCAGACCTAC

ATCTGCAACGTGAATCACAAGCCCAGCAACACCAAGGTGGACAAGAGAGTTGAGCCCAAATCTTGTGACAAAACT

CACACATGCCCACCGTGCCCAGCACCTGAAGCCGCGGGGGCACCGTCAGTCTTCCTCTTCCCCCCAAAACCCAAG

GACACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAACAGC

ACGTACCGTGTGGTCAGCGTCCTCACCGTCCTGCACCAGGACTGGCTGAATGGCAAGGAGTACAAGTGCGCGGTC

TCCAACAAAGCCCTCCCAGCCCCCATCGAGAAAACCATCTCCAAAGCCAAAGGGCAGCCCCGAGAACCACAGGTG

TACACCCTGCCCCCATCCCGGGATGAGCTGACCAAGAACCAGGTCAGCCTGACCTGCCTGGTCAAAGGCTTCTAT

CCCAGCGACATCGCCGTGGAGTGGGAGAGCAATGGGCAGCCGGAGAACAACTACAAGACCACGCCTCCCGTGCTG

GACTCCGACGGCTCCTTCTTCCTCTATAGCAAGCTCACCGTGGACAAGAGCAGGTGGCAGCAGGGGAACGTCTTC

TCATGCTCCGTGATGCATGAGGCTCTGCACAACCACTACACGCAGAAGAGCCTCTCCCTGTCTCCGGGT

324C6 HUMANIZED HEAVY CHAIN VARIABLE HEAVY CHAIN NUCLEOTIDE
SEQUENCE
SEQ ID NO: 114
CAGTCGCTGGTGGAGTCTGGGGGAGGCTTGGTCCAGCCTGGGGGGTCCCTGAGACTCTCCTGTACAGCCTCTGGA

TTCTCCCTCAGTAGGTACTACATGACCTGGGTCCGCCAGGCTCCAGGGAAGGGGCTGGAGTGGATCGGAACCATT

TATACTAGTGGTAGTACATGGTACGCGAGCTGGACAAAAGGCAGATTCACCATCTCCAAAGACAATACCAAGAAC

ACGGTGGATCTTCAAATGAACAGCCTGAGAGCCGAGGACACGGCTGTGTATTACTGTGCGAGATCCTATTATGGC

GGTGATAAGACTGGTTTAGGCATCTGGGGCCAGGGAACCCTGGTCACCGTCTCGAGC

324C6 HUMANIZED HEAVY CHAIN FULL-LENGTH AMINO ACID SEQUENCE.
HUMAN GAMMA-1 CONSTANT DOMAIN IS UNDERLINED
SEQ ID NO: 115
QSLVESGGGLVQPGGSLRLSCTASGFSLSRYYMTWVRQAPGKGLEWIGTIYTSGSTWYASWTKGRFTISKDNTKN

TVDLQMNSLRAEDTAVYYCARSYYGGDKTGLGIWGQGTLVTVSS<u>ASTKGPSVFPLAPSSKSTSGGTAALGCLVKD</u>

<u>YFPEPVTVSWNSGALTSGVHTFPAVLQSSGLYSLSSVVTVPSSSLGTQTYICNVNHKPSNTKVDKRVEPKSCDKT</u>

<u>HTCPPCPAPEAAGAPSVFLFPPKPKDTLMISRTPEVTCVVVDVSHEDPEVKFNWYVDGVEVHNAKTKPREEQYNS</u>

<u>TYRVVSVLTVLHQDWLNGKEYKCAVSNKALPAPIEKTISKAKGQPREPQVYTLPPSRDELTKNQVSLTCLVKGFY</u>

<u>PSDIAVEWESNGQPENNYKTTPPVLDSDGSFFLYSKLTVDKSRWQQGNVFSCSVMHEALHNHYTQKSLSLSPG</u>

324C6 HUMANIZED HEAVY CHAIN VARIABLE HEAVY CHAIN AMINO ACID
SEQUENCE. COMPLIMENTARITY DETERMINING REGIONS ARE UNDERLINED
SEQ ID NO: 116
QSLVESGGGLVQPGGSLRLSCTASGFSLS<u>RYYMT</u>WVRQAPGKGLEWIG<u>TIYTSGSTWYASWTKGRF</u>TISKDNTKN

TVDLQMNSLRAEDTAVYYCAR<u>SYYGGDKTGLGI</u>WGQGTLVTVSS

338H4 HUMANIZED LIGHT CHAIN FULL-LENGTH NUCLEOTIDE SEQUENCE
SEQ ID NO: 117
GACATCCAGATGACCCAGTCTCCATCCTCCCTGTCTGCATCTGTAGGAGACAGAGTCACCATCAATTGCCAGGCC

AGTCAGAACATTTACAGCTACTTATCCTGGTATCAGCAGAAACCAGGGAAAGTTCCTAAGCGCCTGATCTATCTG

GCATCTACTCTGGCATCTGGGGTCCCATCTCGGTTCAGTGGCAGTGGATCTGGGACAGATTACACTCTCACCATC

AGCAGCCTGCAGCCTGAAGATGTTGCAACTTATTACTGTCAAAGCAATTATAACGGTAATTATGGTTTCGGCGGA

GGGACCAAGGTGGAGATCAAACGTACGGTGGCTGCACCATCTGTCTTCATCTTCCCGCCATCTGATGAGCAGTTG

AAATCTGGAACTGCCTCTGTTGTGTGCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGACAGCAAGGACAGCACCTACAGCCTC

AGCAGCACCCTGACGCTGAGCAAAGCAGACTACGAGAAACACAAAGTCTACGCCTGCGAAGTCACCCATCAGGGC

CTGAGCTCGCCCGTCACAAAGAGCTTCAACAGGGGAGAGTGT

338H4 HUMANIZED LIGHT CHAIN VARIABLE LIGHT CHAIN NUCLEOTIDE
SEQUENCE
SEQ ID NO: 118
GACATCCAGATGACCCAGTCTCCATCCTCCCTGTCTGCATCTGTAGGAGACAGAGTCACCATCAATTGCCAGGCC

AGTCAGAACATTTACAGCTACTTATCCTGGTATCAGCAGAAACCAGGGAAAGTTCCTAAGCGCCTGATCTATCTG

GCATCTACTCTGGCATCTGGGGTCCCATCTCGGTTCAGTGGCAGTGGATCTGGGACAGATTACACTCTCACCATC

AGCAGCCTGCAGCCTGAAGATGTTGCAACTTATTACTGTCAAAGCAATTATAACGGTAATTATGGTTTCGGCGGA

GGGACCAAGGTGGAGATCAAA

338H4 HUMANIZED LIGHT CHAIN FULL-LENGTH AMINO ACID SEQUENCE.
HUMAN KAPPA CONSTANT DOMAIN IS UNDERLINED
SEQ ID NO: 119
DIQMTQSPSSLSASVGDRVTINCQASQNIYSYLSWYQQKPGKVPKRLIYLASTLASGVPSRFSGSGSGTDYTLTI

SSLQPEDVATYYCQSNYNGNYGFGGGTKVEIK<u>RTVAAPSVFIFPPSDEQLKSGTASVVCLLNNFYPREAKVQWKV</u>

<u>DNALQSGNSQESVTEQDSKDSTYSLSSTLTLSKADYEKHKVYACEVTHQGLSSPVTKSFNRGEC</u>

338H4 HUMANIZED LIGHT CHAIN VARIABLE LIGHT CHAIN AMINO ACID
SEQUENCE. COMPLIMENTARITY DETERMINING REGIONS ARE UNDERLINED
SEQ ID NO: 120
DIQMTQSPSSLSASVGDRVTINC<u>QASQNIYSYLS</u>WYQQKPGKVPKRLIY<u>LASTLAS</u>GVPSRFSGSGSGTDYTLTI

SSLQPEDVATYYC<u>QSNYNGNYG</u>FGGGTKVE1K

338H4 HUMANIZED HEAVY CHAIN FULL-LENGTH NUCLEOTIDE SEQUENCE
SEQ ID NO: 121
GAGGTGCAGCTGGTGGAGTCTGGGGGAGGCTTGGTCCAGCCTGGGGGGTCCCTGAGACTCTCCTGTACAGCCTCT

GGATTCTCCCTCAGTAGCTATGCAATGAGCTGGGTCCGCCAGGCTCCAGGGAGGGGGCTGGAGTGGATCGGAATC

ATTTATGCTAGTGGTAGCACATACTACGCGAGCTCGGCGAAAGGCAGATTCACCATCTCCAAAGACAATACCAAG

AACACGGTGGATCTTCAAATGAACAGCCTGAGAGCCGAGGACACGGCTGTGTATTACTGTGCGAGAATTTATGAC

```
GGCATGGACCTCTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTG

AATCACAAGCCCAGCAACACCAAGGTGGACAAGAGAGTTGAGCCCAAATCTTGTGACAAAACTCACACATGCCCA

CCGTGCCCAGCACCTGAAGCCGCGGGGGCACCGTCAGTCTTCCTCTTCCCCCCAAAACCCAAGGACACCCTCATG

ATCTCCCGGACCCCTGAGGTCACATGCGTGGTGGTGGACGTGAGCCACGAAGACCCTGAGGTCAAGTTCAACTGG

TACGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGGC

TCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT
```

338H4 HUMANIZED HEAVY CHAIN VARIABLE HEAVY CHAIN NUCLEOTIDE
SEQUENCE
SEQ ID NO: 122

```
GAGGTGCAGCTGGTGGAGTCTGGGGGAGGCTTGGTCCAGCCTGGGGGGTCCCTGAGACTCTCCTGTACAGCCTCT

GGATTCTCCCTCAGTAGCTATGCAATGAGCTGGGTCCGCCAGGCTCCAGGGAGGGGGCTGGAGTGGATCGGAATC

ATTTATGCTAGTGGTAGCACATACTACGCGAGCTCGGCGAAAGGCAGATTCACCATCTCCAAAGACAATACCAAG

AACACGGTGGATCTTCAAATGAACAGCCTGAGAGCCGAGGACACGGCTGTGTATTACTGTGCGAGAATTTATGAC

GGCATGGACCTCTGGGGCCAGGGAACCCTGGTCACCGTCTCGAGC
```

338H4 HUMANIZED HEAVY CHAIN FULL-LENGTH AMINO ACID SEQUENCE.
HUMAN GAMMA-1 CONSTANT DOMAIN IS UNDERLINED
SEQ ID NO: 123

EVQLVESGGGLVQPGGSLRLSCTASGFSLSSYAMSWVRQAPGRGLEWIGIIYASGSTYYASSAKGRFTISKDNTK

NTVDLQMNSLRAEDTAVYYCARIYDGMDLWGQGTLVTVSS<u>ASTKGPSVFPLAPSSKSTSGGTAALGCLVKDYFPE</u>

<u>PVTVSWNSGALTSGVHTFPAVLQSSGLYSLSSVVTVPSSSLGTQTYICNVNHKPSNTKVDKRVEPKSCDKTHTCP</u>

<u>PCPAPEAAGAPSVFLFPPKPKDTLMISRTPEVTCVVVDVSHEDPEVKFNWYVDGVEVHNAKTKPREEQYNSTYRV</u>

<u>VSVLTVLHQDWLNGKEYKCAVSNKALPAPIEKTISKAKGQPREPQVYTLPPSRDELTKNQVSLTCLVKGFYPSDI</u>

<u>AVEWESNGQPENNYKTTPPVLDSDGSFFLYSKLTVDKSRWQQGNVFSCSVMHEALHNHYTQKSLSLSPG</u>

338H4 HUMANIZED HEAVY CHAIN VARIABLE HEAVY CHAIN AMINO ACID
SEQUENCE. COMPLIMENTARITY DETERMINING REGIONS ARE UNDERLINED
SEQ ID NO: 124

EVQLVESGGGLVQPGGSLRLSCTASGFSLS<u>SYAMS</u>WVRQAPGRGLEWIG<u>IIYASGSTYYASSAKG</u>RFTISKDNTK

NTVDLQMNSLRAEDTAVYYCAR<u>IYDGMDL</u>WGQGTLVTVSS

330F11 HUMANIZED LIGHT CHAIN FULL-LENGTH NUCLEOTIDE SEQUENCE
SEQ ID NO: 125

```
GACATCCAGATGACCCAGTCTCCTTCCACCCTGTCTGCATCTGTAGGAGACAGAGTCACCATCACTTGCCAGGCC

AGTCAGAGCATTAATAACTACTTAGCCTGGTATCAGCAGAAACCAGGGAAAGCCCCTAAGCTCCTGATCTATAGG

GCATCCACTCTGGAATCTGGGGTCCCATCAAGGTTCAGCGGCAGTGGATCTGGGACAGAATTCACTCTCACCATC

AGCAGCCTGCAGCCTGATGATTTTGCAACTTATTACTGCAAAGCTATAATGGTGTTGGTAGGACTGCTTTCGGC

GGAGGGACCAAGGTGGAGATCAAACGTACGGTGGCTGCACCATCTGTCTTCATCTTCCCGCCATCTGATGAGCAG

TTGAAATCTGGAACTGCCTCTGTTGTGTGCCTGCTGAATAACTTCTATCCCAGAGAGGCCAAAGTACAGTGGAAG
```

GTGGATAACGCCCTCCAATCGGGTAACTCCCAGGAGAGTGTCACAGAGCAGGACAGCAAGGACAGCACCTACAGC

CTCAGCAGCACCCTGACGCTGAGCAAAGCAGACTACGAGAAACACAAAGTCTACGCCTGCGAAGTCACCCATCAG

GGCCTGAGCTCGCCCGTCACAAAGAGCTTCAACAGGGGAGAGTGT

330F11 HUMANIZED LIGHT CHAIN VARIABLE LIGHT CHAIN NUCLEOTIDE
SEQUENCE
SEQ ID NO: 126
GACATCCAGATGACCCAGTCTCCTTCCACCCTGTCTGCATCTGTAGGAGACAGAGTCACCATCACTTGCCAGGCC

AGTCAGAGCATTAATAACTACTTAGCCTGGTATCAGCAGAAACCAGGGAAAGCCCCTAAGCTCCTGATCTATAGG

GCATCCACTCTGGAATCTGGGGTCCCATCAAGGTTCAGCGGCAGTGGATCTGGGACAGAATTCACTCTCACCATC

AGCAGCCTGCAGCCTGATGATTTTGCAACTTATTACTGCCAAAGCTATAATGGTGTTGGTAGGACTGCTTTCGGC

GGAGGGACCAAGGTGGAGATCAAA

330F11 HUMANIZED LIGHT CHAIN FULL-LENGTH AMINO ACID SEQUENCE.
HUMAN KAPPA CONSTANT DOMAIN IS UNDERLINED
SEQ ID NO: 127
DIQMTQSPSTLSASVGDRVTITCQASQSINNYLAWYQQKPGKAPKLLIYRASTLESGVPSRFSGSGSGTEFTLTI

SSLQPDDFATYYCQSYNGVGRTAFGGGTKVEIK<u>RTVAAPSVFIFPPSDEQLKSGTASVVCLLNNFYPREAKVQWK</u>

<u>VDNALQSGNSQESVTEQDSKDSTYSLSSTLTLSKADYEKHKVYACEVTHQGLSSPVTKSFNRGEC</u>

330F11 HUMANIZED LIGHT CHAIN VARIABLE LIGHT CHAIN AMINO ACID
SEQUENCE. COMPIMENTARITY DETERMINING REGIONS ARE UNDERLINED
SEQ ID NO: 128
DIQMTQSPSTLSASVGDRVTITC<u>QASQSINNYLA</u>WYQQKPGKAPKLLIY<u>RASTLES</u>GVPSRFSGSGSGTEFTLTI

SSLQPDDFATYYC<u>QSYNGVGRTA</u>FGGGTKVEIK

330F11 HUMANIZED HEAVY CHAIN FULL-LENGTH NUCLEOTIDE SEQUENCE
SEQ ID NO: 129
GAGGTGCAGCTGGTGGAGTCTGGGGGAGGCTTGGTCCAGCCTGGGGGGTCCCTGAGACTCTCCTGTGCAGCCTCT

GGATTCTCCCTCAATAACTACTGGATGAGCTGGGTCCGCCAGGCTCCAGGGAAGGGGCTGGAGTGGATCGGAACC

ATTAGTAGTGGTGCGTATACATGGTTCGCCACCTGGGCGACAGGCAGATTCACCATCTCCAGAGACAATTCCAAG

AACACGCTGTATCTTCAAATGAACAGCCTGAGAGCCGAGGACACGGCTGTGTATTACTGTGCAGATATTCTTCT

ACTACTGATTGGACCTACTTTAACATCTGGGGCCAGGGAACCCTGGTCACCGTCTCGAGCGCTAGCACCAAGGGC

CCATCGGTCTTCCCCCTGGCACCCTCCTCCAAGAGCACCTCTGGGGGCACAGCGGCCCTGGGCTGCCTGGTCAAG

GACTACTTCCCCGAACCGGTGACGGTGTCGTGGAACTCAGGCGCCCTGACCAGCGGCGTGCACACCTTCCCGGCT

GTCCTACAGTCCTCAGGACTCTACTCCCTCAGCAGCGTGGTGACCGTGCCCTCCAGCAGCTTGGGCACCCAGACC

TACATCTGCAACGTGAATCACAAGCCCAGCAACACCAAGGTGGACAAGAGAGTTGAGCCCAAATCTTGTGACAAA

ACTCACACATGCCCACCGTGCCCAGCACCTGAAGCCGCGGGGGCACCGTCAGTCTTCCTCTTCCCCCCAAAACCC

AAGGACACCCTCATGATCTCCCGGACCCCTGAGGTCACATGCGTGGTGGTGGACGTGAGCCACGAAGACCCTGAG

GTCAAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGCGCG

GTCTCCAACAAAGCCCTCCCAGCCCCCATCGAGAAAACCATCTCCAAAGCCAAAGGGCAGCCCCGAGAACCACAG

GTGTACACCCTGCCCCCATCCCGGGATGAGCTGACCAAGAACCAGGTCAGCCTGACCTGCCTGGTCAAAGGCTTC

TATCCCAGCGACATCGCCGTGGAGTGGGAGAGCAATGGGCAGCCGGAGAACAACTACAAGACCACGCCTCCCGTG

CTGGACTCCGACGGCTCCTTCTTCCTCTATAGCAAGCTCACCGTGGACAAGAGCAGGTGGCAGCAGGGGAACGTC

TTCTCATGCTCCGTGATGCATGAGGCTCTGCACAACCACTACACGCAGAAGAGCCTCTCCCTGTCTCCGGGT

330F11 HUMANIZED HEAVY CHAIN VARIABLE HEAVY CHAIN NUCLEOTIDE
SEQUENCE
SEQ ID NO: 130
GAGGTGCAGCTGGTGGAGTCTGGGGGAGGCTTGGTCCAGCCTGGGGGGTCCCTGAGACTCTCCTGTGCAGCCTCT

GGATTCTCCCTCAATAACTACTGGATGAGCTGGGTCCGCCAGGCTCCAGGGAAGGGGCTGGAGTGGATCGGAACC

-continued
ATTAGTAGTGGTGCGTATACATGGTTCGCCACCTGGGCGACAGGCAGATTCACCATCTCCAGAGACAATTCCAAG

AACACGCTGTATCTTCAAATGAACAGCCTGAGAGCCGAGGACACGGCTGTGTATTACTGTGCGAGATATTCTTCT

ACTACTGATTGGACCTACTTTAACATCTGGGGCCAGGGAACCCTGGTCACCGTCTCGAGC

330F11 HUMANIZED HEAVY CHAIN FULL-LENGTH AMINO ACID SEQUENCE.
HUMAN GAMMA-1 CONSTANT DOMAIN IS UNDERLINED
SEQ ID NO: 131
EVQLVESGGGLVQPGGSLRLSCAASGFSLNNYWMSWVRQAPGKGLEWIGTISSGAYTWFATWATGRFTISRDNSK

NTLYLQMNSLRAEDTAVYYCARYSSTTDWTYFNIWGQGTLVTVSS<u>ASTKGPSVFPLAPSSKSTSGGTAALGCLVK

DYFPEPVTVSWNSGALTSGVHTFPAVLQSSGLYSLSSVVTVPSSSLGTQTYICNVNHKPSNTKVDKRVEPKSCDK

THTCPPCPAPEAAGAPSVFLFPPKPKDTLMISRTPEVTCVVVDVSHEDPEVKFNWYVDGVEVHNAKTKPREEQYN

STYRVVSVLTVLHQDWLNGKEYKCAVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALHNHYTQKSLSLSPG</u>

330F11 HUMANIZED HEAVY CHAIN VARIABLE HEAVY CHAIN AMINO ACID
SEQUENCE. COMPLIMENTARITY DETERMINING REGIONS ARE UNDERLINED
SEQ ID NO: 132
EVQLVESGGGLVQPGGSLRLSCAASGFSLN<u>NYWMS</u>WVRQAPGKGLEWIG<u>TISSGAYTWFATWATG</u>RFTISRDNSK

NTLYLQMNSLRAEDTAVYYCAR<u>YSSTTDWTYFNI</u>WGQGTLVTVSS

---

What is claimed is:

1. An isolated mAb having a binding specificity to human ROR1, comprising a light chain comprising SEQ ID NO:76 and a heavy chain comprising SEQ ID NO:80.

2. The isolated mAb according to claim 1, having a binding affinity to human ROR1 with a Kd not greater than 70 nM.

3. The isolated mAb according to claim 1, exhibiting one or more functional properties selected from high affinity binding to human ROR1, inhibiting human ROR1 activity, induction of apoptosis, regulation of EGFR signalling pathway, upregulation of EMT genes, enhancing T cell activation, stimulating antibody response, reversing the suppressive function of an immunosuppressive cell, or a combination thereof.

4. The isolated mAb according to claim 1, wherein the isolated mAb comprises a humanized antibody, a chimeric antibody, a recombinant antibody, a bispecific antibody, tri-specific antibody, multi-specific antibody, an IgG, a Fv, a Fab, a F(ab')2, a scFV or a scFV2 fragment.

5. An isolated mAb having a binding specificity to human ROR1, wherein the isolated mAb comprises complementarity determining region (CDR)1, CDR2, and CDR3 of SEQ ID NO: 76 and CDR1, CDR2, and CDR3 of SEQ ID NO:80.

6. An isolated nucleic acid encoding the isolated mAb Of according to claim 1 or 5.

7. An expression vector comprising the isolated nucleic acid of claim 6, wherein the vector is expressible in a cell.

8. A host cell comprising the nucleic acid of claim 6, wherein the host cell is a prokaryotic cell or a eukaryotic cell.

9. A method of producing an antibody comprising culturing the host cell of one of claim 8, so that the antibody is produced.

10. A pharmaceutical composition, comprising the isolated mAb Of thereof according to claim 1 or 5 or and a pharmaceutically acceptable carrier.

11. The pharmaceutical composition of claim 10, further comprising a chemotherapeutic agent, a growth inhibitory agent, a drug unit from class of calicheamicin, an antimitotic agent, a toxin, a radioactive isotope, a therapeutic agent, an anti-estrogen agent, a receptor tyrosine kinase inhibitor, a kinase inhibitor, a cell cycle inhibitor, a DNA, RNA or protein synthesis inhibitor, a RAS inhibitor, or a combination thereof.

* * * * *